United States Patent [19]
de Laszlo et al.

[11] Patent Number: 5,776,954
[45] Date of Patent: Jul. 7, 1998

[54] SUBSTITUTED PYRIDYL PYRROLES, COMPOSITIONS CONTAINING SUCH COMPOUNDS AND METHODS OF USE

[75] Inventors: Stephen E. de Laszlo, Rumson; Linda L. Chang, Wayne; Dooseop Kim, Westfield, all of N.J.; Nathan B. Mantlo, Lafayette, Colo.

[73] Assignee: Merck & Co., Inc., Rahway, N.J.

[21] Appl. No.: 742,428

[22] Filed: Oct. 30, 1996

[51] Int. Cl.⁶ .......................... A61K 31/44; C07D 403/04
[52] U.S. Cl. .................. 514/340; 546/276.4; 546/278.4; 546/278.7; 546/279.1; 546/194; 546/17; 546/269.1; 544/360; 514/318; 514/279
[58] Field of Search .................. 546/276.4, 278.4, 546/278.7, 279.1, 194, 17; 544/360, 340, 318, 279

[56] References Cited

U.S. PATENT DOCUMENTS

| | | | |
|---|---|---|---|
| 4,267,185 | 5/1981 | Finizio | 424/267 |
| 4,430,326 | 2/1984 | Hruby et al. | 424/177 |
| 4,652,582 | 3/1987 | Wilkerson | 514/427 |
| 5,286,742 | 2/1994 | Henegar et al. | 514/423 |
| 5,442,060 | 8/1995 | Jikihara et al. | 544/106 |
| 5,502,051 | 3/1996 | Scharfenberg et al. | 514/235.5 |

FOREIGN PATENT DOCUMENTS

| | | |
|---|---|---|
| 0 025 884 | 4/1981 | European Pat. Off. |
| 0 287 890 A1 | 10/1988 | European Pat. Off. |
| 0 300 688 A1 | 1/1989 | European Pat. Off. |
| 0 320 628 A1 | 6/1989 | European Pat. Off. |
| 298 913 A5 | 10/1983 | German Dem. Rep. |
| 298 915 A5 | 10/1983 | German Dem. Rep. |
| 1099500 | 1/1968 | United Kingdom. |
| WO 91/02731 | 3/1991 | WIPO. |
| WO 95/00501 | 1/1993 | WIPO. |
| WO 94/15932 | 7/1994 | WIPO. |
| WO96/17841 | 6/1996 | WIPO. |

OTHER PUBLICATIONS

Chem. Ber., vol. 122, pp. 295–300 (1989), by F. Clerici, et al.
J. of Heter. Chem., vol. 28, pp. 793–796 (1991), by S. Petruso, et al.
Heterocycles, vol. 35, No. 2, pp. 1171–1184 (1993), by Konakahara, et al.
Journal of Heterocyclic Chemistry, vol. 26, No. 2, pp. 489–492 (1989) by Silverstri, et al.
Journal of Heterocyclic Chemistry, vol. 29, No. 7, pp. 1847–1850 (1992) by Silvestri, et al.
Journal of the Chemical Society, JCS. Perkin 1, vol. 10, pp. 2642–2646 (1981), by Petruso, et al.
J. Pharm. Pharmac, vol. 26, pp. 563–565 (1974), by D. G. Kaiser.

*Primary Examiner*—C. Warren Ivy
*Assistant Examiner*—Charanjit S. Aulakh
*Attorney, Agent, or Firm*—Richard C. Billups; Mark R. Daniel

[57] ABSTRACT

The present invention addresses substituted pyridyl pyrroles, as well as compositions containing such compounds and methods of treatment. The compounds in the present invention are glucagon antagonists and inhibitors of the biosynthesis and action of TNF-α and IL1. The compounds block the action of glucagon at its receptors and thereby decrease the levels of plasma glucose. The instant pyrroles are also inhibitors of TNF-α and IL1 and may be used as antidiabetic agents as well as other cytokine mediated diseases. Cytokine mediated diseases refers to diseases or conditions in which excessive or unregulated production of one or more cytokines occurs. Interleukin-1 (IL-1) and Tumor Necrosis Factor (TNF) are cytokines produced by a variety of cells, which are involved in immunoregulation and other physiological conditions, such as inflammation.

39 Claims, No Drawings

SUBSTITUTED PYRIDYL PYRROLES, COMPOSITIONS CONTAINING SUCH COMPOUNDS AND METHODS OF USE

This application corresponds to provisional applications Ser. No. 60/007,007, filed on Oct. 25, 1995 and application Ser. No. 60/015,565, filed on Apr. 18, 1996.

BACKGROUND OF THE INVENTION

The present invention relates to pyridyl substituted pyrroles. This invention also relates to compositions containing such compounds and methods of treatment.

Diabetes is a disease process derived from multiple causative factors and characterized by elevated levels of plasma glucose. Uncontrolled hyperglycemia is associated with an increased risk for microvascular and macrovascular diseases, including nephropathy, retinopathy; hypertension, stroke and heart disease. Control of glucose levels is, therefore, a major approach to the treatment of diabetes.

Glucagon is a major counter regulatory hormone that attenuates the inhibition of liver gluconeogenesis by insulin. Glucagon receptors are found primarily in the liver, although their presence has been documented in kidney and adipose tissue.

Type II diabetics have elevated levels of plasma glucagon and increased rates of hepatic glucose production. The rate of hepatic glucose production positively correlates with fasting blood glucose levels in type II diabetics. Therefore, antagonists of glucagon are useful in improving insulin responsiveness in the liver, decreasing the rate of gluconeogenesis and lowering the rate of hepatic glucose output resulting in a decrease in the levels of plasma glucose.

Blood glucose homeostasis is also mediated by the hormone insulin, produced in the β cells of the pancreas. Deterioration of these cells is typically observed in Type I diabetics, and abnormalities in the function of these cells may occur in patients presenting the symptoms of Type II diabetes.

Cytokine mediated diseases refers to diseases or conditions in which excessive or unregulated production or activity of one or more cytokines occurs. Interleukin-1 (IL-1), Interleukin-6 (IL-6), Interleukin-8 (IL-8) and Tumor Necrosis Factor (TNF) are cytokines produced by a variety of cells, which are involved in immunoregulation and other physiological conditions, such as inflammation.

IL-1 has been demonstrated to mediate a variety of biological activities thought to be important in immunoregulation and other physiological conditions. [See, e.g., Dinarello et al., Rev. Infect. Disease, 6, 51 (1984)]. The myriad of known biological activities of IL-1 include the activation of T-helper cells, induction of fever, stimulation of prostaglandin or collagenase production, neutrophil chemotaxis, induction of acute phase proteins and the suppression of plasma iron levels.

There are many disease states in which IL-1 is implicated. Included among these diseases are rheumatoid arthritis, osteoarthritis, endotoxemia, toxic shock syndrome, other acute or chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes and pancreatic β cells.

IL-6 is a cytokine effecting the immune system, hematopoiesis and acute phase reactions. It is produced by several mammalian cell types in response to agents such as IL-1 and is correlated with disease states such as angiofollicular lymphoid hyperplasia.

IL-8 is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, and endothelial cells. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis. The compounds of formula I are also useful in treating diseases characterized by excessive IL-8 activity. There are many disease states in which excessive or unregulated IL-8 production is implicated in exacerbating and/or causing the disease. These diseases include psoriasis, inflammatory bowel disease, asthma, cardiac and renal reperfusion injury, adult respiratory distress syndrome, thrombosis and glomerulonephritis.

Excessive or unregulated TNF production has been implicated in mediating or exacerbating rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host reaction, allograft rejections, fever and myalgias due to infection, such as influenza, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Cytokines, such as TNF, have been shown to activate HIV replication in monocytes and/or macrophages [See Poli, et al., Proc. Natl. Acad. Sci., 87:782–784 (1990)]. Therefore, inhibition of monokine production or activity aids in limiting HIV progression as stated above for T-cells. TNF has also been implicated in various roles with other viral infections, such as the cytomegalovirus (CMV), influenza virus and the herpes virus.

There remains a need for compounds which are cytokine suppressive or antagonistic, i.e., compounds which are capable of interfering with, inhibiting or antagonizing cytokines such as IL-1, IL-6, IL-8 and TNF.

SUMMARY OF THE INVENTION

The present invention is directed to a compound represented by formula I:

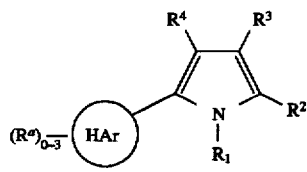

or a pharmaceutically acceptable salt, solvate, hydrate or tautomer thereof, wherein:

(HAr)

represents a heteroaryl group containing from 5 to 10 atoms, 1–4 of which are heteroatoms, 0–4 of which heteroatoms are N and 0–1 of which are O or S, said heteroaryl group being unsubstituted or substituted with 0–3 $R^a$ groups;

each $R^a$ independently represents a member selected from the group consisting of: halo, aryl($R^b$)$_{0-2}$, heteroaryl ($R^b$)$_{0-2}$, $CF_3$, $OCF_3$, CN, $N_{O2}$, $R^{21}$, $OR^{23}$, $SR^{23}$, $S(O)R^{23}$, $SO_2R^{21}$, $NR^{20}R^{23}$, $NR^{20}COR^{21}$, $NR^{20}CO_2R^{21}$, $NR^{20}CONR^{20}R^{23}$, $NR^{20}SO_2R^{21}$, $NR^{20}C(NR^{20})NHR^{23}$, $COR^{20}$, $CO_2R^{23}$, $CONR^{20}R^{23}$, $SO_2NR^{20}R^{23}$, $SO_2NR^{20}COR^{21}$, $SO_2NR^{20}CONR^{20}R^{23}$, $SO_2NR^{20}CO_2R^{21}$, $OCONR^{20}R^{23}$, $OCONR^{20}SO_2R^{21}$, $C(NR^{20})NR^{20}R^{23}$, $C(O)OCH_2OC(O)R^{20}$, $CONR^{20}SO_2R^{21}$ and $SO_2NR^{20}CO_2R^2$;

when present, each $R^b$ independently represents a member selected from the group consisting of: halo, $CF_3$, $OCF_3$, CN, $NO_2$, $OR^{23}$, $SR^{23}$, $S(O)R^{23}$, $SO_2R^{21}$, $NR^{20}R^{23}$, $NR^{20}COR^{21}$, $NR^{20}CO_2R^{21}$, $NR^{20}CONR^{20}R^{23}$, $NR^{20}SO_2R^{21}$, $NR^{20}C(NR^{20})NHR^{23}$, $COR^{20}$, $CO_2R^{23}$, $CONR^{20}R^{23}$, $SO_2NR^{20}R^{23}$, $SO_2NR^{20}COR^{21}$, $SO_2NR^{20}CONR^{20}R^{23}$, $SO_2NR^{20}CO_2R^{21}$, $OCONR^{20}R^{23}$, $OCONR^{20}SO_2R^{21}$, $C(NR^{20})NR^{20}R^{23}$, $C(O)OCH_2OC(O)R^{20}$, $CONR^{20}SO_2R^{21}$, and $SO_2NR^{20}CO_2R^2$;

$R^1$ is selected from the group consisting of: H, aryl, $C_{1-15}$ alkyl, $C_{3-15}$ alkenyl, $C_{3-15}$ alkynyl and heterocyclyl, said alkyl, aryl, alkenyl, alkynyl and heterocyclyl being optionally substituted with from one to three members selected from the group consisting of: aryl, heteroaryl, heterocyclyl, halo, $OR^{23}$, $SR^{23}$, $N(R^{23})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $COR^{20}$, $CO_2R^{23}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$;

$R^2$ is selected from the group consisting of: $C_{1-15}$ alkyl, aryl (with the proviso that aryl is not unsubstituted phenyl), heteroaryl (with the proviso that heteroaryl is not unsubstituted pyridyl), $C_{7-15}$ alkenyl, $C_{2-15}$ alkynyl, $CONR^{20}R^{23}$, $SO_2R^{21}$ (wherein $R^{21}$ is not alkyl or $C_{1-6}$ alkenyl), $SO_2N(R^{20})_2$, $SO_2NR^{20}COR^{21}$, $SO_2NR^{20}CON(R^{20})_2$, $COR^{20}$, $CO_2R^{20}$ (wherein $R^{20}$ is not $C_{1-6}$ alkyl or hydrogen), $CONR^{20}SO_2R^{21}$, $SO_2NR^{20}CO_2R^{21}$ and heterocyclyl, said alkyl, alkenyl, alkynyl, aryl, heteroaryl and heterocyclyl being optionally substituted with from one to three members selected from the group consisting of: halo, $C_{1-15}$ alkyl, $OCF_3$, $CF_3$, CN, aryl, $NO_2$, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, and $OCONR^{20}R^{23}$;

$R^3$ is selected from the group consisting of: H, aryl, $C_{1-15}$ alkyl, $C_{2-15}$ alkenyl, $C_{2-15}$ alkynyl, halo, $NO_2$, CN, $CONR^{20}R^{23}$, $SO_2R^{21}$, $SO_2N(R^{20})_2$, $SO_2NR^{20}COR^{21}$, $SO_2NR^{20}CON(R^{20})_2$, $COR^{20}$, $CO_2R^{20}$, $CONR^{20}SO_2R^{21}$, $SO_2NR^{20}CO_2R^{21}$ and heterocyclyl, said alkyl, alkenyl, alkynyl, aryl, and heterocyclyl being optionally substituted with from one to three members selected from the group consisting of: halo, $C_{1-15}$ alkyl, $CF_3$, $OCF_3$, CN, aryl, $NO_2$, heteroaryl, $OR^{23}$, $SR^{23}$, $N(R^{23})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OR^{20}$ and $OCONR^{20}R^{23}$;

$R^4$ is selected from the group consisting of $COR^{20}$, $COOR^{20}$, $CONR^{20}R^{23}$, aryl, heterocyclyl, $C_{1-15}$ alkyl, $C_{3-15}$ alkenyl, $C_{3-15}$ alkynyl, said alkyl, alkenyl and alkynyl group optionally interrupted by 1–2 oxo or heteroatoms selected from O, S, S(O), $SO_2$ or $NR^{24}$ and said $C_{1-15}$ alkyl, aryl, heterocyclyl, $C_{3-15}$ alkenyl, $C_{3-15}$ alkynyl being optionally substituted with from 1–3 of $R^{21}$, halo, aryl($R^a$)$_{0-3}$, heteroaryl($R^a$)$_{0-3}$, heterocyclyl, CN, $CF_3$, $NO_2$, $OR^{23}$, $SR^{23}$, $NR^{20}R^{23}$, $S(O)R^{21}$, $SO_2R^{21}$, $SO^2NR^{20}R^{23}$, $SO_2NR^{20}COR^{21}$, $OR^{20}CO_2R^{23}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$,

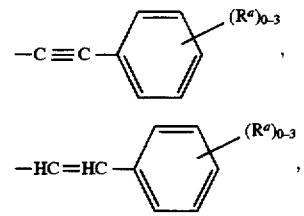

—C≡C—Heteroaryl($R^a$)$_{0-3}$, —HC=HC—Heteroaryl ($R^a$)$_{0-3}$ and $C(O)OCH_2OC(O)R^{20}$;

$R^{20}$ represents a member selected from the group consisting of: H, $C_{1-15}$ alkyl, $C_{3-15}$ alkenyl, $C_{3-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{3-15}$ alkenyl, $C_{3-15}$ alkynyl, aryl, heterocyclyl and heteroaryl; said alkyl, alkenyl or alkynyl being optionally interrupted by 1–2 heteroatoms selected from O, S, S(O), $SO_2$ or $NR^{24}$ and said alkyl, alkenyl, alkynyl, aryl, heterocyclyl and heteroaryl being optionally substituted with from 1–3 of halo, heterocyclyl, heteroaryl, aryl($R^a$)$_{0-2}$, heteroaryl ($R^a$)$_{0-2}$, CN, $OR^{20}$, $O((CH_2)_nO)_mR^{20}$, $NR^{20}((CH_2)_nO)_mR^{20}$ wherein n represents an integer of from 1 to 4, and m represents an integer of from 1 to 4; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{3-15}$ alkenyl, $C_{3-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$ and $SO_2R^{22}$; and when two $R^{20}$ groups are present, $R^{20}$ and $R^{21}$ are present, or $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

Also included in the invention is a pharmaceutical composition which is comprised of a compound of formula I in combination with a pharmaceutically acceptable carrier.

Also included in the invention is a method of treating diabetic disease, comprising administering to a mammalian patient in need of such treatment an amount of a compound of formula I which is effective to treat said diabetic disease.

Also included in the invention is a method of treating cytokine mediated disease in a mammal, comprising administering to a mammalian patient in need of such treatment an amount of a compound of formula I which is effective to treat said cytokine mediated disease.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

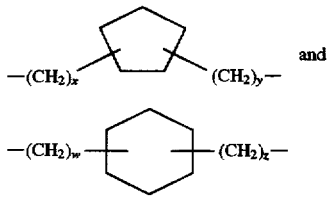

wherein: x plus y=from 0–10 and w plus z=from 0–9.

The alkylene and monovalent alkyl portion(s) of the alkyl group can be attached at any available point of attachment to the cycloalkylene portion.

When substituted, alkyl groups may be substituted with up to three substituent groups, as defined, at any available point of attachment. One of the 15 carbon atoms can be carbonyl. Thus, substitution may be in the straight or branched portion, or in the cycloalkyl portion.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 1–3 groups selected from $R^a$. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and/or in which from 1 to 3 additional carbon atoms are optionally replaced by nitrogen heteroatoms. The heteroaryl group is optionally substituted with up to three groups selected from $R^a$.

Heteroaryl thus includes aromatic and partially aromatic groups which contain one or more heteroatoms. Examples of this type are pyrrole, furan, thiophene, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyridine, pyrimidine and pyrazine.

The group

represents a heteroaryl group which contains from 5 to 10 atoms. One to four atoms are heteroatoms which are selected from O, S and N. The heteroaryl group may be unsubstituted or substituted with 0–3 $R^a$ groups.

Preferred heteroaryl groups represented by

are as follows: pyridyl, quinolyl, purinyl, imidazolyl, imidazopyridinyl and pyrimidinyl.

The terms "heterocycloalkyl" and "heterocyclyl" refer to a cycloalkyl group (nonaromatic) in which one of the carbon atoms in the ring is replaced by a heteroatom selected from O, S or N, and in which up to three additional carbon atoms may be replaced by heteroatoms.

The heterocyclyl is carbon or nitrogen linked, if said heterocyclyl is carbon linked and contains a nitrogen, then nitrogen may be substituted by $R^{24}$. One of the carbon atoms can be carbonyl. Examples of heterocyclyls are piperidinyl, morpholinyl, pyrrolidinyl, tetrahydrofuranyl, tetrahydroimidazo[4,5-c]pyridine, imidazolinyl, piperazinyl, pyrolidine-2-one, piperidin-2-one and the like.

Oxo refers to carbonyl groups —C(O)—.

The term "TNF mediated disease or disease state" refer to disease states in which TNF plays a role, either by production of TNF itself, or by TNF causing another monokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein is meant any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Tumor Necrosis Factor-alpha (TNF-α) and Tumor Necrosis Factor-beta (TNF-β).

By the term "cytokine antagonizing, interfering or cytokine suppressive amount" is meant an amount of a compound of formula I which will, cause a decrease in the in vivo presence or level of the cytokine to normal or sub-normal levels, when given to the patient for the prophylaxis or therapeutic treatment of a disease state which is exacerbated by, or caused by, excessive or unregulated cytokine production.

The compounds of the present invention may contain one or more asymmetric carbon atoms and may exist in racemic and optically active forms. All of these compounds are contemplated to be within the scope of the present invention.

Throughout the instant application, the following abbreviations are used with the following meanings:

aFGF acid fibroblast growth factor
Bu butyl
Bn benzyl
BOC, Boc t-butyloxycarbonyl
CBZ, Cbz Benzyloxycarbonyl
DCC Dicyclohexylcarbodiimide
DCM dichloromethane
DIEA diisopropylethylamine
DMF N,N-dimethylformamide
DMAP 4-Dimethylaminopyridine
DTT dithiothreitol
EDC 1-(3-dimethylaminopropyl)-3-ethylcarbodi-imide hydrochloride
Et ethyl
EtOAc ethyl acetate
EtOH ethanol
eq. equivalent(s)
FAB-MS Fast atom bombardment-mass spectroscopy
HBGF hemogloblin growth factor
HOAc acetic acid
HPLC High pressure liquid chromatography
HOBT, HOBt Hydroxybenztriazole
human serum
LAH Lithium aluminum hydride
Me methyl
NMM N-Methylmorpholine
PBS phosphate buffer saline
Ph phenyl
TFA Trifluoroacetic acid
THF Tetrahydrofuran
TMS Trimethylsilane The present invention is directed to a compound represented by formula I:

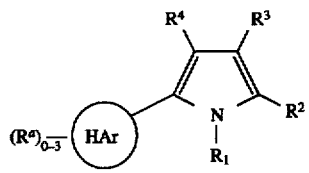

or a pharmaceutically acceptable salt, solvate, hydrate or tautomer thereof, wherein:

represents a heteroaryl group containing from 5 to 10 atoms, 1–4 of which are heteroatoms, 0–4 of which heteroatoms are N and 0–1 of which are O or S, said heteroaryl group being unsubstituted or substituted with 0–3 $R^a$ groups;

each $R^a$ independently represents a member selected from the group consisting of: halo, aryl$(R^b)_{0-2}$, heteroaryl $(R^b)_{0-2}$, $CF_3$, $OCF_3$, $CN$, $NO_2$, $R^{21}$, $OR^{23}$; $SR^{23}$, $S(O)R^{23}$, $SO_2R^{21}$, $NR^{20}R^{23}$, $NR^{20}COR^{21}$, $NR^{20}CO_2R^{21}$, $NR^{20}CONR^{20}R^{23}$, $NR^{20}SO_2R^{21}$, $NR^{20}C(NR_{20})NHR^{23}$, $COR^{20}$, $CO_2R^{23}$, $CONR^{20}R^{23}$, $SO_2NR^{20}R^{23}$, $SO_2NR^{20}COR^{21}$, $SO_2NR^{20}CONR^{20}R^{23}$, $SO_2NR^{20}CO_2R^{21}$, $OCONR^{20}R^{23}$, $OCONR^{20}SO_2R^{21}$, $C(NR^{20})NR^{20}R^{23}$, $C(O)OCH_2OC(O)R^{20}$, $CONR^{20}SO_2R^{21}$ and $SO_2NR^{20}CO_2R^2$;

when present, each $R^b$ independently represents a member selected from the group consisting of: halo, $CF_3$, $OCF_3$, $CN$, $NO_2$, $OR^{23}$; $SR^{23}$, $S(O)R^{23}$, $SO_2R^{21}$, $NR^{20}R^{23}$, $NR^{20}COR^{21}$, $NR^{20}CO_2R^{21}$, $NR^{20}CONR^{20}R^{23}$, $NR^{20}SO_2R^{21}$, $NR^{20}C(NR^{20})NHR^{23}$, $COR^{20}$, $CO_2R^{23}$, $CONR^{20}R^{23}$, $SO_2NR^{20}R^{23}$, $SO_2NR^{20}COR^{21}$, $SO_2NR^{20}CONR^{20}R^{23}$, $SO_2NR^{20}CO_2R^{21}$, $OCONR^{20}R^{23}$, $OCONR^{20}SO_2R^{21}$, $C(NR^{20})NR^{20}R^{23}$, $C(O)OCH_2OC(O)R^{20}$, $CONR^{20}SO_2R^{21}$, and $SO_2NR^{20}CO_2R^2$;

$R^1$ is selected from the group consisting of: H, aryl, $C_{1-15}$ alkyl, $C_{3-15}$ alkenyl, $C_{3-15}$ alkynyl and heterocyclyl, said alkyl, aryl, alkenyl, alkynyl and heterocyclyl being optionally substituted with from one to three members selected from the group consisting of: aryl, heteroaryl, heterocyclyl, halo, $OR^{23}$, $SR^{23}$, $N(R^{23})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR$ $NR^{20}CO_2R^{21}$, $NR^{20}CONR^{20}R^{23}$, $N(R^{20})C(NR^{20})NHR^{23}$, $COR^{20}$, $CO_2R^{23}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$;

$R^2$ is selected from the group consisting of: $C_{1-15}$ alkyl, aryl (with the proviso that aryl is not unsubstituted phenyl), heteroaryl (with the proviso that heteroaryl is not unsubstituted pyridyl), $C_{7-15}$ alkenyl, $C_{2-15}$ alkynyl, $CONR^{20}R^{23}$, $SO_2R^{21}$ (wherein $R^{21}$ is not alkyl or $C_{1-6}$ alkenyl), $SO_2N(R^{20})_2$, $SO_2NR^{20}COR^{21}$, $SO_2NR^{20}CON(R^{20})_2$, $COR^{20}$, $CO_2R^{20}$ (wherein $R^{20}$ is not $C_{1-6}$ alkyl or hydrogen), $CONR^{20}SO_2R^{21}$, $SO_2NR^{20}CO_2R^{21}$ and heterocyclyl, said alkyl, alkenyl, alkynyl, aryl, heteroaryl and heterocyclyl being optionally substituted with from one to three members selected from the group consisting of: halo, $C_{1-15}$ alkyl, $OCF_3$, $CF_3$, $CN$, aryl, $NO_2$, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, and OCONR$^{20}$R$^{23}$;

R$^3$ is selected from the group consisting of: H, aryl, C$_{1-15}$ alkyl, C$_{2-15}$ alkenyl, C$_{2-15}$ alkynyl, halo, NO$_2$, CN, CONR$^{20}$R$^{23}$, SO$_2$R$^{21}$, SO$_2$N(R$^{20}$)$_2$, SO$_2$NR$^{20}$COR$^{21}$, SO$_2$NR$^{20}$CON(R$^{20}$)$_2$, COR$^{20}$, CO$_2$R$^{20}$, CONR$^{20}$SO$_2$R$^{21}$, SO$_2$NR$^{20}$CO$_2$R$^{21}$ and heterocyclyl, said alkyl, alkenyl, alkynyl, aryl, and heterocyclyl being optionally substituted with from one to three members selected from the group consisting of: halo, C$_{1-15}$ alkyl, CF$_3$, OCF$_3$, CN, aryl, NO$_2$, heteroaryl, OR$^{23}$, SR$^{23}$, N(R$^{23}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CON(R$^{20}$)$_2$, NR$^{20}$COR$^{22}$, NR$^{20}$CO$^{22}$, NR$^{20}$CON(R$^{20}$)$_2$, NR$^{22}$C(NR$^{22}$)NHR$^{22}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OR$^{20}$ and OCONR$^{20}$R$^{23}$;

R$^4$ is selected from the group consisting of COR$^{20}$, COOR$^{20}$, CONR$^{20}$R$^{23}$, aryl, heterocyclyl, C$_{1-15}$ alkyl, C$_{3-15}$ alkenyl, C$_{3-15}$ alkynyl, said alkyl, alkenyl and alkynyl group optionally interrupted by 1-2 oxo or heteroatoms selected from O, S, S(O), SO$_2$ or NR$^{24}$ and said C$_{1-15}$ alkyl, aryl, heterocyclyl, C$_{3-15}$ alkenyl, C$_{3-15}$ alkynyl being optionally substituted with from 1–3 of R$^{21}$, halo, aryl(R$^a$)$_{0-3}$, heteroaryl(R$^a$)$_{0-3}$, heterocyclyl, CN, CF$_3$, NO$_2$, OR$^{23}$, SR$^{23}$, NR$^{20}$R$^{23}$, S(O)R$^{21}$, SO$_2$R$^{21}$, SO$_2$NR$^{20}$R$^{23}$, SO$_2$NR$^{20}$COR$^{21}$, OR$^{20}$CO$_2$R$^{23}$, SO$_2$NR$^{20}$CONR$^{20}$R$^{23}$, NR$^{20}$COR$^{21}$, NR$^{20}$CO$_2$R$^{21}$, NR$^{20}$CONR$^{20}$R$^{23}$, N(R$^{20}$)C(NR$^{20}$)NHR$^{23}$, CO$_2$R$^{23}$, COR$^{20}$, CONR$^{20}$R$^{23}$, CONR$^{20}$SO$_2$R$^{21}$, NR$^{20}$SO$_2$R$^{21}$, SO$_2$NR$^{20}$CO$_2$R$^{21}$, OCONR$^{20}$R$^{23}$, OCONR$^{20}$SO$_2$R$^{21}$, OCONR$^{20}$R$^{23}$,

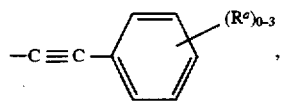

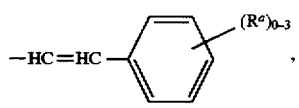

—C≡C -Heteroaryl(R$^a$)$_{0-3}$, —HC=HC-Heteroaryl (R$^a$)$_{0-3}$ and C(O)OCH$_2$C(O)R$^{20}$;

R$^{20}$ represents a member selected from the group consisting of: H, C$_{1-15}$ alkyl, C$_{3-15}$ alkenyl, C$_{3-15}$ alkynyl, heterocyclyl, aryl and heteroaryl, said alkyl, alkenyl and alkynyl being optionally substituted with 1-3 groups selected from halo, aryl and heteroaryl;

R$^{21}$ represents a member selected from the group consisting of: C$_{1-15}$ alkyl, C$_{3-15}$ alkenyl, C$_{3-15}$ alkynyl, aryl, heterocyclyl and heteroaryl; said alkyl, alkenyl or alkynyl being optionally interrupted by 1-2 heteroatoms selected from O, S, S(O), SO$_2$ or NR$^{24}$ and said alkyl, alkenyl, alkynyl, aryl, heterocyclyl and heteroaryl being optionally substituted with from 1–3 of halo, heterocyclyl, heteroaryl, aryl(R$^a$)$_{0-2}$, heteroaryl (R$^a$)$_{0-2}$, CN, OR$^{20}$, O((CH$_2$)$_n$O)$_m$R$^{20}$, NR$^{20}$((CH$_2$)$_n$O)$_m$R$^{20}$ wherein n represents an integer of from 1 to 4, and m represents an integer of from 1 to 4; SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CON(R$^{20}$)$_2$, NR$^{20}$COR$^{22}$, NR$^{20}$CO$_2$R$^{22}$, NR$^{20}$CON(R$^{22}$, NR$^{22}$C(NR$^{22}$)NHR$^{22}$, CO$_2$R$^{20}$, CON (R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OCONHR$^{20}$R$^{23}$ and OCON(R$^{20}$)$_2$;

R$^{22}$ is selected from the group consisting of: C$_{1-15}$ alkyl, C$_{3-15}$ alkenyl, C$_{3-15}$ alkynyl, heterocyclyl, aryl and heteroaryl, said alkyl, alkenyl, and alkynyl being optionally substituted with 1-3 halo, aryl or heteroaryl groups;

R$^{23}$ is R$^{21}$ or H;

R$^{24}$ is selected from aryl, COR$^{22}$, CO$_2$R$^{22}$, CON(R$^{20}$)$_2$ and SO$_2$R$^{22}$; and when two R$^{20}$ groups are present, R$^{20}$ and R$^{21}$ are present, or R$^{20}$ and R$^{23}$ are present, said two R$^{20}$ groups, R$^{20}$ and R$^{21}$ or said R$^{20}$ and R$^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

More particularly, a preferred aspect of the present invention is directed to a compound represented by formula I:

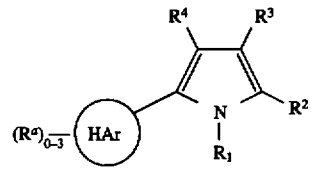

or a pharmaceutically acceptable salt thereof, wherein:

represents a heteroaryl group containing from 5 to 10 atoms, 1–4 of which are heteroatoms, 0–4 of which heteroatoms are N and 0–1 of which are O or S, said heteroaryl group being unsubstituted or substituted with 0–3 R$^a$ groups;

each R$^a$ independently represents a member selected from the group consisting of: halo, aryl(R$^b$)$_{0-2}$, heteroaryl (R$^b$)$_{0-2}$, CF$_3$, OCF$_3$, CN, NO$_2$, R$^{21}$, OR$^{23}$; SR$^{23}$, S(O) R$^{23}$, SO$_2$R$^{21}$, NR$^{20}$R$^{23}$, NR$^{20}$COR$^{21}$, NR$^{20}$CO$_2$R$^{21}$, NR$^{20}$CONR$^{20}$R$^{23}$, NR$^{20}$SO$_2$R$^{21}$, NR$^{20}$C(NR$^{20}$) NHR$^{23}$, COR$^{20}$, CO$_2$R$^{23}$, CONR$^{20}$R$^{23}$, SO$_2$NR$^{20}$R$^{23}$, SO$_2$NR$^{20}$COR$^{21}$, SO$_2$NR$^{20}$CONR$^{20}$R$^{23}$, SO$_2$NR$^{20}$CO$_2$R$^{21}$, OCONR$^{20}$R$^{23}$, OCONR$^{20}$SO$_2$R$^{21}$, C(NR$^{20}$)NR$^{20}$R$^{23}$, C(O)OCH$_2$OC(O)R$^{20}$, CONR$^{20}$SO$_2$R$^{21}$, and SO$_2$NR$^{20}$CO$_2$R$^2$;

Rb is R$^a$ minus aryl, heteroaryl and R$^{21}$;

R$^1$ is selected from the group consisting of: H, aryl, C$_{1-15}$ alkyl, C$_{3-15}$ alkenyl, C$_{3-15}$ alkynyl and heterocyclyl, said alkyl, aryl, alkenyl, alkynyl, and heterocyclyl being optionally substituted with from one to three members selected from the group consisting of: aryl, heteroaryl, heterocyclyl, halo, OR$^{23}$, SR$^{23}$, N(R$^{23}$)$_2$, S(O)R$^{21}$, SO$_2$NR$^{20}$R$^{23}$, SO$_2$NR$^{20}$COR$^{21}$, SO$_2$NR$^{20}$CONR$^{20}$R$^{23}$, NR$^{20}$COR$^{21}$, NR$^{20}$CO$_2$R$^{21}$, NR$^{20}$CONR$^{20}$R$^{23}$, N(R$^{20}$)C(NR$^{20}$)NHR$^{23}$, COR$^{20}$, CO$_2$R$^{23}$, CONR$^{20}$R$^{23}$, CONR$^{20}$SO$_2$R$^{21}$, NR$^{20}$SO$_2$R$^{21}$, SO$_2$NR$^{20}$CO$_2$R$^{21}$, OCONR$^{20}$R$^{23}$, OCONR$^{20}$SO$_2$R$^{21}$, OCONR$^{20}$R$^{23}$ and C(O)OCH$_2$OC(O)R$^{20}$;

R$^2$ is selected from the group consisting of: aryl (wherein aryl is not unsubstituted phenyl), heteroaryl (wherein heteroaryl is not unsubstituted pyridyl), C$_{7-15}$ alkenyl, C$_{2-15}$ alkynyl, CONR$^{20}$R$^{23}$, SO$_2$R$^{21}$ (wherein R$^{21}$ is not alkyl or C$_{1-6}$ alkenyl), SO$_2$N(R$^{20}$)$_2$, SO$_2$NR$^{20}$COR$^{21}$, SO$_2$NR$^{20}$CON(R$^{20}$)$_2$, COR$^{20}$, CO$_2$R$^{20}$ (wherein R$^{20}$ is not C$_{1-6}$ alkyl or hydrogen), $CONR^{20}SO_2R^{21}$, $SO_2NR^{20}CO_2R^{21}$ and heterocyclyl, said alkyl, alkenyl, alkynyl, aryl, heteroaryl and heterocyclyl being optionally substituted with from one to three members selected from the group consisting of: halo, $C_{1-15}$ alkyl, $OCF_3$, $CF_3$, CN, aryl, $NO_2$, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, and $OCONR^{20}R^{23}$;

$R^3$ is selected from the group consisting of: H, aryl, $C_{1-15}$ alkyl, $C_{2-15}$ alkenyl, $C_{2-15}$ alkynyl, halo, $NO_2$, CN, $CONR^{20}R^{23}$, $SO_2R^{21}$, $SO_2N(R^{20})_2$, $SO_2NR^{20}COR^{21}$, $SO_2NR^{20}CON(R^{20})_2$, $COR^{20}$, $CO_2R^{20}$, $CONR^{20}SO_2R^{21}$, $SO_2NR^{20}CO_2R^{21}$ and heterocyclyl, said alkyl, alkenyl, alkynyl, aryl, and heterocyclyl being optionally substituted with from one to three members selected from the group consisting of: halo, $C_{1-15}$ alkyl, $CF_3$, $OCF_3$, CN, aryl, $NO_2$, heteroaryl, $OR^{23}$, $SR^{23}$, $N(R^{23})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OR^{20}$ and $OCONR^{20}R^{23}$;

$R^4$ is selected from the group consisting of $COR^{20}$, $COOR^{20}$, $CONR^{20}R^{23}$, aryl, heterocyclyl, $C_{1-15}$ alkyl, $C_{3-15}$ alkenyl, $C_{3-15}$ alkynyl, said alkyl, alkenyl and alkynyl group optionally interrupted by 1–2 oxo or heteroatoms selected from O, S, S(O), $SO_2$ or $NR^{24}$ and said $C_{1-15}$ alkyl, aryl, heterocyclyl, $C_{3-15}$ alkenyl, $C_{3-15}$ alkynyl being optionally substituted with from 1–3 of $R^{21}$, halo, aryl$(R^a)_{0-3}$, heteroaryl$(R^a)_{0-3}$, heterocyclyl, CN, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $OR^{20}CO_2R^{23}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$;

$R^{20}$ represents a member selected from the group consisting of: H, $C_{1-15}$ alkyl, $C_{3-15}$ alkenyl, $C_{3-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{3-15}$ alkenyl, $C_{3-15}$ alkynyl, aryl, heterocyclyl and heteroaryl; said alkyl, alkenyl or alkynyl being optionally interrupted by 1–2 heteroatoms selected from O, S, S(O), $SO_2$ or $NR^{24}$ and said alkyl, alkenyl, alkynyl, aryl, heterocyclyl and heteroaryl being optionally substituted with from 1–3 of halo, heterocyclyl, heteroaryl, aryl$(R^a)_{0-2}$, heteroaryl $(R^a)_{0-2}$, CN, $OR^{20}$, $O((CH_2)_nO)_mR^{20}$, $NR^{20}((CH_2)_nO)_mR^{20}$ wherein n represents an integer of from 1 to 4, and m represents an integer of from 1 to 4; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{3-15}$ alkenyl, $C_{3-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$ and $SO_2R^{22}$; and in any substitutent wherein two $R^{20}$ groups are present, wherein $R^{20}$ and $R^{21}$ are present, or wherein $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

A subset of compounds of the invention includes compounds of formula I wherein $R^1$ represents H, alkyl, substituted alkyl, aryl and substituted aryl, said substituted groups being substituted with from 1 to 3 groups selected from $R^a$. All other variables of formula I are as originally defined.

Another subset of compounds of the invention includes compounds of formula I wherein $R^2$ represents aryl (wherein aryl is not unsubstituted phenyl), heteroaryl (wherein heteroaryl is not unsubstituted pyridyl), $C_{1-15}$ alkyl, $C_{7-15}$ alkenyl, $C_{2-15}$ alkynyl, and heterocyclyl, said alkyl, alkenyl, alkynyl, aryl, heteroaryl and heterocyclyl groups being unsubstituted or substituted with 1 to 3 groups of $R^a$. All other variables of formula I are as originally defined.

Another subset of compounds of the invention includes compounds of formula I wherein $R^3$ represents H, alkyl, halo, $NO_2$, CN, $CONR^{20}R^{23}$, $SO_2R^{21}$ and $CO_2R^{20}$, said alkyl group being unsubstituted or substituted with 1 to 3 groups of $R^a$. All other variables of formula I are as originally defined.

Another subset of compounds of the invention includes compounds of formula I wherein $R^4$ is aryl, alkyl, alkenyl, alkynyl, heterocyclyl, $CO_2R^{20}$ or $CONR^{20}R^{23}$, said aryl, alkyl, alkenyl, alkynyl, and heterocyclyl being unsubstituted or substituted with 1 to 3 groups of $R^a$. All other variables of formula I are as originally defined.

Another subset of compounds of the invention includes compounds of formula I wherein Har represents a member selected from the group consisting of: pyridinyl, quinolyl, purinyl, imidazolyl, imidazopyridinyl, pyrimidinyl, pyrrolyl, triazolyl and the like.

More particularly, a subset of compounds of the present invention includes compounds of formula I wherein Har represents a member selected from the following:

a) pyridinyl, b) quinolyl, c) purinyl, d) imidazolyl, e) imidazopyridinyl and f) pyrimidinyl.

Within this subset, all other variables are as originally defined.

More particularly, Har represents 3- or 4-pyridinyl. All other variables of formula I are as originally defined.

Another group of compounds of particular interest relates to compounds of formula I having from 1–3 $R^a$ groups attached to the Har substituent. Each $R^a$ is independently selected from the group consisting of: halo, aryl$(R^b)_{0-2}$, heteroaryl$(R^b)_{0-2}$, $CF_3$, $OCF_3$, $NO_2$, $R^{21}$, $OR^{23}$; $SR^{23}$, $S(O)R^{23}$, $SO_2R^{21}$, $NR^{20}R^{23}$, $NR^{20}COR^{21}$, $NR^{20}CO_2R^{21}$, $NR^{20}CONR^{20}R^{23}$, $NR^{20}SO_2R^{21}$, $SO_2NR^{20}R^{23}$, $SO_2NR^{20}COR^{21}$, $SO_2NR^{20}CONR^{20}R^{23}$ and $SO_2NR^{20}CO_2R^{21}$ and when present, each $R^b$, $R^{20}$, $R^{21}$, $R^{22}$, $R^{23}$ and $R^{24}$ is as originally defined.

Another set of compounds of formula I is that wherein:
$R^1$ is H, aryl, or $C_{1-15}$ alkyl;
$R^2$ is aryl (wherein aryl is not unsubstituted phenyl), heteroaryl (wherein heteroaryl is not unsubstituted pyridyl), $C_{7-15}$ alkenyl, $C_{2-15}$ alkynyl, heterocyclyl;
$R^3$ is H, halo, $NO_2$, $CO_2R^{20}$, CONHiPr or CN; and
$R^4$ is aryl, $C_{1-15}$ alkyl, $C_{2-15}$ alkenyl, $C_{2-15}$ alkynyl, $CO_2R^{20}$, $CONR^{20}R^{23}$ or heterocyclyl, said aryl, alkyl and heterocyclyl being unsubstituted or substituted with 1 to 3 groups of $R^a$.

Another set of compounds of formula I is that wherein:
$R^1$ is H or aryl;
R2 is aryl (wherein aryl is not unsubstituted phenyl), heteroaryl (wherein heteroaryl is not unsubstituted pyridyl), or heterocyclyl;
R3 is H or halo;
$R^4$ is aryl, $C_1$-$C_6$ alkyl, $C_{2-15}$ alkenyl, $C_{2-15}$ alkynyl, $CO_2R^{20}$, heterocyclyl or $CONR^{20}R^{23}$, said aryl, alkyl and heterocyclyl being unsubstituted or substituted with 1 to 3 groups of $R^a$ and
HAr is
  a) pyridinyl,
  b) quinolyl,
  c) purinyl,
  d) imidazolyl,
  e) imidazopyridinyl or
  f) pyrimidinyl.

A preferred set of compounds of formula I is that wherein:
$(R^a)_{0-3}$-HAr is:
  a) 4-pyridinyl,
  b) 2-(methyl)-4-pyridinyl,
  c) 3-(methyl)-4-pyridinyl,
  d) 2-(amino)-4-pyridinyl,
  e) 2-(benzylamino)-4-pyridinyl,
  f) 2-(acetylamino)-4-pyridinyl,
  g) 4-quinolinyl-,
  h) 4-(3-F)-quinolinyl,
  i) 2-imidazo-(4,5-b)-pyridinyl,
  j) 7-imidazo-(4,3-b)-pyridinyl,
  k) 2-imidazo-(4,5-b)-pyridinyl,
  l) 4-(2-F)-pyridinyl,
  m) 4-(3-F)-pyridinyl,
  n) 4-(2-SMe)-pyrimidinyl,
  o) 4-(2-NH2)-pyrimidinyl,
  p) 4-(2-MeNH)-pyrimidinyl,
  q) 2-(NH$_2$)-pyridinyl,
  r) 2-(MeNH)-pyridinyl,
  s) 2-(N-benzylamino)pyridinyl,
  t) 3-pyridinyl,
  u) 2-pyridinyl or
  v) 4-(2,6-di-phenyl)-pyridinyl;
$R^1$ is H or 2-(OH)-Phenyl;
$R^2$ is 1) Cl-Ph,
  2) Br-Ph,
  3) F-Ph,
  4) ($C_1$-$C_4$ alkyl)-Ph,
  5) $CF_3$-Ph
  6) (O-($C_1$-$C_4$ alkyl))-Ph,
  7) ($C_3$-$C_6$ cycloalkyl)-Ph,
  8) phenyl-Ph,
  9) CN-Ph,
  10) COOH-Ph,
  11) $NO_2$-Ph,
  12) SMe-Ph,
  13) (O-phenyl)-Ph,
  14) (S-phenyl)-Ph,
  15) (OBn)-Ph,
  16) —(S(O)-phenyl)-Ph,
  17) $OCF_3$-Ph,
  18) $CO_2$Et-Ph,
  19) —S(O)Me-Ph,
  20) ($CH_2NH_2$)-Ph,
  21) $NH_2$-Ph,
  22) N-CBz-piperdin4-yl,
  23) N-Me-piperidin-4-yl,
  24) t-butyl-Ph,
  25) 2-thiophenyl,
  26) 3,4-($OCH_2O$)-Ph,
  27) 3-(Cl)-4-(F)-Ph,
  28) —S(O)Ph,
  29) 2,4-(Cl)-Phenyl,
  30) 3,4-(Cl)-Phenyl,
  31) 2-(OMe)-4-(Cl)Ph,
  32) 4-N-(acetyl)-piperidinyl,
  33) 4-N-(OMe-CO)-piperidinyl,
  34) 4-N-(iPr-CO)-piperidinyl,
  35) 4-piperidinyl,
  36) 4-pyridinyl,
  37) c-hexyl,
  38) 4-(OBn)-Phenyl,
  39) 4-N($CO_2$Me)-piperidinyl or
  40) 3-(Me)-4-(F)-Phenyl;
$R^3$ is H, Br or Cl;
$R^4$ is 1. 4-(phenyl)-Ph,
  2. 3-(phenyl)-Ph,
  3. 4-(2-thiophenyl)-Ph,
  4. 4-(t-butyl)-Ph,
  5. 4-(toluyl)-Ph,
  6. 4-(4-fluorophenyl)-Ph,
  7. 4-(3-nitro-phenyl)-Ph,
  8. 3-(3-nitro-phenyl)-Ph,
  9. 4-(quinolinyl)-Ph,
  10. Cl-Ph,
  11. OMe-Ph,
  12. Br-Ph,
  13. $CF_3$-Ph,
  14. (cyclohexyl)-Ph,
  15. (i-butyl)-Ph,
  16. (4-(2-tetrazol-5-yl)-phenyl)-Ph,
  17. 4-(3-thiophenyl)-Ph,
  18. 2-(napthyl)-Ph,
  19. F-Ph,
  20. hydroxy-Ph,
  21. 4-$NMe_2$-Ph,
  22. $CO_2$Et-Ph,
  23. COOH-Ph,
  24. 4(OMe)-Ph,
  25. 2-(F)-4-(Br)-Ph,
  26. 4-(4-$CF_3$-phenyl)-Ph,
  27. 4-(4-OMe-phenyl)-Ph,
  28. 3-(4-OMe-phenyl)-Ph,
  29. 4-(1-naphthyl)-Ph,
  30. phenyl,
  31. 4-(4-Me-Ph)-Ph,
  32. 3-(2-thiophenyl)-Ph,
  33. 3-(3-thiophenyl)-Ph,
  34. 4-(3-(iBu)-6-($SO_2NH_2$)-Ph)-Ph,
  35. 4-(3-(iBu)-6-($SO_2NH_2$t-Bu)-Ph)-Ph, 36. 4-(4-(nBu)-Ph)-Ph,
37. 4-(3-(iBu)-6-(SO$_2$NHCO$_2$nBu)-Ph)-Ph,
38. 3-(4-(n-Bu)-Ph)-Ph,
39. 4-(3-(n-Pr)-6-(tetrazol-5-yl)-Ph)-Ph,
40. 4-(5-n-Bu)-thiophenyl-Ph,
41. 2-F-4-(2-(5-n-Bu)-thiophenyl-Ph,
42. 3,5-(2-thiophenyl)phenyl,
43. 3,4-(4-OMe-Ph)-Ph,
44. 3,5-(4-Me-Ph)-Ph,
45. 3,5-(4-SMe-Ph)-Ph,
46. 4-(NHCOMe)-Ph,
47. 4-(OCH$_2$CO$_2$Me)-Ph,
48. 3,5-(di-Bromo)-Ph,
49. 4-(iPr)-Ph,
50. 4-(OBn)-Ph,
51. 2-(OPr)-Ph,
52. —CONHBn,
53. —CON-((4-benzyl)-piperidinyl),
54. —CONHPh,
55. —CO-(4-N-phenyl-piperizin-1 -yl),
56. —CONH-((2-(2-indolyl)-phenyl),
57. —CONH-4-biphenyl,
58. —CONH-2-biphenyl,
59. 3,5-(3-nitrophenyl)-phenyl,
60. 4-(2-benzofuranyl)-phenyl,
61. 3-Br-5-(2-thiophenyl)-phenyl,
62. 4-(2-(5-Cl)-thiophenyl)-phenyl,
63. 4-(3,5-(CF$_3$)-phenyl)-phenyl,
64. 4-(2-(OMe)-phenyl)-phenyl,
65. 4-(4-Cl-phenyl)-phenyl,
66. 4-(CO$_2$Me)-phenyl,
67. 2-F-4-(2-thiophenyl)-phenyl,
68. 4-(3-(NH$_2$)-phenyl)-phenyl,
69. 4-(3-(OMe)-phenyl)-phenyl,
70. 2,6-F-Ph,
71. —ONH-2-fluorenyl,
72. —ONH-(4-(n-octyl)-phenyl),
73. —ONH-adamantyl,
74. —ONH-c-hexyl,
75. —ONH-CH(Bn)$_2$,
76. —ONHCH(Ph)2,
77. —ONHCH2CH-(Ph)$_2$,
78. —CONH-2-tetrahydo-isoquinolinyl,
79. —CO$_2$Bn,
80. 3-(OBn)-Ph,
81. 4-(CHCH-Ph)-Ph,
82. 9-phenanthrenyl,
83. 3-(OPh)-Ph,
84. 2-(OMe)-Ph,
85. CO$_2$Et,
86. COOH,
87. 4-CN-Phenyl,
88. 2,4-F-Phenyl,
89. 2,4,6, -F-Phenyl,
90. 2-(3-OMe-Ph)-Ph,
91. 2-(3-NO$_2$-Ph)-Ph,
92. 2-(thiophen-2-yl)-Ph,
93. 2-(OEt)-Ph,
94. 2-(OH)-5-(Br)-Ph,
95. 2-(OMe)-5-(Br)-Ph,
96. 2,5-(OMe)-Ph,
97. 4-(tetrazol-5-yl)-Ph,
98. 2-F-(4-(Cl)-thiophen-2-yl)-Ph,
99. 4-(CONHtBu)-Ph,
100. 4-(N-methyl-tetrazol-5-yl)-Ph,
101. 2-(Cl)-4-(Br)-Ph,
102. 2-(ethoxy)-5-(Br)-Ph,
103. 2,5-F-Ph,
104. 2-(3-(Cl)-propoxy)-Ph,
105. 2-(propoxy)-5-(Br)-Ph,
106. 2-(F)-5-(Br)-Ph,
107. 4-(CON(Bn$_2$))-Ph,
108. 4-(3-Pyr)-Ph,
109. 4-(CO-(N-Boc-piperazin)-Ph,
110. 4-(CONPn$_2$)-Ph,
111. 4-(CO-morpholinyl)-Ph,
112. 4-(CO-L-proline-OtBu)-Ph,
113. 4-(CO-spiroindane-1)-Ph,
114. 4-(CO-spiroindene-1)-Ph,
115. 4-(CON(Me)$_2$)-Ph,
116. 4-(heterocycle-1)-Ph,
117. 4-(heterocycle-2)-Ph,
118. CO$_2$-(2-Ph-Ph),
119. CHCHPh,
120. 2-(OBn)-Ph,
121. 2-(O-hexyl)-Ph,
122. 2-(O-nonyl)-Ph,
123. 2-(O-iPr)-Ph,
124. 2-(O-iBu)-Ph,
125. 4-(2-pyr)-Ph,
126. 4-(2-SO$_2$NH$_2$tBu-Ph)-2-F-Ph
127. 4-NO$_2$-Ph,
128. 4-NH$_2$-Ph or
129. 4-(NHCO$_2$-butyl)-Ph wherein:

spiroindene-1 is:

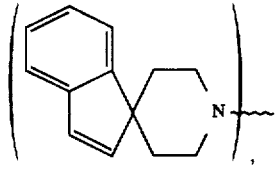

heterocycle-1 is:

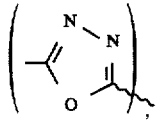

spiroindane-1 is:

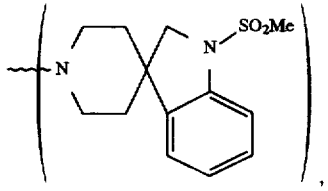

and heterocycle-2 is:

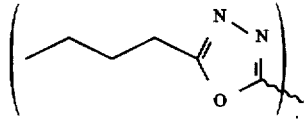

A further set of compounds includes compounds represented by formula:

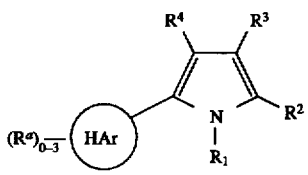

or a pharmaceutically acceptable salt thereof, wherein:

represents a heteroaryl group containing from 5 to 10 atoms, 1–3 of which are heteroatoms, 0–3 of which heteroatoms are N and 0–1 of which are O or S, said heteroaryl group being substituted with 1 –3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{23}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$, $C(NR^{20})NR^{20}R^{23}$; $C(O)OCH_2OC(O)R^{20}$; $CONR^{20}SO_2R^{21}$; and $SO_2NR^{20}CO_2R^{21}$, tetrazol-5-yl;

$R^1$ is selected from the group consisting of: H, aryl, $C_{1-15}$ alkyl, $C_{3-15}$ alkenyl, $C_{3-15}$ alkynyl; and heterocyclyl, said alkyl, aryl, alkenyl, alkynyl, and heterocyclyl being optionally substituted with from one to three members selected from the group consisting of: aryl, heteroaryl, heterocyclyl, halo, $OR^{20}$, $SR^{20}$, $N(R^{20})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $CONR^{20}R^{23}$, $CONR^{20}SO_2R^{21}$, $NR^{20}SO_2R^{21}$, $SO_2NR^{20}CO_2R^{21}OCONR^{20}R^{23}$, $OCONR^{20}SO_2R^{21}$, $OCONR^{20}R^{23}$ and $C(O)OCH_{2O}C(O)R^{20}$;

$R^2$ is selected from the group consisting of: aryl, heteroaryl, heterocyclyl, $C_{1-15}$ alkyl, $C_{2-15}$ alkenyl, $C_{2-15}$ alkynyl, said alkyl, alkenyl and alkynyl group optionally interrupted by 1–2 heteroatoms selected from O, S, S(O), $SO_2$ or $NR^{24}$ and said aryl, heteroaryl, heterocyclyl, alkyl, alkenyl, alkynyl being optionally substituted with from 1–3 of halo, aryl, heteroaryl, aryl$(R^a)_{1-2}$, $C_{1-15}$ alkyl, heteroaryl$(R^a)_{1-2}$, CN, $CF_3$, $NO_2$, heterocyclyl, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{21}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and C(O)OCH2OC(O)$R^{20}$;

$R^3$ is selected from the group consisting of: H, $C_{1-15}$ alkyl, aryl, $C_{2-15}$ alkenyl, $C_{2-15}$ alkynyl, halo, $NO_2$, $CO_2R^{22}$, CN, $CONR^{20}R^{23}$, $SO_2R^{21}$, $SO_2N(R^{20})_2$, $SO_2NR^{20}COR^{21}$, $SO_2NR^{20}CON(R^{20})_2$, $COR^{21}$, $CO_2R^{20}$, $CONR^{20}SO_2R^{21}$, $SO_2NR^{20}CO_2R^{21}$, and heterocyclyl, said alkyl, alkenyl, alkynyl, aryl, and heterocyclyl being optionally substituted with from one to three members selected from the group consisting of: halo, $C_{1-15}$ alkyl, $CF_3$, CN, aryl, $NO_2$, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OR^{20}$ and $OCONR^{20}R^{23}$;

$R^4$ is selected from the group consisting of $COR^{21}$, $CONR^{20}R^{23}$, aryl, heteroaryl, heterocyclyl, $C_{1-15}$ alkyl, $C_{3-15}$ alkenyl, $C_{3-15}$ alkynyl, said alkyl, alkenyl and alkynyl group optionally interrupted by 1–2 heteroatoms selected from O, S, S(O), $SO_2$ or $NR^{24}$ and said aryl, heteroaryl, heterocyclyl, $C_{3-15}$ alkenyl, $C_{3-15}$ alkynyl being optionally substituted with from 1–3 of $R^{21}$, halo, CN, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{21}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$; said alkyl being optionally substituted with aryl, heteroaryl, heterocyclyl, being optionally substituted with from 1–3 of $R^{21}$, halo, CN, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{21}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_{20}C(O)R^{20}$;

$R^{20}$ represents a member selected from the group consisting of: H, $C_{1-15}$ alkyl, $C_{3-15}$ alkenyl, $C_{3-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{3-15}$ alkenyl, $C_{3-15}$ alkynyl, aryl, heterocyclyl and heteroaryl; said alkyl, alkenyl or alkynyl being optionally interrupted by 1–2 heteroatoms selected from O, S, S(O), $SO_2$ or $NR^{24}$ and said alkyl, alkenyl, alkynyl, aryl, heterocyclyl and heteroaryl being optionally substituted with from 1–3 of halo, heterocyclyl, aryl, heteroaryl, aryl$(R^a)_{1-2}$, heteroaryl$(R^a)_{1-2}$, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{3-15}$ alkenyl, $C_{3-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$ and $SO_2R^{22}$;

n is 1–4;

m is 1–4;

and in a functional group substitutent wherein two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

Another subset of compounds in accordance with claim 1 is realized when:

$R^1$ is H, aryl or $C_{1-15}$ alkyl, wherein H, aryl and $C_{1-15}$ alkyl are defined above;

$R^2$ is aryl, $C_{1-15}$ alkyl, heteroaryl or heterocyclyl, wherein aryl, $C_{1-15}$ alkyl, heteroaryl and heterocyclyl are defined above;

$R^3$ is H, halo, $NO_2$ or CN; and $R^4$ is aryl, $C_{1-15}$ alkyl, heteroaryl, $COR^{21}$, $CONR^{20}R^{23}$ or heterocyclyl, wherein aryl, $C_{1-15}$ alkyl, heteroaryl, $COR^{21}$, $CONR^{20}R^{23}$ or heterocyclyl are defined above.

Still another subset of compounds in accordance with claim 1 is realized when:

$R^1$ is H, or substituted alkyl;

$R^2$ is aryl, $C_1$–$C_6$ alkyl, heteroaryl, or heterocyclyl; wherein aryl, $C_1$–$C_6$ alkyl, heteroaryl, and heterocyclyl are defined above;

$R^4$ is aryl, $C_1$–$C_6$ alkyl, heteroaryl, heterocyclyl, or $CONR^{20}R^{23}$; wherein aryl, $C_1$–$C_6$ alkyl, heteroaryl, $R^{20}$ and $R^{23}$ and heterocyclyl are defined above;

R3 is H or halo; and

HAr is
a) pyridyl,
b) quinolyl,
c) purinyl,
d) imidazolyl,
e) imidazopyridinyl, or
f) pyrimidinyl.

Still a further subset of compounds in accordance with claim 1 is realized when:

HAr is
a) 4-pyridyl-,
b) 2-methyl-4-pyridyl-,
c) 3-methyl-4-pyridyl-,
d) 2-amino-4-pyridyl-,
e) 2-benzylamino-4-pyridyl-,
f) 2-acetylamino-4-pyridyl-,
g) 4-quinolyl-,
h) 4-(2-methoxy)-pyridyl-,
i) 4-pyrimidinyl-,
j) 9-purinyl-, or
k) 7-(imidazo[4,5-b]pyridinyl)-;

$R^1$ is H;

$R^2$ is phenyl substituted with:
a) Cl,
b) Br,
c) F,
d) $C_1$–$C_4$ alkyl,
e) $CF_3$,
f) O-($C_1$–$C_4$ alkyl),
g) $C_3$–$C_6$ cycloalkyl,
h) phenyl,
i) CN,
j) COOH,
k) $NO_2$, or
l) alkyl-N(alkyl)$^2$;
m) NHCO-alkyl
n) CONHalkyl $R^3$ is H $R^4$ is a) phenyl optionally substituted with:
1. 4-phenyl,
2. 3-phenyl,
3. 4-(2-thiophenyl),
4. 4-t-butyl,
5. 4-toluyl,
6. 4-(4-fluorophenyl)-,
7. 4-(3-nitrophenyl)-,
8. 3-(3-nitrophenyl)-,
9. 4-quinolinyl,
10. Cl,
11. OMe,
12. Br,
13. $CF_3$,
14. cyclohexyl,
15. butyl,
16. (4-(2-tetrazol-5-yl)-phenyl)-,
17. 4-(3-thiophenyl)-, or
18. 2-naphthyl-;
b) 1. CONH-phenyl
2. CONH-4-biphenyl; and
3. $CH_2$-phenyl,
4. $CH_2$-4-(biphenyl), or
5. $CH_2$-4-(2'-carboxy-biphenyl).

The pharmaceutically acceptable salts of the compounds of formula I include the conventional non-toxic salts or the quaternary ammonium salts of the compounds of formula I formed e.g. from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The compounds of the present invention may have asymmetric centers and occur as racemates, racemic mixtures, and as individual diastereomers, with all possible isomers, including optical isomers, being included in the present invention.

The compounds of the present invention also may have different tautomeric forms. For example, when Har-$(R^a)_{0-3}$ represents a 4-hydroxy-3-pyridyl group, the following tautomers are equivalent and within the present invention:

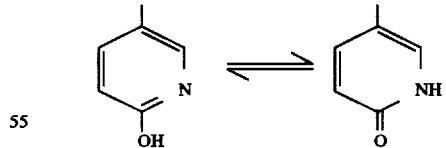

Numerous other tautomeric structures are contemplated as falling within the invention.

This invention relates to method of antagonizing or inhibiting the production or activity of glucagon, thereby reducing the rate of gluconeogenesis and the concentration of glucose in plasma.

The compounds of formula I can be used in the manufacture of a medicament for the prophylactic or therapeutic treatment of disease states in mammals caused by elevated levels of glucose.

This invention also relates to a method of inhibiting or antagonizing the production or activity of cytokines in a mammal in need thereof which comprises administering to said mammal an effective amount of a compound of formula I to antagonize or inhibit cytokine production or activity, such that it is regulated down to normal levels, or in some cases to subnormal levels, so as to ameliorate or prevent the disease state.

The compounds of formula I can be used in the manufacture of a medicament for the prophylactic or therapeutic treatment of disease states in mammals, which are exacerbated or caused by excessive or unregulated cytokine production, more specifically IL-1, IL-6, IL-8 or TNF production, by such mammal's cells, such as but not limited to monocytes and/or macrophages.

Compounds of formula I inhibit cytokines, such as IL-1, IL-6, IL-8 and TNF and are therefore useful for treating inflammatory diseases such as rheumatoid arthritis, rheumatoid spondylitis, osteoarthritis, gouty arthritis and other arthritic conditions.

The compounds of formula I may be used to treat other disease states mediated by excessive or unregulated cytokine production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegaliovirus (CMV), influenza virus, and the herpes family of viruses such as Herpes Zoster or Simplex I and II.

The compounds of formula I may also be used topically in the treatment of inflammation such as for the treatment of rheumatoid arthritis, rheumatoid spondylitis, osteoarthritis, gouty arthritis and other arthritic conditions; inflamed joints, eczema, psoriasis and other inflammatory skin conditions such as sunburn; inflammatory eye conditions including conjunctivitis; pyresis, pain and other conditions associated with inflammation.

Interleukin-I (IL-1) has been demonstrated to mediate a variety of biological activities thought to be important in immuno-regulation and other physiological conditions. [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout traumatic arthritis, rubella arthritis, and acute synovitis. Recent evidence also links IL-1 activity to diabetes and pancreatic β cells.

The compounds of formula I are also useful in treating diseases characterized by excessive IL-8 activity. There are many disease states in which excessive or unregulated IL-8 production is implicated in exacerbating and/or causing the disease. These diseases include psoriasis, inflammatory bowel disease, asthma, cardiac and renal reperfusion injury, adult respiratory distress syndrome, thrombosis and glomerulonephritis. The invention includes a method of treating psoriasis, inflammatory bowel disease, asthma, cardiac and renal reperfusion injury, adult respiratory distress syndrome, thrombosis and glomerulonephritis, in a mammal in need of such treatment which comprises administering to said mammal a compound of formula I in an amount which is effective for treating said disease or condition.

The compounds of formula I are normally formulated in accordance with standard pharmaceutical practice as a pharmaceutical composition. This invention, therefore, also relates to a pharmaceutical composition comprising a compound of formula I and a pharmaceutically acceptable carrier or diluent. The compounds of formula I are administered in conventional dosage forms prepared by combining a compound of formula I with standard pharmaceutical carriers according to conventional procedures. The compounds of formula I may also be administered in conventional dosages in combination with a known, second therapeutically active compound. These procedures may involve mixing, granulating and compressing or dissolving the ingredients as appropriate to the desired preparation.

The pharmaceutical carrier employed may be, for example, solid or liquid. Solid carriers include lactose, terra alba, sucrose, talc, gelatin, agar, pectin, acacia, magnesium stearate, stearic acid and the like. Liquid carriers include syrup, peanut oil, olive oil, water and the like. Similarly, the carrier may include time delay material, such as glyceryl monostearate or glyceryl distearate, alone or with a wax.

A wide variety of pharmaceutical forms can be employed. Thus, if a solid carrier is used, the preparation can be in the form of a tablet, hard gelatin capsule, troche or lozenge. The amount of solid will vary widely but preferably will be from about 0.025 mg to about 1 g. When a liquid carrier is used, the preparation is typically in the form of a syrup, emulsion, soft gelatin capsule, sterile injectable liquid or nonaqueous liquid suspension.

The compounds of formula I may also be administered topically in the form of a liquid, solid or semi-solid. Liquids include solutions, suspensions and emulsions. Solids include powders, poultices and the like. Semi-solids include creams, ointments, gels and the like.

The amount of a compound of formula I, for the methods of use disclosed herein, vary with the compound chosen, the nature and severity of the condition, and other factors left to the discretion of the physician. A representative, topical, anti inflammatory dose of a compound of formula I is from about 0.01 mg to about 1500 mg, administered one to four, preferably one to two times daily.

While it is possible for an active ingredient to be administered alone as the raw chemical, it is preferable to present it as a pharmaceutical formulation. The active ingredient typically comprises about 0.001% to about 90% w/w.

Drops according to the present invention may comprise sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

The methods of the instant invention may be carried out by delivering the monokine activity interfering agent parenterally. The term 'parenteral' as used herein includes intravenous, intramuscular, intradermal and subcutaneous administration. The intravenous and intramuscular forms of administration are preferred. Appropriate dosage forms for such administration may be prepared by conventional techniques. The instant invention can also be carried out by delivering the compound of formula I intranasally, rectally, transdermally or vaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by conventional techniques.

Specific examples of formula I may require the use of protecting groups to enable their successful elaboration into the desired structure.

Compounds of formula I may be prepared by the reaction of a benzoin 1, or protected version thereof with a methyl ketone 2 (commercially available or prepared by well established methods) in the presence of potassium cyanide followed by treatment with an alkyl or aryl amine or ammonia or equivalent thereof (ammonium acetate) at elevated temperature (Ceraulo, L. et al. J. Heterocyclic Chemistry 27, 255, 1990). See Scheme I Scheme I

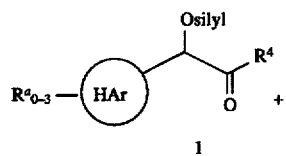

Silyl = protecting group
such as t-butyl dimethylsilyl or trimethylsilyl

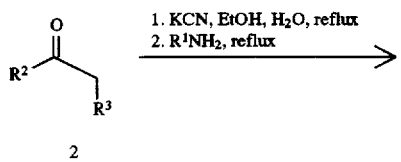

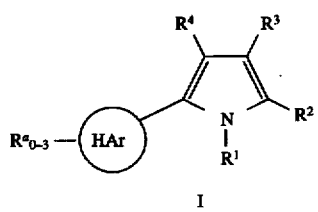

$R^1$, $R^2$, $R^3$ and $R^4$ are described above.

Compound 1 is prepared as described below. Aldehydes 3 may be converted to their trimethylsilyl cyanohydrins 4. Deprotonation and reaction with an aldehyde 5 will provide trimethyl silyl protected benzoins 1 (Hunig, S.; Wehner, G. Chem. Ber. 112, 2062 1979).

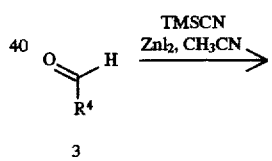

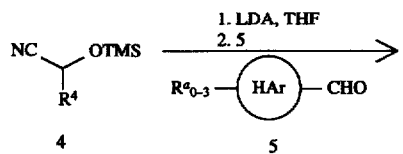

$R^4$ = aryl or heteroaryl

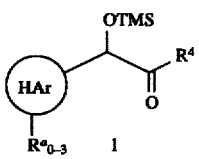

A protected heteroaryl methyl alcohol 5b may be deprotonated with a base such as n-butyl lithium in a polar aprotic solvent such as THF at a low temperature. Reaction of this anion with a Weinreb amide will provide alpha-hydroxy ketones 1.

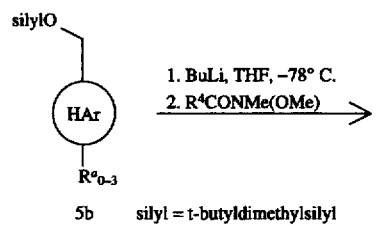

5b  silyl = t-butyldimethylsilyl

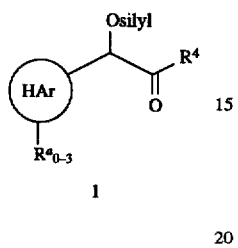

1

The condensation of a 1,4-diketone with ammonia gives rise to pyrroles (Paal Knor Synthesis). A 1,4 diketone such as 6 may be reacted with ammonia (or a compound that gives rise to ammonia such as ammonium acetate) or a primary amine to provide compounds of formula I generally in the presence of an acid catalyst such as acetic acid or titanium tetrachloride at an elevated temperature. See Scheme II Scheme II wherein $R^1$, $R^2$, $R^3$ and $R^4$ are described above.

1,4 diketones 6 may be regioselectively constructed so that the appropriate groups are present on the pyrrole ring. Alkylation of 1,2-disubstitued heteroarylethanones 7 with bromoacetophenones or other leaving group substituted acetophenones provides 1,4 diketones 6 (Iyer, R. N.; Gopalachari, R. Ind. J. Chem. 11, 1260,1973). Bromoacetophenones are readily prepared by bromination of acetophenones (for example by treatment with bromine in acetic acid or benzyltrimethylammonium bromide). Chloroketones may be prepared by treatment of activated (mixed anhydride) carboxylic acids with diazomethane followed by hydrogen chloride.

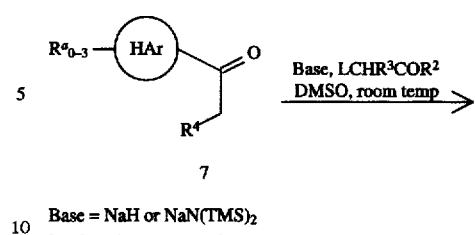

7

Base = NaH or NaN(TMS)$_2$
L = Leaving group such as Cl, Br, OTos, OMs

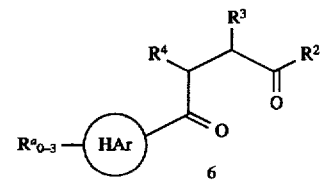

6

Ethanones 7 may be prepared by addition of anions 8 (derived by deprotonation of heteroaryl subtituted methyl groups, lithium halogen exchange of alkyl halides, or trialkyltin lithium exchange) to activated benzoic acids 9 (for example esters, acid chlorides, nitriles and N-methoxy-N-methyl amides) (see: Wolfe, J. F. et al J. Org. Chem. 39, 2006 1974 and Kaiser, E. M. et al. Synthesis 705 1975 and Ohsawa A. Chem. Pharm. Bull. 26, 3633, 1978).

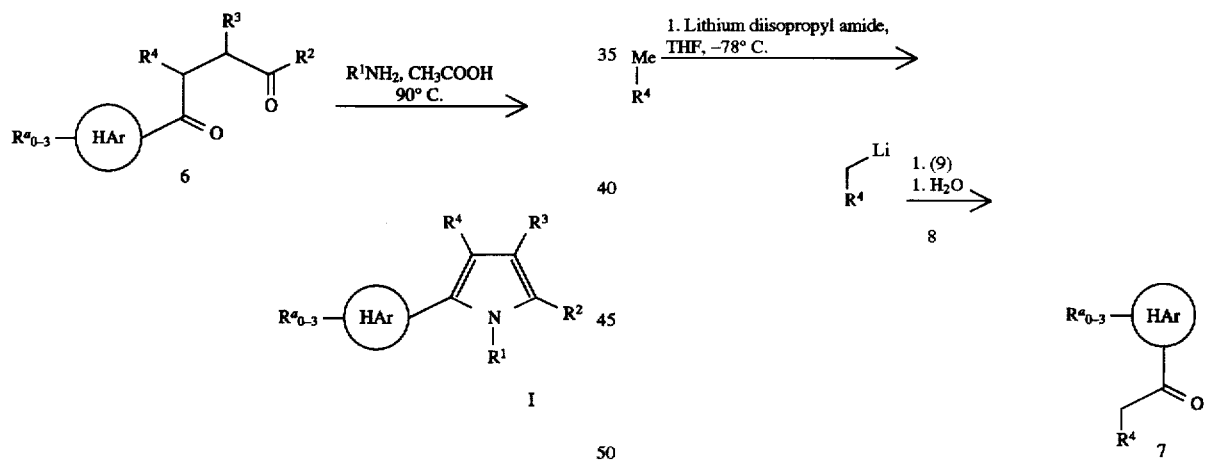

7 may also be prepared by alkylation of heteroaryl trimethyl silyl protected cyanohydrins 10. Treatment of 10 with lithium diisopropyl amide in THF and addition of a heteroaryl methyl group functionalized with a leaving group L (for example:Br, I, Cl, tosylate, mesylate) followed by acid catalyzed hydrolysis of the silyl cyanohydrin group will provide ethanones such as 7 (Deuchert, K.; Hertenstein, U.; Hunig, S.; Wehner, G. Chem. Ber. 112, 2045,1979).

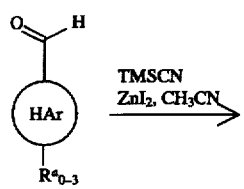

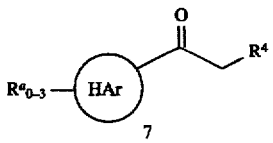

L = Br, I, Cl, OTos, OMs, OTf

The reductive cross coupling of 1,3 diketones 11 with a nitrile 12 in the presence of zinc and titanium tetrachloride may give rise to compounds of formula I (Gao, J. Hu, M.; Chen, J.; Yuan, S.; Chen, W. Tet Lett. 34, 1617, 1993). 1,3 diketones 11 may be prepared by alkylation of 4 with bromoacetophenones. See Scheme III.

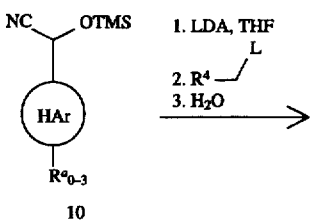

Scheme III

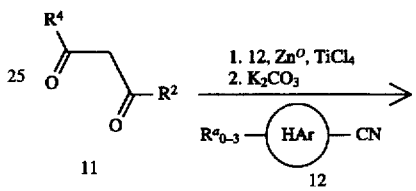

L = Br, I, Cl, OTos, OMs, OTf 7 may also be prepared by alkylation of the acetal 10a under standard conditions. 10a may be prepared from heteroaryl aldehydes by treatment with (MeO)3CH under acid catalysis.

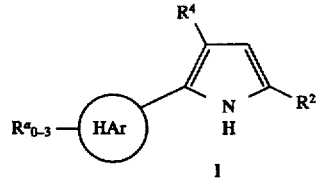

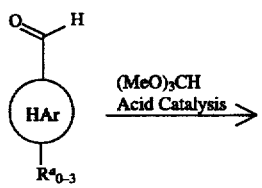

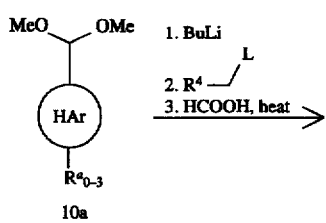

wherein $R^2$, and $R^4$ are described above. 1,4 diketones 13 may also be prepared as described below. An aldehyde 14 may be condensed in the presence of a base (for example pyridine and diethylamine or sodium hydroxide) with a methyl ketone 15 to provide an a,b-unsaturated ketone 16. In the presence of a catalyst such as cyanide or a thiazolium salt a heteroaryl aldehyde 17 will react with 16 to give 13 (Stetter, H. J. Kuhlmann, H. Organic reactions 40, 407–496 Heterocyclic Chem. 14, 573, 1977). Condensation of 13 with an amine will provide compounds of formula I. Alternatively, 7 may be condensed in the presence of a base with an aldehyde followed by dehydration to give 16a. Reaction of 16a with an aldehyde as before will give 13. See Scheme IV

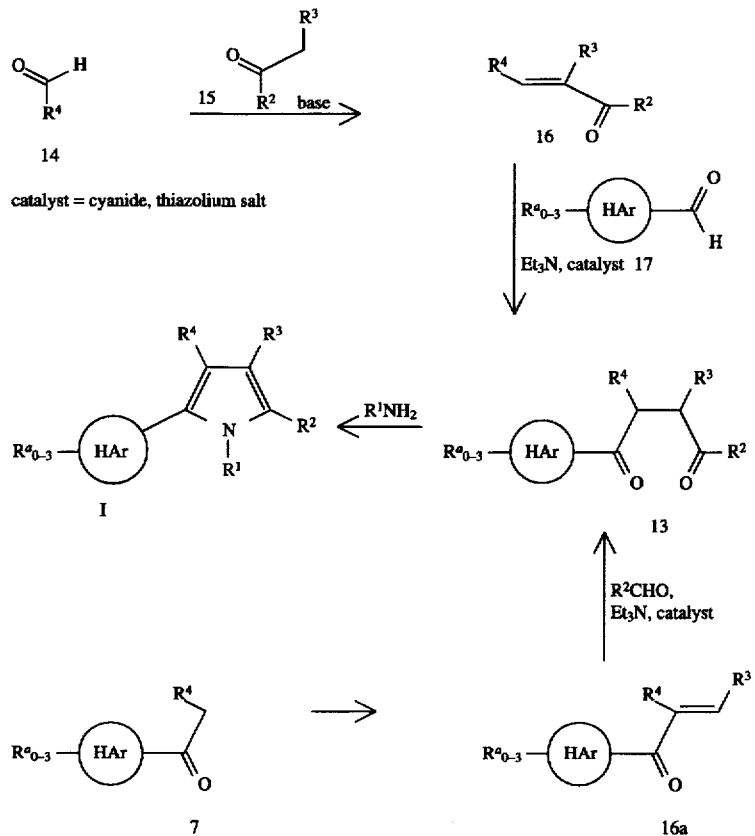

wherein $R^1$, $R^2$, R3 and $R^4$ are described above. Intermediate 16 may be prepared by the Horner-Emmons reaction of the anion of 18 with the aldehyde 14. The reagent 18 may be prepared by reaction of the bromoketone 19 and triethyl phosphite or by reaction of the lithium salt of diethyl methylphosphonate with an ester 21.

The nitro group may be introduced into the pyrrole nucleus at the $R^3$ position (generic nomenclature) by electrophilic nitration of a compound such as 22 (or a less advanced intermediate) in the presence of fuming nitric acid and acetic anhydride (Pyrroles Part 1, R. Alan Jones, ed., Heterocyclic Compounds, Vol 48 Part 1, John Wiley, New

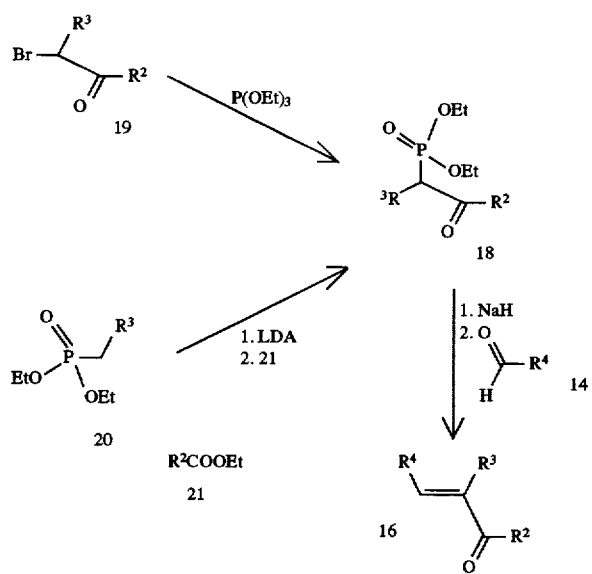

York, 1990. Pages 330–345). Halogens may be introduced by electrophilic halogation with reagents such as $XeF_2$ ($R^2=F$), N-chlorosuccinimide in DMF ($R^2=Cl$), N-bromosuccinimide in DMF ($R^3=Br$), $I_2$ in KI ($R^2=I$). Other reagents are available to carry out this conversion, the choice of reagent being dependent on the presence of functional groups that may be sensitive to the reagent being utilized (Pyrroles Part 1, R. Alan Jones,ed., Heterocyclic Compounds, Vol 48 art 1, John Wiley, New York, 1990. Pages 348–391). See Scheme V Scheme V

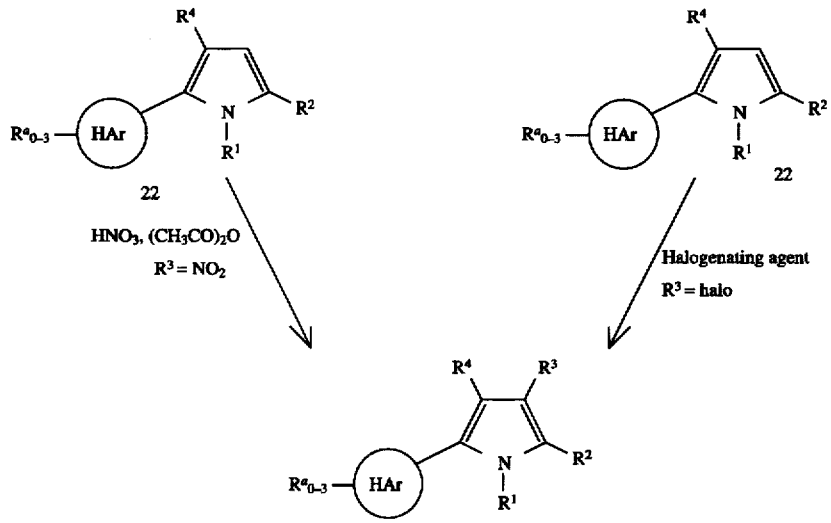

wherein $R^1$, $R^2$, $R^3$ and $R^4$ are described above.

Introduction of alkyl and heterocyclyl alkyl groups at $R^3$ is described below. Direct introduction is possible as described in the use of 1,4 diketones 6 as a precursor of compounds of formula I as described above. The preparation of a pyrrole containing a hydroxy methyl group 23 at $R^3$ would provide an intermediate that could be readily elaborated into compounds of formula 1. Acylation of the hydroxyl group with activated acids or isocyanates would provide esters and carbamates respectively of formula 1. Conversion of the hydroxy group into a leaving group 24 (for example Br, I, Cl, triflate etc.) would enable the introduction of alkyl, heterocyclyl and amines and thiol groups by displacement with a nucleophile. The nucleophile could be, for example, an alkyl or heterocyclyl anion, a primary or secondary amine or a thiol. Functional group interconversions known to those skilled in the art would provide compounds of formula I. See Scheme VI

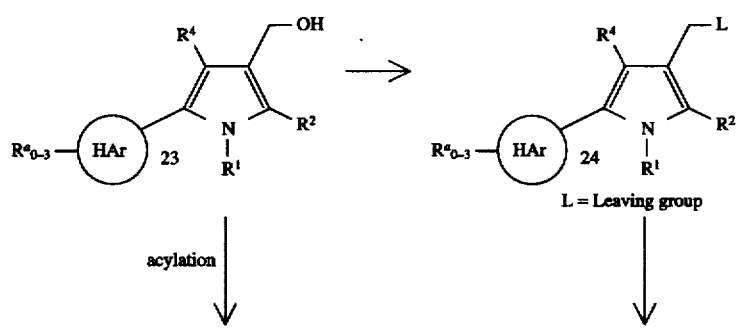

-continued
Scheme VI

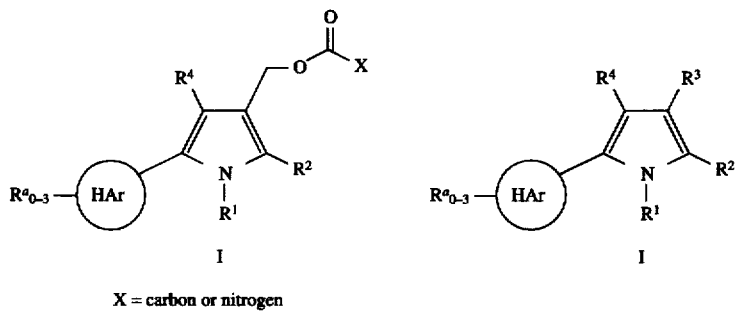

X = carbon or nitrogen wherein $R^1$, $R^2$, $R^3$ and $R^4$ are described above.

Hydroxymethyl substituted pyrroles 23 may be prepared by reduction of esters 25 by reducing agents such as lithium aluminum hydride. The esters 25 may be prepared by classical techniques. Treatment of 1,2 disubstituted-2 halo ketones 26 with 3-keto esters 27 with ammonia or amines gives esters 25 (Hantzsch. Ber. Dtsch. Chem. Ges. 23, 1474, 1890). Alternatively, 2-amino ketones 28 react with 3-keto esters 27 to give 25. A further method of synthesis of 23 is via reduction of the aldehyde 29 with a reducing agent such as sodium borohydride. The aldehyde may be prepared by treatment of the $R^3$ unsubstituted pyrrole with the Villsmeyer reagent (POCl3/DMF).

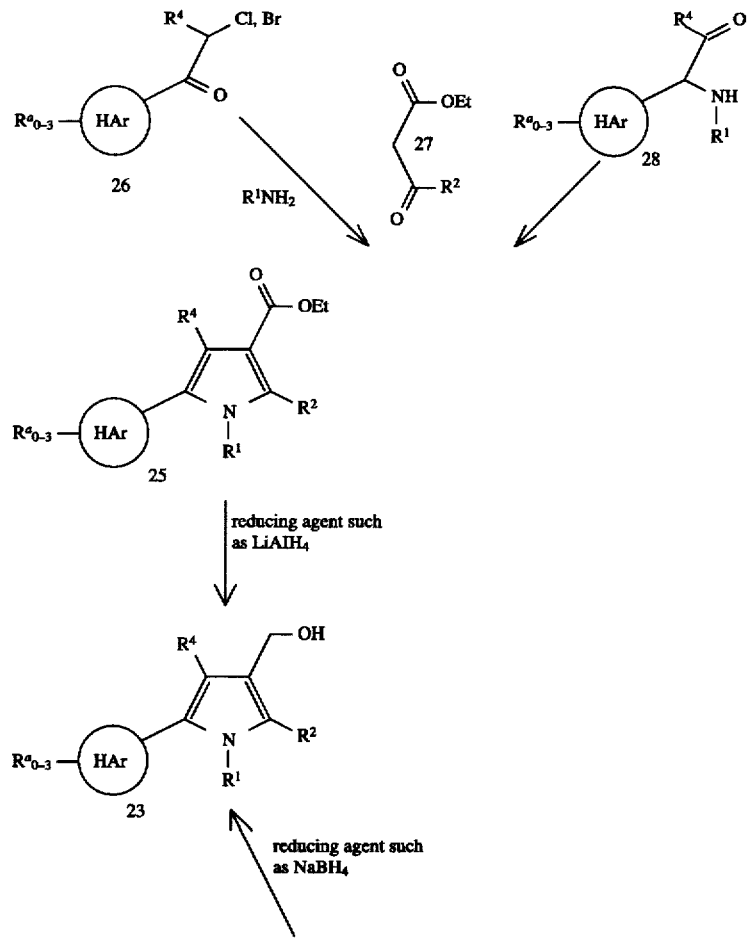

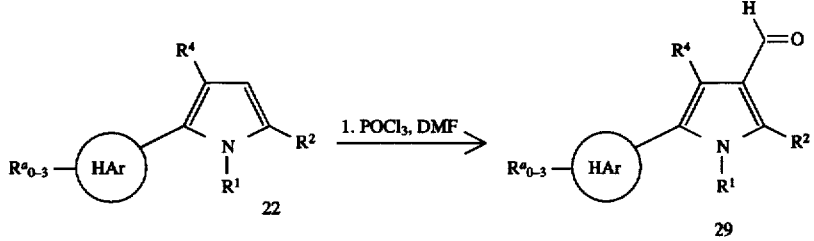

The pyrrole 22 may be silyated on nitrogen to give 30 by treatment with a silyl chloride and base in a solvent such as methylene chloride. The pyrrole 30 may then be sulphinylated with a sulphinylchloride under basic conditions to provide 31 (J. Org. Chem. 6317, 1990). Oxidation of 31 with a reagent such as m-chloroperoxy-benzoic acid will give the sulphone 32. Removal of the silyl group and derivatization of the pyrrole will give compounds of Formula 1. 22 may also be converted to the sulphide 33 by reaction of 22 with a symmetrical sulfoxide in the presence of trimethylsilylchloride. Oxidation of 33 with a reagent such as m-chloroperoxybenzoic acid will give 32. The silyl pyrrole 30 may also be acylated with an acid chloride to give the ketone 34. Removal of the silyl group from 34 and derivatization of the pyrrole will give compounds of Formula 1. Pyrroles such as 22 may also be sulphinylated directly without N-protection, by treatment with sulphinyl chlorides in a solvent such as dichloromethane at 0° C. (J. Org. Chem. 5336, 1980). Oxidation as described above may provide pyrroles of Formula 1 where $R^3$ is $SO_2R^{20}$ or 21 See Scheme VII

SCHEME VII

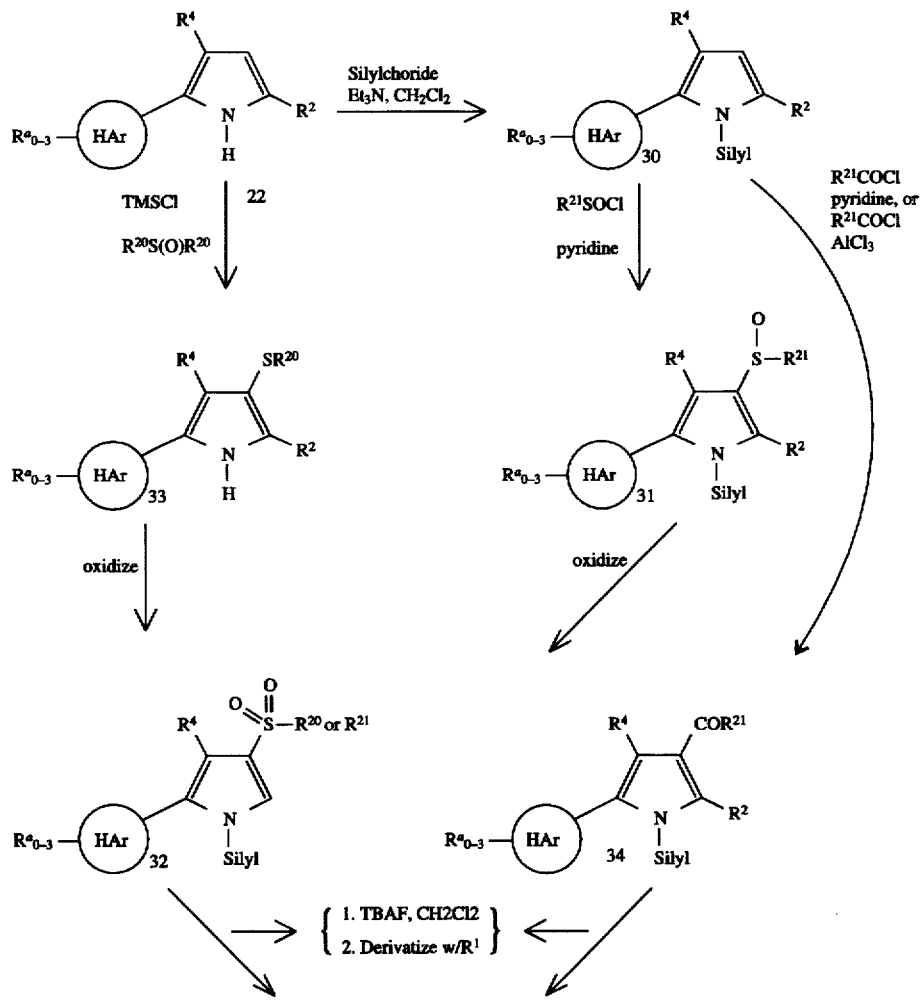

-continued
SCHEME VII

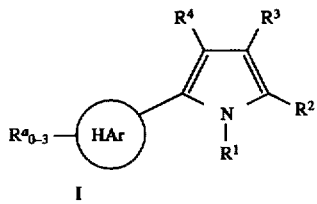

The amino acid ester 35 may be acylated with an acid 36 that is suitably activated (acid chloride or other activating group used in amide coupling reactions) to give 37. Hydrolysis of the ester protecting group will provide 38. Cyclization by treatment with an acid activating group such as DCC will give the oxazolium species 39. Addition of an alkyne 40 to 39 will give a pyrrole of Formula I via a 3+2 cyclo-addition followed by loss of carbon dioxide. Various $R^3$ groups may be incorporated in this manner. See Scheme VIII.

ment of 41 with a hexalkylditin in the presence of a palladium catalyst (see above for examples of catalysts) will give the stannyl pyrrole 42. Alternatively, halogen metal exchange through treatment of 41 with an alkyl lithium followed by addition of a trialkyltinchloride with give 42. The stannyl pyrrole may then be coupled to acid chlorides to give ketones of formula I after deblocking, if required. Reaction of 42 with chlorosulfonylisocyanate in the pres-

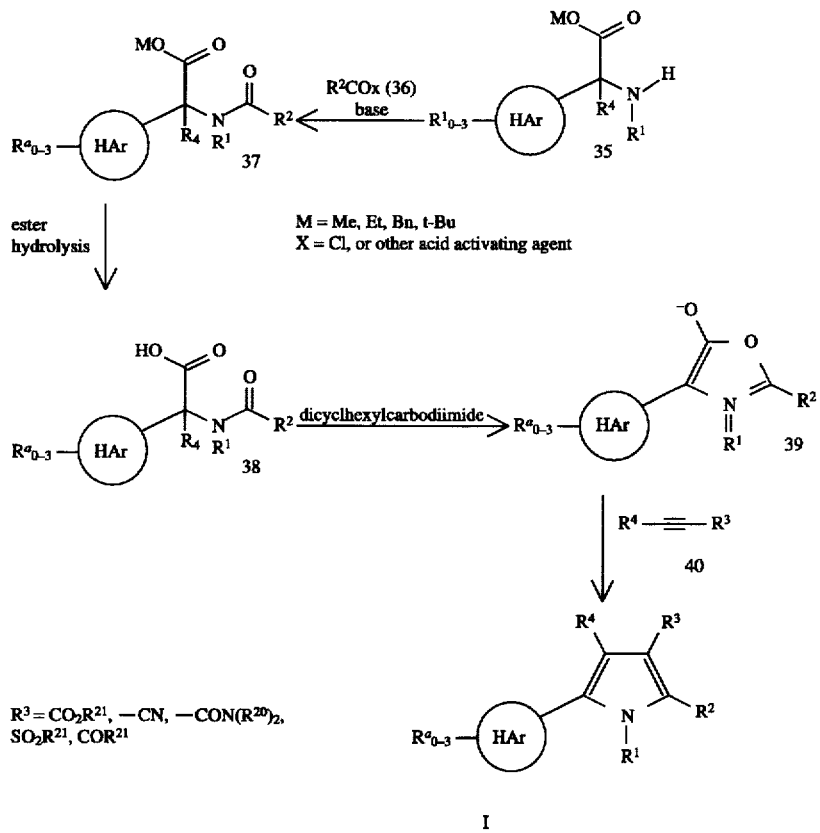

Coupling chemistry may be utilized to introduce $R^3$ groups as shown below in Scheme IX. 4-unsubstituted pyrroles optionally protected at nitrogen (P) 22 may be halogenated by treatment with electrophilic sources of bromine and iodine to provide 41. The halogen may then be coupled with carbon monoxide in the presence of an alcohol to give, after removal of the protecting group, 4-alkoxycarbonyl substituted pyrroles of formula I. Treatence of a palladium catalyst will give the sulphonyl isocyanate 43. 43 may subsequently be converted to a sulphonyl urea or sulphonyl carbamate of formula I by addition of a primary or secondary amine or an alcohol after deblocking (acid conditions for P=$CO_2$-t-Bu; basic hydrolysis for P=$SO_2$Ph), if required.

SCHEME IX
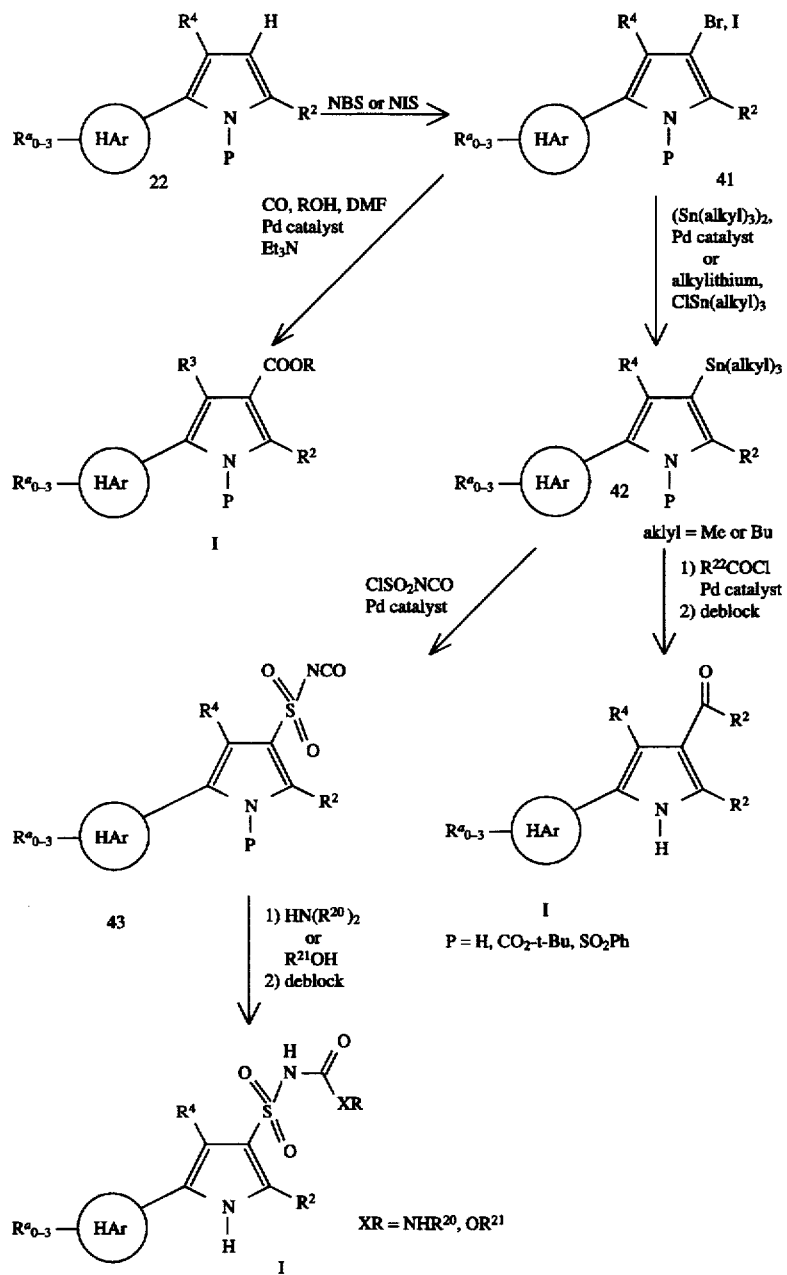
Heteroaryl rings may be appended to a pyrrole ring system by utilization of organometallic coupling technology (Kalinin, V. Synthesis 413 1991). Two alternative approaches may be utilized for appending heteroaryl rings to the pyrrole ring. The pyrrole ring may function as the electrophile or as the nucleophile as illustrated in Scheme X below:

Scheme X

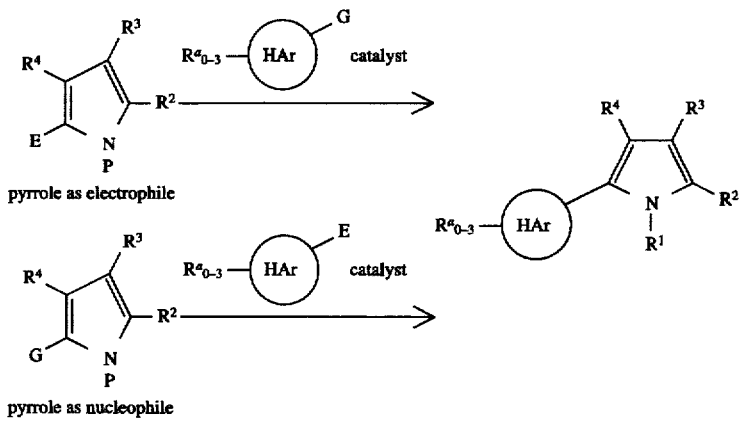

pyrrole as electrophile pyrrole as nucleophile

E = groups such as: Br, I, OSO$_2$CF$_3$
G = groups such as: SnMe$_3$, B(OH)$_2$, ZnCl, MgBr
catalyst = such as: Pd(PPh$_3$)$_4$, Pd(PPh$_3$)$_2$Cl$_2$
P = R$^2$ or protecting group such as trialkyl silyl,
benzyl, substituted benzyl, t-butyloxycarbonyl wherein R$^1$, R$^2$, R$^3$ and R$^4$ are described above.

Any appended aromatic or heteroaromatic rings may be attached to the pyrrole ring system (Alvarez, A. J. et al *J. Org. Chem.* 1653, 1992 (use of boronic acid and tributyl stannanes for coupling to aromatic and heteroaromatic rings)). Attachment of pyrrole pendant groups may be carried out with or without other HAr, R$^2$, R$^3$ or R$^4$ groups attached.

The synthesis of pyrroles containing nucleopilic groups for coupling reactions depends on the pyrrole substitution pattern. Lithium anions are prepared by metalation of a regioselectively halogenated pyrrole, or the regioselective deprotonation of the pyrrole preferably by the use of a directing functional group. The resulting anion may then be trapped by a trialkyl stannyl halide or a trialkyl borate or transmetalated to magnesium or zinc by treatment with appropriate halide salts. A further method used to incorporate a trialkyl stannyl group is the coupling of a bromo, iodo or triflate substituted pyrrole with hexaalkylditin in the presence of a palladium catalyst.

The synthesis of pyrroles incorporating electrophilic groups may be carried out by the regioselective halogenation of a pyrrole (Pyrroles Part 1, R. Alan Jones,ed., Heterocyclic Compounds, Vol 48 Part 1, John Wiley, New York, 349–391, 1990). The regioselectivity of halogenation will depend on the size, nature and substitution position on the pyrrole ring as well as the presence or absence of the N-alkyl protecting group. Triflates may be prepared by acylation of hydroxy pyrroles with triflic anhydride.

The reaction conditions used will depend on the nature of the coupling species. In the case of magnesium, zinc and stannyl coupling reactions the solvent used is normally toluene or DMF under anhydrous conditions. In the case of boronic acid couplings, a heterogenous system is used of water, toluene, dimethoxyethane or ethanol in the presence of a base such as sodium carbonate or bicarbonate. In general the reaction takes place at an elavated temperature (80°–100 ° C. ). Catalysts used depend on the structure of the components to be coupled as well as the functional groups. Most commonly, tetrakistriphenyl-phosphinepalladium (0) or palladium bis triphenyl phosphine dichloride are utilized.

Coupling of alkenes or alkynes with 4-halo pyrroles (Heck reaction, see Kalinin. V. Synthesis 413 1991 for a review) will give rise to R$^2$ (generic nomenclature) alkenyl and alkynyl substituted pyrroles that may be reduced or otherwise modified to provide compounds of formula I.

Substituents of the pendant groups of the pyrrole ring system are prepared utilizing methods well known to those skilled in the art. For example, functional groups such as halogens, sulfides, nitro groups, ethers and other groups stable to the reaction conditions used in the linear synthesis of the pyrroles are incorporated in the initial steps of the reaction sequence. Sulfides may be oxidized to sulfoxides and sulfones with reagents such as m-chloroperbenzoic acid. Sulfides may also be converted to sulfonyl chlorides by oxidation and chlorination by chlorine in water. Primary amines are prepared from nitro groups by catalytic (Pd/C, H$_2$ or Raney Nickle, H$_2$) or chemical means (CoCl$_2$, NaBH$_4$). Alkylation of amines to give secondary and tertiary amines is achieved by reductive alkylation (aldehyde, NaCNBH$_4$) or alkylation with an alkyl group substituted with a leaving group in the presence of a base such as K$_2$CO$_3$. Tertiary amines may, alternatively, be carried through the reaction sequence to the pyrroles. Acylation of primary or secondary amines with activated acids, achloroformates, isocyanates and chlorosulfonates will give rise to amides, carbamates, ureas and sulonamides respectively.

Other methods of preparing amides and ureas are useful; treatment of the amine with phosgene, or an equivalent thereof, followed by acyaltion of an alcohol or amine with the intermediate activated chloroformamide. Carboxylic acids are best introduced as esters early in the synthesis. Saponification will provide carboxylic acids. Transesterification or esterification of the acids will give esters. Carboxylic acids may be converted to amides by activation and reaction with amines. Phenols are best introduced in a protected form early in the synthetic sequence to the pyrrole. Removal of the protecting group provides a phenol which may subsequently be alkylated in the presence of an alkylating agent and base to give an ether or acylated with an isocyanate to give carbamates. Phenols may be converted to aryl ethers by reaction with an aryl bismuthane in the presence of copper II acetate.

Aryl and heteroaryl groups may be attached to pyrrole pendant aryl and heteroaryl groups by application of coupling chemistry technology as outlined above.

The sequence and conditions of the reaction steps is dependant on the structure and functional groups present. Protecting groups may be necessary and may be chosen with reference to "Protecting Groups in Organic Synthesis, Greene T. W., Wiley-Inerscience, New York, 1981". The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

The following examples are illustrative and are not limiting of the compounds of this invention.

The invention is described in connection with the following non-limiting examples.

PREPARATIVE EXAMPLE 1

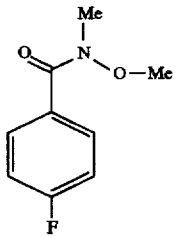

To a 2 liter 3 neck flask equipped with a magnetic stirrer was added 67.7 g of N,O-dimethylhydroxylamine and 750 ml of $CH_2Cl_2$ followed by 153 g (1.51 moles) of triethyl amine. The solution was cooled to 50° C. and treated with 100 g of 4-fluorobenzoyl chloride dropwise. The mixture was warmed to room temperature and stirred over night. The mixture was filtered and the solid was washed with ether. The organic phase was washed with water (1×2 liter) and brine (1×1 liter). The organic phase was dried over $MgSO_4$, filtered and concentrated in vacuo to give the desired product.

PREPARATIVE EXAMPLE 2

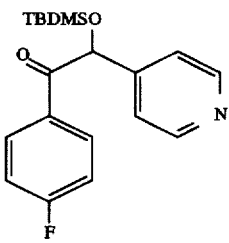

To a 2 liter 3 neck flask equipped with a mechanical stirrer under $N_2$ was added 54.6 g (0.59 m) diisopropylethylamine and 150 ml of THF. The solution was cooled to –200° C. and treated with 268 ml (0.67 m) of 2.5M butyl lithium over 20 minutes. To the reaction mixture was added 125 g (0.56 m) of 4-(t-butyldimethysilyloxymethyl)-pyridine in 100 ml of THF over 30 minutes. The reaction mixture was stirred for 1 hour at –150° C. and then treated with a solution of 108 g (0.59 m) of the product of Preparative Example 1 dissolved in 100 ml of THF dropwise. The reaction was warmed to 0° C. and stirred for 1 hour and then was warmed to room temperature and was quenched by addition of 1 liter of 20% $NH_4Cl$ solution. The aqueous phase was extracted with EtOAc (3×500 ml). The combined organic phases were washed with water (1×500 ml), 1×500 ml brine and were dried over $MgSO_4$. The mixture was filtered and the filtrate was concentrated in vacuo to give a dark oil. The product was purified by flash chromatography over silica gel eluting with 10–20% EtOAc/hexanes.

PREPARATIVE EXAMPLE 3

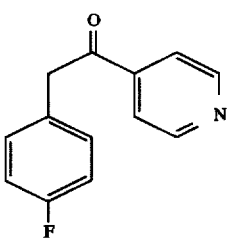

To a solution of 4-dimethoxymethylpyridine (Synthetic Comm. 23, 1967–1971, 1993) (0.94 g, (6 mmol)) in 10 ml of dry THF was added at –780° C. 4.03 ml of 1.6 M n-butyl lithium in hexanes dropwise. After 15 minutes 1.2 g (6.4 mmol) of 4-bromomethylfluorobenzene was added dropwise. The reaction mixture was allowed to gradually warm to room temperature. The mixture was diluted with 10 ml of water and 50 ml of ethyl acetate. The phases were separated and the aqueous phase was extracted with ethyl acetate (2×10 ml). The combined organic phases were washed with brine and dried over $MgSO_4$. The mixture was filtered and the filtrate was concentrated in vacuo. The residue was dissolved in 20 ml of formic acid, heated to 800° C. for 2 hours and then allowed to stand at room temperature over night. The reaction mixture was concentrated in vacuo and diluted with 20 ml of EtOAc and washed with saturated sodium bicarbonate solution. The organic phase was dried over $MgSO_4$, filtered and concentrated in vacuo to give the desired product.

$H^1$ NMR ($CDCl_3$, 300 MHz): 4.25 (s, 2H); 7.02 (t, 2H); 7.19 (dd, 2H); 7.76 (dd, 2H); 8.80 (d, 2H).

PREPARATIVE EXAMPLES 4–10

The following compounds were prepared using the method described in Preparative Example 3, with appropriate changes in the starting material.

| Prep. Example # | R |
|---|---|
| 4 | 4-Cl—Ph |
| 5 | 4-CF$_3$—Ph |
| 6 | 3-Cl—Ph |
| 7 | 4-MeO—Ph |
| 8 | 4-Br—Ph |
| 9 | 3-Br—Ph |
| 10 | 4-t-Bu—Ph |

PREPARATIVE EXAMPLE 11

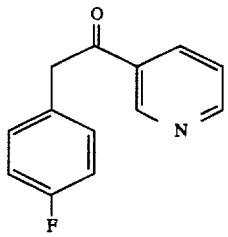

To 1.0 g (4.8 mmol) of the O-trimethylsilylcyanohydrin of 3-pyridaldehyde (Chem. Ber. 112, 2045, 1979) dissolved in 5 ml of THF at −78° C. was added 2.64 ml of 2.0 M lithium diisopropylamide. After 30 minutes 0.91 g (4.8 mmol) of 4-bromomethylfluorobenzene was added and the mixture was stirred as the temperature was permitted to increase to room temperature over 2 hours. 10 ml of 2M HCl solution followed by 5 ml of methanol (MeOH) was added and stirring was continued for 2 hours. The reaction mixture was extracted with 10 ml of ethyl acetate (EtOAc) (Ac=acetate). The EtOAc phase was extracted with IN HCl (2×10 ml). The combined acidic aqueous phases were extracted with CH$_2$Cl$_2$ (3×15 ml) and then made basic by addition of 3N NaOH solution. The resulting emulsion was extracted with CH$_2$C$_{12}$ (3×20 ml). The combined organic extracts were washed with brine (120 ml) and dried over MgSO$_4$ to give the product sufficiently pure for conversion to pyrroles as described below.

FAB m/s: C$_{13}$H$_{10}$NOF=215. Observed:216 (M+$_{+1}$). H$^1$ NMR (CDCl$_3$, 300 MHz): 4.30 (s, 2H); 7.04 (t, 2H); 7.22 (dd, 2H); 7.42 (dd, 1H); ); 8.26 (dt, 1H); 8.78 (dd, 1H); 9.21 (d, 1H).

EXAMPLES 1–23

(Method 1)

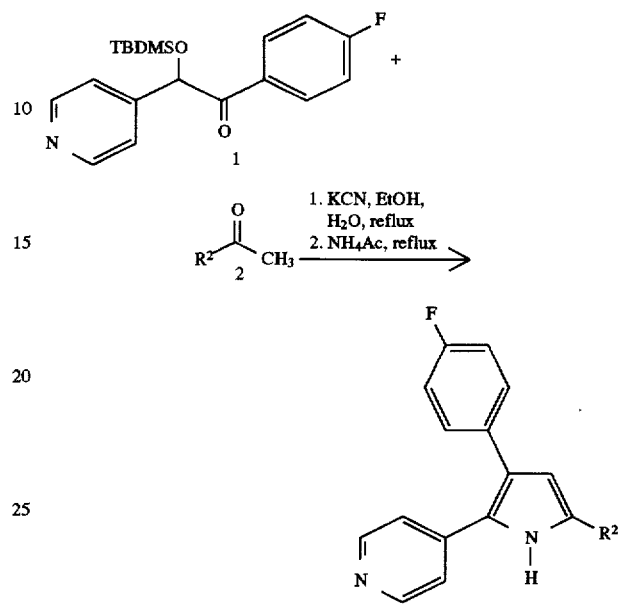

1.0 g (3.9 mmol) of 1, the product of Preparative Example 2, 2.89 mmol of an acetophenone 2, 1.1 nimol of potassium cyanide dissolved in 3.0 ml of ethanol and 0.4 ml of water were refluxed for 2–6 hours. Ammonium acetate (1.5g) was added and the 10 mixture was refluxed for 2–6 hours. The reaction mixture was cooled to room temperature, diluted with ethyl acetate and washed with saturated sodium bicarbonate and sodium chloride. The organic phase was dried over MgSO$_4$, filtered and concentrated in vacuo. The products were purified by flash chromatography over silica gel eluting 15 with ethyl acetate and hexane mixtures. The products were characterized by NMR and mass spectrum. ((TBDMS=t-butyl dimethylsilyl).

Using the procedure set forth above and substituting for compound 2, the following compounds were prepared.

| Example # | R$^2$ | FAB ms (M$^+$ + 1) |
|---|---|---|
| 1 | 4-(MeS)—Ph | 361 |
| 2 | 4-(PhO)—Ph | 407 |
| 3 | 4-(EtO)—Ph | 359 |
| 4 | 4-(c-hex)-Ph | |

-continued

| Example # | $R^2$ | FAB ms ($M^+ + 1$) |
|---|---|---|
| 5 | 4-($CF_3$)—Ph | 383 |
| 6 | 4-Br—Ph | 393 |
| 7 | 4-(t-Bu)—Ph | 371 |
| 8 | 4-Et—Ph | 343 |
| 9 | 4-(PhS)—Ph | 423 |
| 10 | 2-Me—Ph | 329 |
| 11 | 4-(MeO)—Ph | 345 |
| 12 | 4-Me—Ph | 329 |
| 13 | 4-Cl—Ph | 349 |
| 14 | 4-(n-BuO)—Ph | 387 |
| 15 | 4-(BzlO)—Ph | 421 |
| 16 | 4-F—Ph | 333 |
| 17 | 3,4-di-Cl—Ph | 383 |
| 18 | 3-$CF_3$—Ph | 383 |
| 19 | 3,4-di-F—Ph | 351 |
| 20 | 3,4-($OCH_2O$)—Ph | 359 |
| 21 | 3-Cl-4-F—Ph | 367 |
| 22 | 3-Me-4-Cl—Ph | 363 |
| 23 | 4-$CF_3O$—Ph | 399 |

Me=methyl c-hex=cyclohexyl t-Bu=t-butyl Ph=phenyl Et=ethyl Bzl=benzly Cbz=carboxybenzyl 3,4-($OCH_2O$)-Ph represents

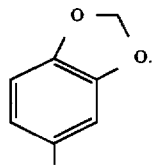

4-(BzlO)-Ph represents

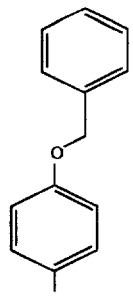

EXAMPLE 24

(Method 2)

3-(4-Chlorphenyl)-5-(4-Chlorphenyl)-2-(4-Pyridyl)-Pyrrole

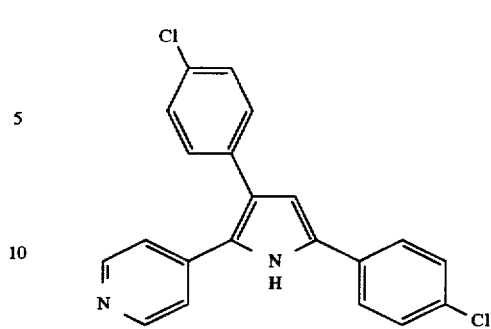

To a solution of 0.083 g (0.36 mmol) of the product of Preparative Example 4 in 1 ml of dry DMSO at room temperature was added 0.4 ml (0.4 mmol) of a 1.0M solution of sodium hexamethyldisilazide in THF. The solution was stirred for 15 minutes and then treated with a solution of 0.093 g (0.4 mmol) of 4-chlorophenacyl bromide in 0.5 ml of DMSO. The reaction mixture was stirred for 1 hour and then diluted with 10 ml of water and 5 ml of saturated $NH_4Cl$ solution. The mixture was extracted with ethyl acetate (3×10 ml) and the organic phases were combined and washed with brine (1×10 mL) and dried over $MgSO_4$. The mixture was filtered and concentrated in vacuo. The residue was dissolved in 2 ml of glacial acetic acid and heated at 110° C. in the presence of 1.0 g $NH_4OAc$ for 2 hours. The solution was diluted with 10 ml of water and extracted with EtOAc (3×10 ml). The combined organic extracts were washed with brine (1×10 ml) and dried over $MgSO_4$, filtered and concentrated in vacuo. The residue was purified by rotary chromatography over silica gel eluting with 4% MeOH/$CH_2Cl_2$ to give the desired product.

FAB ms :365 ($M+_{+1}$).

EXAMPLES 25-39

Using the procedure set forth in Example 24 (Method 2) and substituting the starting material identified in column two, the of examples 26-40 were prepared. If the starting material identified, it was prepared as described in the foregoing examples appropriate change in the starting compounds.

| Ex. # | Starting Mat. Prep. Ex. | $R^2$ | $R^4$ | HAr | FAB ms ($M^+ + 1$) |
|---|---|---|---|---|---|
| 25 | 5 | 4-Cl—Ph | 4-$CF_3$—Ph | 4-Pyr | 399 |
| 26 | 6 | 4-Cl—Ph | 3-Cl—Ph | 4-Pyr | 365 |
| 27 | 11 | 4-Cl—Ph | 4-F—Ph | 3-Pyr | 349 |
| 28 | 7 | 4-Cl—Ph | 4-MeO—Ph | 4-Pyr | 361 |
| 29 | 3 | 4-$NO_2$—Ph | 4-F—Ph | 4-Pyr | 360 |
| 30 | 3 | 3-$NO_2$—Ph | 4-F—Ph | 4-Pyr | 360 |
| 31 | 3 | 2-$NO_2$—Ph | 4-F—Ph | 4-Pyr | 360 |
| 32 | 3 | 4-($CO_2Et$)—Ph | 4-F—Ph | 4-Pyr | 387 |
| 33 | 3 | 4-CN—Ph | 4-F—Ph | 4-Pyr | 340 |
| 34 | 9 | 4-Cl—Ph | 3-Br—Ph | 4-Pyr | 411 |
| 35 | — | 4-Cl—Ph | 4-(1-naphthyl)-Ph | 4-Pyr | 457 |

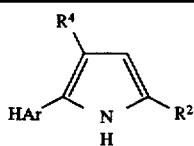

| Ex. # | Starting Mat. Prep. Ex. | R² | R⁴ | HAr | FAB ms (M⁺ + 1) |
|---|---|---|---|---|---|
| 36 | 3 | 3-CN—Ph | 4-F—Ph | 4-Pyr | 340 |
| 37 | 8 | 4-Cl—Ph | 4-Br—Ph | 4-Pyr | 411 |
| 38 | 10 | 4-Cl—Ph | 4-t-Bu—Ph | 4-Pyr | 387 |
| 39 |   | 4-Cl—Ph | 2-F-4-Br—Ph | 4-Pyr | 425 |

EXAMPLE 40

(Method 3)
5-(4-Chlorophenyl)-3-(4-Fluorophenyl)-2-(2-Pyridyl)-Pyrrole

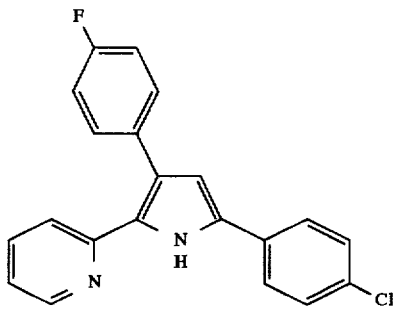

Step 1

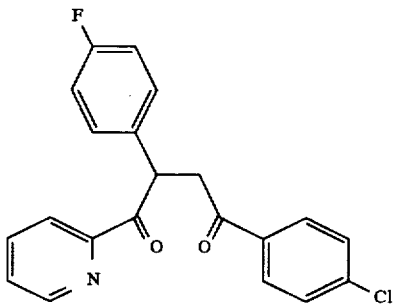

A solution of 0.5 g (1.9 nmuol) of 4-fluoro-4'-chlorochalcone in 4 ml of dioxane was treated with 47 mg (0.19 mmol) of 3-ethyl-5-(2-hydroxyethyl)-4-methylthiazolium bromide and 76 mg (0.76 mmol) triethylamine and heated to 70° C. To this mixture was added 0.22 g (2.09 mmol) of 2-pyridaldehyde, drop wise over 1.5 hours. The reaction mixture was heated for 10 hours at 70° C. and then cooled to room temperature. 5 ml of ethanol was added and the reaction mixture was concentrated in vacuo. A white precipitate formed that was collected by filtration to give the desired intermediate.

In examples where R² is pyridin-4-yl (and other heteroaryl aldehydes), pyridaldehyde is added to a suspension of 5 mole % NaCN in DMF under N₂. A red solution is formed. To this solution is added the requisite chalcone (in general prepared by condensation of an acetophenone and aldehyde in the presence of NaOH in MeOH). After approximately 4 hours the solution is diluted with EtOAc and washed with water and brine, and dried over MgSO₄. The mixture is filtered and the filtrate is concentrated in vacuo to provide the crude 1,4-diketone. The diketone is purified further by flash chromatography or committed directly to the condensation outlined below.

Step 2

0.1 g of the product from Step 1 was dissolved in 2 ml of acetic acid and heated at 110° C. for 90 minutes with 1.0 g of ammonium acetate. The reaction mixture was cooled and diluted with 5 ml of EtOAc, washed with water (2×5 ml), brine (1×5 ml) and dried over MgSO₄. The mixture was filtered and the filtrate was concentrated in vacuo to give the desired product.

FAB ms: $C_{21}H_{14}N_2ClF=348$, Observed 349 $(M+_{+1})$. $H^1$NMR (CDCl₃, 300 MHz): 6.55 (d, 1H); 7.02–7.60 (m, 11 H); 8.48 (dm, 1H); 10.40 (bs, 1 H).

EXAMPLE 41

5-(4-Methylsulfinylphenyl)-3-(4-Fluorophenyl)-2-(4-Pyridyl)-Pyrrole

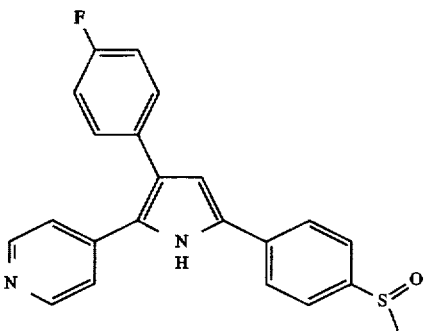

To a solution of 55.5 mg (0.15 mmol) of the product of Example 1 in 2 ml of acetic acid and 1.4 ml of water was added 50.01 mg (0.185 mmol) of potassium persulfate. The reaction mixture was stirred for 1.5 hours. The mixture was diluted with water (5 ml) and neutralized by addition of ammonium hydroxide. The resulting solid was recovered by filtration and purified by flash chromatography over silica gel eluting with 5% MeOH/CH₂Cl₂ to give the title compound.

FAB ms: $C_{22}H_{17}N_2OSF=376$, Observed 377 $(M+_{+1})$. $H^1$NMR (CDCl₃, 300 MHz): 2.70 (s, 3H); 6.90 (s, 1H); 7.08 (t, 2H); 7.23 (d, 2H); 7.35 (dd, 2H); 7.61 (d, 2H); 7.80 (d, 2H); 8.22 (d, 2H). EXAMPLE 42

3-(4-Fluorophenyl)-5-(4-Phenylsulfinylphenyl)-2-(4-Pyridyl)Pyrrole

51

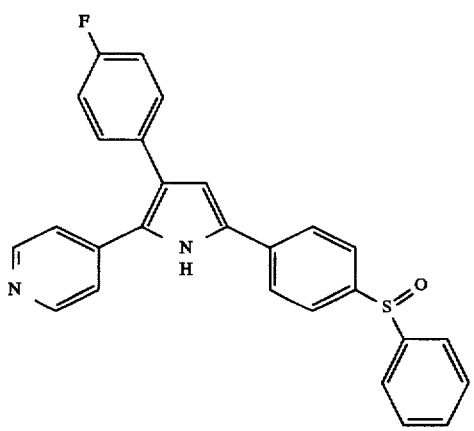

The procedure set forth in Example 41 was utilized, substituting the product of Example 9 as the starting material.

FAB ms: $C_{22}H_{17}N_2OSF=376$, Observed 377 $(M+_{+1})$.

EXAMPLE 43

5-(4-Aminomethylphenyl)-3 -(4-Fluorophenyl)-2-(4-Pyridyl)Pyrrole

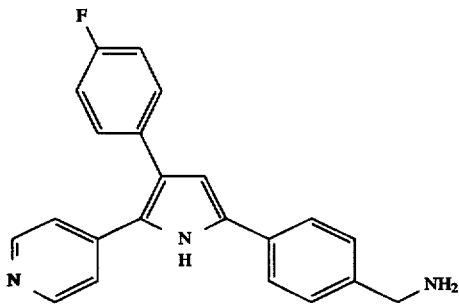

To a solution of 20 mg (0.051mmol) product of Example 33 dissolved in 2 ml of MeOH was added 0.06 g (0.253 mmol) of cobalt chloride. To this solution was added 0.02 g (0.51 mmol) of sodium borohydride. The mixture was stirred for 1 hour, diluted with EtOAc (5 ml) and washed with water (1×10 mL). The aqueous phase was extracted with EtOAc (3×10 ml) and the combined organic extracts were dried over MgSO$_4$, filtered and concentrated in vacuo. The residue was purified by chromatography over LH20 eluting with MeOH to give the desired product.

FAB ms: $C_{22}H_{18}N_3F=343$, Observed 344 $(M+_{+1})$.

H$^1$NMR (CD$_{3O}$D, 300 MHz): 4.12 (s, 2:H); 6.74 (s, 1H); 7.10 (t, 2H); 7.37 (m, 2H); 7.50 (m, 4H); 7.87 (d, 2H); 8.38 (d, 2H).

52

EXAMPLE 44–46

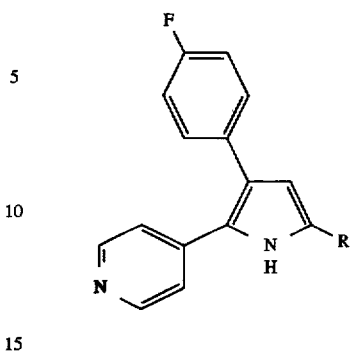

The following compounds are prepared utilizing Method 4, substituting the product of Examples 29–31, respectively, as starting materials.

| Example # | Starting Material | R |
|---|---|---|
| 44 | Example 29 | 4-NH$_2$—Ph |
| 45 | Example 30 | 3-NH$_2$—Ph |
| 46 | Example 31 | 2-NH$_2$—Ph |

EXAMPLE 47

5-((N-Benzyloxycarbonyl)-Piperidin-4-YL)-3-(4-Fluorophenyl)-2-(4-Pyridyl)-Pyrrole

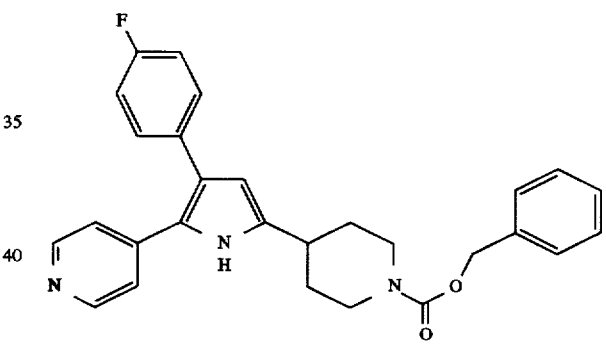

Step 1

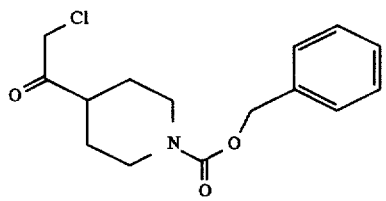

To a solution of N-benzyloxycarbonyl-piperidine-4 carboxylic acid (5.0 g (19 mmol)) in 20 ml of dry EtOAc at −15° C. was added 2.71 g (20.9 mmol) of diisopropylethylamine followed by 2.51 g (20.9 mmol) of isopropenylchloroformate. The reaction mixture was stirred for 1 hour and filtered through a dry sintered funnel into a dry 250 ml round bottom flask at 0C. The filtrate was treated with ethereal diazo methane (freshly prepared in the normal manner from 10 g of N-methylnitrosourea). The reaction mixture was stirred for 1 hour and then poured into 50 ml of water. The reaction mixture was extracted with ethyl acetate (3×50 ml).

The combined organic phases were washed with brine and dried over Na₂SO₄. The mixture was filtered and the filtrate was concentrated in vacuo. The residue was purified by flash chromatography over silica gel eluting with 50% EtOAc/hexanes to give the intermediate diazomethyl ketone. The material was dissolved in 20 ml of ether and cooled to 0° C. and then treated portionwise with 10 ml of 1 M HCl in ether. After 1 hour the reaction mixture was poured into 20 ml of saturated NaHCO₃ solution. The product was extracted with EtOAc (3×20 ml). The combined organic phases were washed with brine and dried over MgSO₄. The mixture was filtered and the filtrate was concentrated in vacuo. The residue was purified by flash chromatography over silica gel eluting with 30% EtOAc/hexanes to give the desired product.

H¹-NMR (CDCl₃, 300 MHz): 1.56 (m 2H); 1.85 (bm, 2H); 2.87 (m, 3H); 4.12 (s, 2H); 4.20 (bs, 1H); 5.12 (bs, 2H); 7.35 (m, 5H).

Step 2

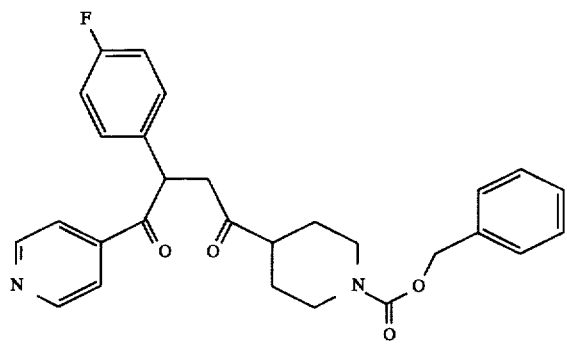

To a solution of the product of Preparative Example 3 (0.13 g (0.67 mmol)) in 1.5 ml of dry DMSO is added 0.74 ml (0.61 mmol) of a 1M solution of sodium hexamethyl disilazide in THF. After 10 minutes a solution of 0.19 g (0.67 mmol) of the product of Step 1 is added in 1 ml DMSO dropwise. The reaction mixture is stirred for 2 hours, diluted with ethyl acetate (20 ml) and washed with water (3×10 ml). The combined organic phases are washed with brine and dried over MgSO₄. The mixture is filtered and the filtrate is concentrated in vacuo. The residue is purified by MPLC over silica gel eluting with 2% MeOH/CH₂Cl₂ to give the desired product.

Step 3

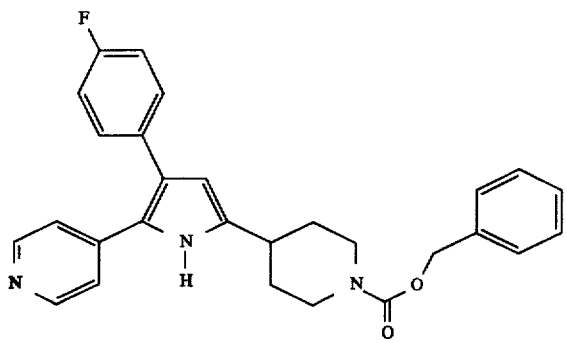

The product of Step 2 (0.13 g (0.29 mmol) is heated in 2 ml of acetic acid in the presence of 0.5 g ammonium acetate at 110° C. for 2 hours. The reaction mixture is diluted with EtOAc (10 mL) and washed with water. The combined organic phases are washed with brine and dried over MgSO₄. The mixture is filtered and the filtrate is concentrated in vacuo. The residue is purified by rotary chromatography over silica gel eluting with 5% MeOH/CH₂Cl₂ to give the desired product.

FAB ms: 456 (M+₊₁).

EXAMPLE 48

5-(N-Methyl Piperidin-4-YL)-3-(4-Fluorophenyl)-2-(4-Pyridyl)Pyrrole

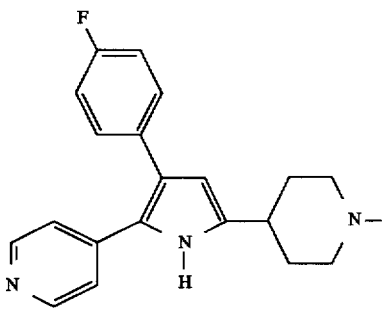

A solution of the product of Example 47 in THF at room temperature is treated with 2 equivalents of lithium aluminium hydride. The solution is refluxed for 2 hours, cooled to room temperature and treated with water, extracted with ethyl acetate and dried over sodium sulfate to give the desired product.

FAB ms: 336 (M+₊₁).

EXAMPLE 49

(Method 4)

5-(4-Chlorophenyl)-3-(Biphenyl)-2-(4-Pyridyl)Pyrrole

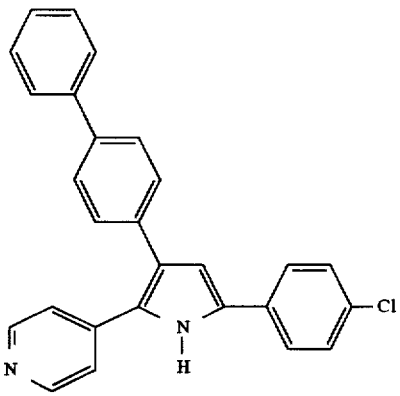

To a stirred solution of the bromo compound Example 37 (82 mg, 0.20 mmol) and benzene boronic acid (73 mg, 0.60 mmol) in toluene (5 InL) and EtOH (2.5 mL) was added 1.25 N-NaOH solution (0.82 mL). After the addition of Pd(0) (Ph₃P)₄ (4.6 mg, 0.004 mmol) the solution was degassed by pumping with a vacuum pump three times. The solution was stirred under nitrogen at 90° C. for 4 hrs. The product was extracted with EtOAc (3×), the combined organic phase was washed with brine and dried over anhydrous MgSO₄.

Concentration was followed by flash chromatography (H:E=1:1, 100% EtOAc) to give the desired product as a slightly yellow solid.

FAB ms: 407 (M+⁺¹).

EXAMPLES 50-61

Using the method disclosed in Example 49, the following compound were prepared using the compounds disclosed in Examples 37 and 34 as starting materials.

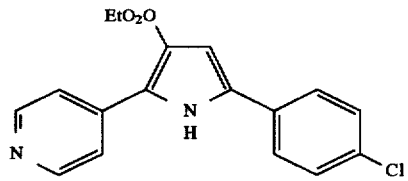

| Example # | R⁴ | Mass Spec. (M⁺ + 1) |
|---|---|---|
| 50 | 3-Ph—Ph— | 407 |
| 51 | 4-(4-MeO—Ph)—Ph— | 437 |
| 52 | 3-(4-MeO—Ph)—Ph— | 437 |
| 53 | 4-(4-CF$_3$—Ph)—Ph— | 475 |
| 54 | 4-(4-F—Ph)—Ph— | 425 |
| 55 | 4-(3-NO$_2$—Ph)—Ph— | 452 |
| 56 | 3-(3-NO$_2$—Ph)—Ph— | 452 |
| 57 | 4-(4-Me—Ph)—Ph— | 421 |
| 58 | 4-(2-thiophenyl)—Ph— | 413 |
| 59 | 4-(3-thiophenyl)—Ph— | 413 |
| 60 | 3-(2-thiophenyl)—Ph— | 413 |
| 61 | 3-(3-thiophenyl)—Ph— | 413 |

EXAMPLE 62

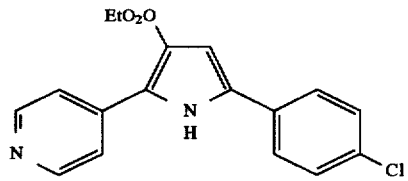

Step 1
Ethyl 3-(4-Pyridyl)-3-Oxo-Propionate

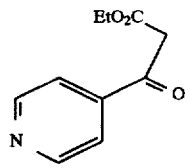

To a solution of 3.02 g of ethyl isonicotinoate in 10 ml of ethyl acetate under nitrogen was added 0.53 g (0.022 m) of 60% sodium hydride portionwise. The reaction mixture was heated to reflux for 3 hours, cooled and carefully dilted with 20 ml of water and was acidified with 5% citric acid solution. The aqueous phase was extracted with ethyl acetate. The organic extracts were washed with brine and dried over MgSO$_4$, filtered and concentrated in vacuo to give the crude product. The material was recrystallized from isopropanol to give the desired product.

H$^1$-NMR (CDCl$_3$, 300 MHz): keto form: 1.33 (t, 3H); 4.27 (q, 2H); 5.75 (s, 2H), 7.61 (dd, 2H); 8.72 (dd, 2H). enol form: 1.25 (t, 3H); 4.21 (q, 2H); 7.26 (s, 1H), 7.72 (dd, 2H); 8.83 (dd, 2H).

Step 2

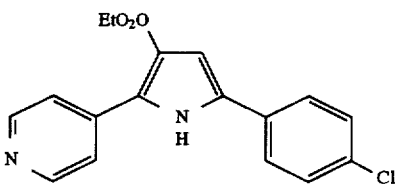

To a solution of 2.29 g (0.01 m) of the product of Step 1 in 75 ml of ethanol was added at 0° C. 4.14 ml (0.011 m) of a 21% wt solution of sodium ethoxide in ethanol. After 10 minutes 2.56 g (0.011 m) of 4-chloro-bromoacetophenone in ethanol was added. The reaction mixture was warmed to room temperature for 30 minutes and then heated at 70° C. for 2 hours. The mixture was allowed to age overnight at room temperature. The reaction mixture was acidified with 5% citric acid and diluted with water and extracted with ethyl acetate. The organic extracts were washed with brine and dried over MgSO$_4$, filtered and concentrated in vacuo to give the crude 1,4 diketone intermediate. The material was dissolved in 50 ml of acetic acid and heated with 5 grams of ammonium acetate until the starting material had been conxumed. The reaction mixture was diluted with ethyl acetate, washed with water and dried by washing with brine and standing over MgSO$_4$. The mixture was filtered and the filtrate was concentrated in vacuo. The crude product was purified by flash chromatography eluting with 5% MeOH/CH$_2$Cl$_2$.

H$^1$-NMR (CD$_3$OD, 300 MHz): 1.20 (t, 3H); 4.15 (q, 2H); 6.98 (s, 1H); 7.31 (d, 2H); 7.60 (d, 2H); 7.82 (bd, 2H); 8.50 (bs, 2H).

EXAMPLE 63

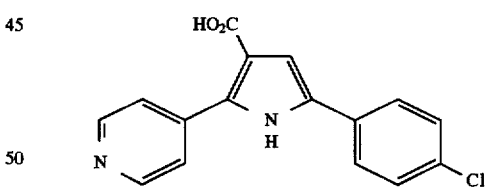

To a suspension of 1.85 g (5.67 mm) of the product of Example 62 in 25 ml of ethanol was added 25 ml of a 5% lithium hydroxide-solution. The solution was heated at reflux for 5 hours. The conversion of the starting material (rf 0.3 in 5% MeOH/CH$_2$Cl$_2$) to product (rf 0.05 in 5% MeOH/CH$_2$Cl$_2$) was monitored by TLC. The reaction mixture was diluted with water, filtered and acidified to give the desired acid.

H$^1$-NMR (CD$_3$OD, 300 MHz): 7.04 (s, 1H); 7.41 (d, 2H); 7.68 (d, 2H); 7.77 (d, 2H); 8.55 (bd, 2H).

EXAMPLE 64

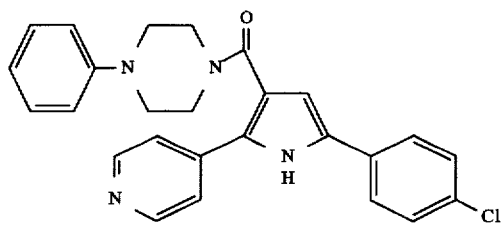

A solution of 0.05 g (0.16 mmol) of the product of Example 63 in 1 ml of DMF 0.025 g (0.16 mmol) of N-phenyl piperazine, 0.026 ml (0.25 mmol) of N-methyl morpholine, 0.032 g (0.24 mmol) of N-hydroxybenzotriazole and 0.045 g (0.24 mmol) of 1-ethyl-3-(3-dimethylaminopropyl)carbodiimide. The solution was stirred at room temperature over night and diluted with water. The aqueous phase was extracted with ethyl acetate. The organic phase was dried over $MgSO_4$, filtered and concentrated in vacuo. The residue was purified by rotory chromatography eluting with 4% $MeOH/CH_2Cl_2$ to provide the desired product.

FAB ms: C26H23N4ClO, calc=442; observed 443 ($M^+ + 1$).

EXAMPLES 65–69

The compounds in the following table were prepared utilizing the procedure disclosed in Example 64.

| Example | Compound | Notes/Mass Spec |
|---|---|---|
| 65 | | FAB ms: C28H27N4ClO, calc = 470; observed 471 ($M^+ + 1$) |
| 66 | | FAB ms: C28H20N3ClO, calc = 449; observed 450 ($M^+ + 1$) |
| 67 | | FAB ms: C26H26N3ClO, calc = 431; observed 432 ($M^+ + 1$) |
| 68 | | Coupling as above with benzyl alcohol, EDC and DMAP. FAB ms: C23H17N2ClO2, calc = 388; observed 389 ($M^+ + 1$) |

-continued

| Example | Compound | Notes/Mass Spec |
|---|---|---|
| 69 | 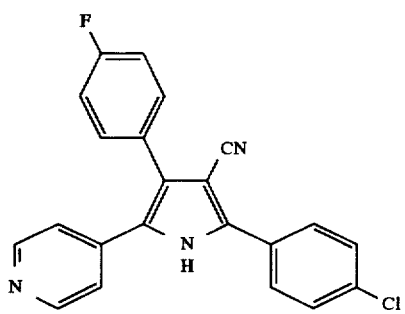 | Coupling as above with 2-phenyl-phenyl, EDC and DMAP. FAB ms: C28H19N2ClO2, calc = 450; observed 451 (M+ + 1) |

EXAMPLE 70

Step 1

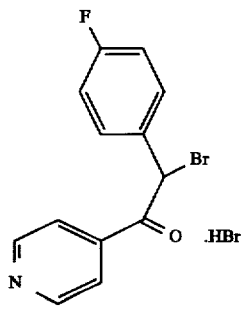

To a solution of 1.0 g (4.65 mmol) of Preparative Example 3 in 48% aqueous HBr was added bromine (0.89 g, 5.58 mmol) at room temperature. The reaction ixture was heated to 100° C. for 1 hour and then cooled to room temperature and allowed to stand 5 overnight. The resulting yellow precipitate was filtered, washed with acetone and dried in vacuo to provide the bromide.

Step 2

To a solution of 100 mg (0.27 mmol) of the product of Step 1 in 3 ml of DMF was added triethylamine. To this mixture was added a solution of the preformed sodium salt of 2-cyano-4'-chloroacetophenone (57.5 mg, 0.32 mmol). The reaction mixture was stirred at room temperature for 1 hour, concentrated in vacuo and was partitioned between EtOAc and water. The aqueous phase was extracted with EtOAc. The combined organic phases were washed with brine, dried over MgSO4 filtered and concentrated in vacuo. The residue was committed to the condensation with ammonium acetate as described previously to provide the desired product following purification by flash chromatography.

EXAMPLE 71

(Method 4a-1)

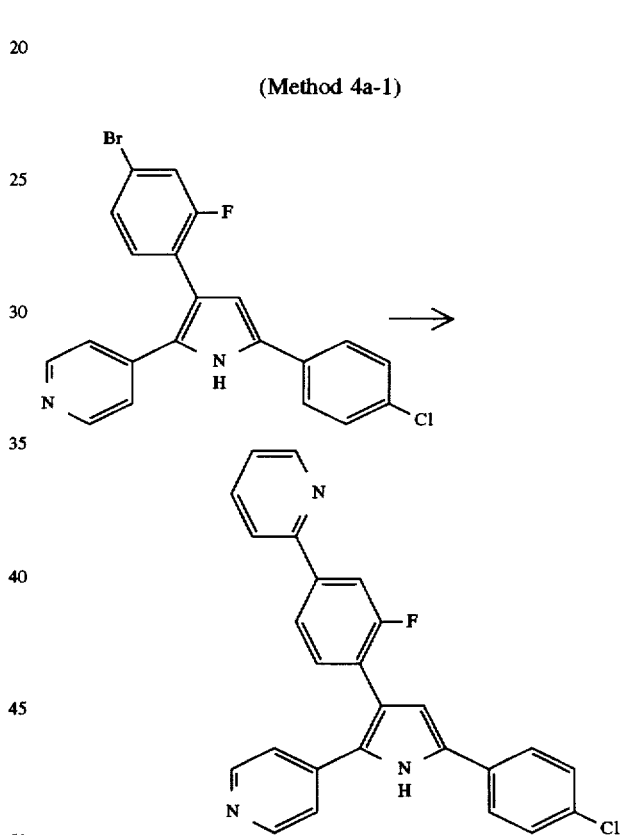

A solution of the compound of Example 39 in toluene was treated with 2 equivalents of 2-tributylstannyl pyridine and 5 mole % of tetrakistriphenylphosphine. The solution was heated to 100° C. and monitored by TLC for consumption of starting material. The reaction mixture was concentrated in vacuo and was purified by flash chromatography over silica gel eluting with an appropriate solvent to provide the desired product.

FAB ms: C26H17N3ClF1 calc=425 observed 426 (M++1).

EXAMPLE 72

(Method 4a-2)

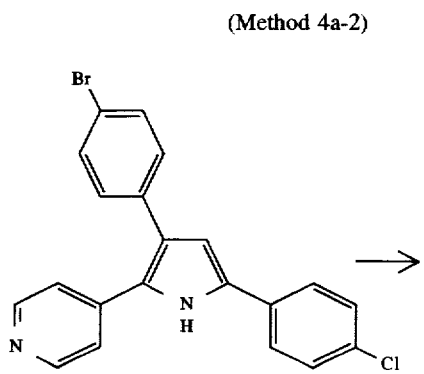

Step 1

A solution of the compound of Example 37 in dioxane was heated with hexabutylditin in the presence of 5 mole % tetrakistriphenylphosphine at 80° C. until the starting material had been consumed as determined by TLC. The reaction mixture was concentrated in vacuo and purified by flash chromatography over silica gel eluting with 1:1 EtOAc/hexanes to provide the desired intermediate.

$^1$H-NMR (CDC13–400 MHz): 0.31 (s, 9H); 6.64 (dd, 1H); 7.26 (m, 2H); 7.36 (t, 4H); 7.50 (t, 4H); 8.49 (dd, 2H); 8.65 (bs, 1H).

Step 2

The product of Step 1 was combined with 3 equivalents of the requisite anhydride, and 5 mole % tetrakistriphenylphosphine in toluene at 100° C., and was heated until the starting material had been consumed. The reaction mixture was concentrated in vacuo and purified by flash chromatography over silila gel eluting to provide the desired product.

EXAMPLE 73–81

(Method 5)

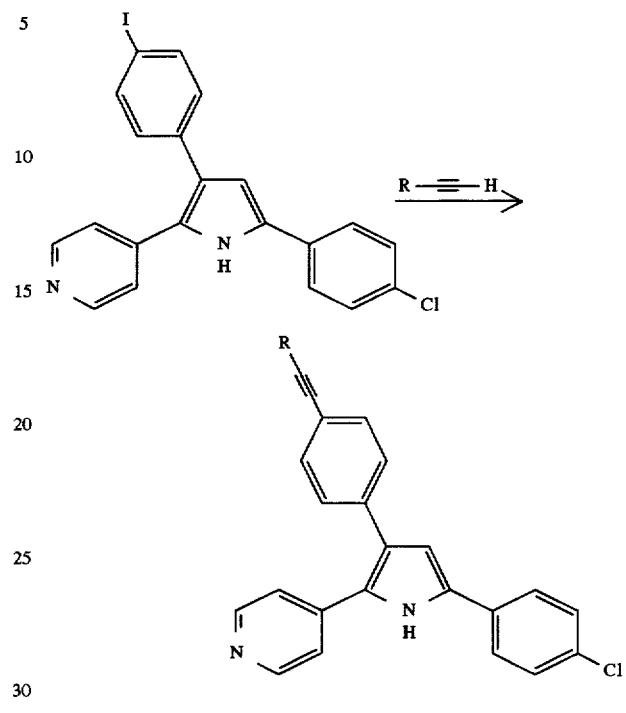

A solution of 3-(4-iodophenyl)-5-(4-chlorophenyl)-2-(4-pyridyl)pyrrole, prepared via method 2, in piperidine was treated with 2–3 equivalents of an acetylene, 5 mole % tetrakistriphenylphosphine, 5 mole % cuprous iodide and 5 mole % triphenylphosphine. The reaction mixture was degassed and then heated at 1000° C. for 4.5 hours. The reaction mixture was concentrated in vacuo and was purified by flash chromatography over silica gel eluting with an appropriate solvent to provide the desired product.

The following compounds were prepared by the methods described above.

TABLE

| Expl. No. | R | FAB ms | Method |
|---|---|---|---|
| 73 | H | 355 | 4b* |
| 74 | phenyl | 431 | 5 |
| 75 | n-butyl | 411 | 5 |
| 76 | 4-methyl-phenyl | 445 | 5 |
| 77 | 4-Cl-phenyl | 465 | 5 |
| 78 | 2-pyridyl | 432 | 5 |

TABLE-continued

[Structure: pyrrole with R-substituted phenylacetylene at 3-position, 3-pyridyl at 2-position (N-H), and 4-chlorophenyl at 5-position]

| Expl. No. | R | FAB ms | Method |
|---|---|---|---|
| 79 | 4-F-phenyl | 449 | 5 |
| 80 | 4-ethylphenyl | 459 | 5 |
| 81 | 4-butylphenyl | 487 | 5 |

*Coupled with trimethylsilyl acetylene followed by treatment with tetrabutyl amonium fluoride.

EXAMPLES 82–289

The following compounds were prepared using the described above.

TABLE

[Structure: pyrrole with R$^4$ at 3-position, 3-pyridyl at 2-position (N-H), and R$^2$ at 5-position]

| Expl. No. | R² | R⁴ | FAB ms | Method | Ntes |
|---|---|---|---|---|---|
| 82 | 4-(COOH)-Ph | 4-F-Ph | 358.1 | 6 | 1 |
| 83 | 4-Cl-Ph | 4-(3-(i-Bu)-6-(SO₂NH-t-Bu)-phenyl)-Ph | 598 | 4 | |
| 84 | 4-Cl-Ph | 4-(4-(n-Bu)-phenyl-Ph | 463 | 4 | |
| 85 | 4-Cl-Ph | 4-(3-(iBu)-6-(SO₂NH₂)-phenyl)-Ph | 542 | 6 | 2 |
| 86 | 4-Cl-Ph | 3-(4-(n-Bu)-phenyl)-Ph | 463 | 4 | |
| 87 | 4-Cl-Ph | 4-(5-(n-Bu)-thiophenyl)-Ph | 469 | 4 | |
| 88 | 4-Cl-Ph | 2-(F)-4-(5-(n-Bu)-thiophen-2-yl)-Ph | 487 | 4 | |
| 89 | 4-Cl-Ph | 3,5-di-Br-Ph | 475 | 3 | |
| 90 | 4-Cl-Ph | 3,5-(thiophen-2-yl)-Ph | 495 | 4 | |
| 91 | 4-Cl-Ph | 3,4-di-(4-OMe-Ph)-Ph | 543 | 4 | |
| 92 | 4-Cl-Ph | 3,5-di-(4-Me-Ph)-Ph | 511 | 4 | |
| 93 | 4-Cl-Ph | 4-(OCH₂CO₂Me)-Ph | 419.3 | 3 | |
| 94 | 4-Cl-Ph | 4-OMe-Ph | 375.1 | 3 | |
| 95 | 4-Cl-Ph | 4-i-Pr-Ph | 373.2 | 3 | |
| 96 | 4-Cl-Ph | 4-OBzl-Ph | 437.1 | 3 | |
| 97 | 4-Cl-Ph | 5-Ph-thiazol-2-yl | 414.2 | 3 | |
| 98 | 4-Cl-Ph | 4-Br-thiophen-2-yl | 417.1 | 3 | |

TABLE-continued

[Structure: pyrrole with R$^4$ at 3-position, 3-pyridyl at 2-position (N-H), and R$^2$ at 5-position]

| Expl. No. | R² | R⁴ | FAB ms | Method | Ntes |
|---|---|---|---|---|---|
| 99 | 4-Cl-Ph | 2-OPr-Ph | 389.2 | 3 | |
| 100 | 4-Cl-Ph | 3-thiophenyl | 337.1 | 3 | |
| 101 | 4-Cl-Ph | 3,5-di-(3-nitrophenyl)-Ph | 573 | 4 | |
| 102 | 4-Cl-Ph | 4-(benzofuran-2-yl)-phenyl | 447 | 4 | |
| 103 | 4-Cl-Ph | 3-Br-5-(thiophen-2-yl)-Ph | 493 | 4 | |
| 104 | 4-Cl-Ph | 4-(5-Cl-thiophen-2-yl)-Ph | 447 | 4 | |
| 105 | 4-Cl-Ph | 4-(3,5-di-CF₃-Ph)-Ph | 543 | 4 | |
| 106 | 4-Cl-Ph | 4-(2-OMe-Ph)-Ph | 437 | 4 | |
| 107 | 4-Cl-Ph | 4-(4-Cl-Ph)-Ph | 441 | 4 | |
| 108 | 4-Cl-Ph | 4-(CO₂Me)-Ph | 389 | 2 | |
| 109 | 4-Cl-Ph | 2-F-4-(thiophen-2-yl)-Ph | 431 | 4 | |
| 110 | 4-Cl-Ph | 4-(3-(NH₂)-Ph)-Ph | 422 | 4 | |
| 111 | 4-Cl-Ph | 4-(3-(OMe)-Ph)-Ph | 437 | 4 | |
| 112 | 4-Cl-Ph | 2-Br-Ph | 411 | 2 | |
| 113 | 4-Cl-Ph | 2,6-di-F-Ph | 367 | 2 | |
| 114 | 4-Cl-Ph | 3-OBnzl-Ph | 437.1 | 3 | |
| 115 | 4-Cl-Ph | 4-(trans-ethenyl-Ph)-Ph | 433.1 | 3 | |
| 116 | 4-Cl-Ph | 9-phenanthrenyl | 431.1 | 3 | |
| 117 | 4-Cl-Ph | 3-(OPh)-Ph | 423.0 | 3 | |
| 118 | 4-Cl-Ph | 2-(OMe)-Ph | 361.1 | 3 | |
| 119 | 2,4-di-Cl-Ph | 4-F-Ph | 383.0 | 2 | |
| 120 | t-Bu | 4-F-Ph | 295.2 | 2 | |
| 121 | Me | 4-F-Ph | 253.1 | 2 | |
| 122 | 4-Cl-Ph | 4-CN-Ph | 356 | 3 | |
| 123 | 4-Cl-Ph | 2,4-di-F-Ph | 367 | 2 | |
| 124 | 4-Cl-Ph | 2,4,6-tri-F-Ph | 385 | 2 | |
| 125 | 4-Cl-Ph | 2-(3-OMe-Ph)-Ph | 437 | 4 | |
| 126 | 4-Cl-Ph | 2-(3-NO₂-Ph)-Ph | 452 | 4 | |
| 127 | 4-Cl-Ph | 2-thiophen-2-yl-Ph | 413 | 4 | |
| 128 | 4-Cl-Ph | 2-indolyl | 370.1 | 3 | |
| 129 | 4-Cl-Ph | 2-OEt-Ph | 375.1 | 3 | |
| 130 | 4-Cl-Ph | 2-OH-5-Br-Ph | 425.7 | 3 | |
| 131 | 4-Cl-Ph | 2-OMe-5-Br-Ph | 441.0 | 3 | |
| 132 | 4-Cl-Ph | 5-(2-(CO₂Me)-thiophen-3-yl)-furan-2-yl | 461.1 | 3 | |
| 133 | 4-Cl-Ph | 2,5-di-OMe-Ph | 391.1 | 3 | |
| 134 | 3-Cl-Ph | 4-F-Ph | 349.1 | 2 | |
| 135 | 4-F-Ph | 4-F-Ph | 393.0 | 3 | |
| 136 | 4-Cl-Ph | 4-(tetrazol-5-yl)-Ph | 399 | 6 | a |
| 137 | 4-F-Ph | 4-(thiophen-2-yl)-Ph | 397.0 | 5 | |
| 138 | 2-F-Ph | 4-F-Ph | 333.1 | 2 | |
| 139 | 4-Cl-Ph | 2-F-4-(2-(5-Cl-thiophen-2-yl)-Ph | 465 | 4 | |
| 140 | 4-Cl-Ph | 4-(CONH-t-Bu)-Ph | 430 | 6 | 3 |
| 141 | 2-OMe-4-Cl-Ph | 4-F-Ph | 379.1 | 2 | |
| 142 | 4-Cl-Ph | 4-(N- | 413 | 6 | b |

TABLE-continued

Structure: pyrrole with 3-pyridyl at position 2, R² at position 5, R⁴ at position 3, NH.

| Expl. No. | R² | R⁴ | FAB ms | Method | Ntes |
|---|---|---|---|---|---|
| | | methyltetrazolyl)-Ph | | | |
| 143 | 4-Cl-Ph | 2-Cl-4-Br-Ph | 444 | 3 | |
| 144 | 4-Cl-Ph | 4-(CO₂Et)-Ph | 403 | 3 | |
| 145 | 4-N-acetyl-piperidinyl | 4-F-Ph | 364.1 | 6 | 4 |
| 146 | 4-N-(methoxy-carbonyl)-piperidinyl | 4-F-Ph | 380.1 | 6 | 5 |
| 147 | 4-N-(isopropoxy-carbonyl)-piperidinyl | 4-F-Ph | 408.1 | 6 | 5 |
| 148 | 4-piperidinyl | 4-F-Ph | 322.1 | 6 | 6 |
| 149 | 4-Cl-Ph | 2-ethoxy-5-Br-Ph | 453.0 | 3 | |
| 150 | 4-Cl-Ph | 2,5-di-F-Ph | 367.0 | 3 | |
| 151 | 4-Cl-Ph | 2-(3-Cl-propoxy)-Ph | 423.0 | 3 | |
| 152 | 4-Cl-Ph | 2-propoxy-5-Br-Ph | 469.0 | 3 | |
| 153 | 4-Cl-Ph | 2-F-5-Br-Ph | 429.0 | 3 | |
| 154 | 4-Cl-Ph | 4-C(O)N(Bzl)₂-Ph | 554 | 6 | 3 |
| 155 | 4-Cl-Ph | 4-(3-Pyr)-Ph | 408 | 4 | |
| 156 | 4-Cl-Ph | 4-(C(O)-(N-Boc-piperazinyl))-Ph | 543 | 6 | 3 |
| 157 | 4-Cl-Ph | 4-(C(O)NPh₂)-Ph | 514 | 6 | 3 |
| 158 | 4-Cl-Ph | 4-(C(O)-morpholinyl)-Ph | 444 | 6 | 3 |
| 159 | 4-Cl-Ph | 4-(C(O)-L-proline-O-(t-Bu))-Ph | 528 | 6 | 3 |
| 160 | 4-Cl-Ph | 4-C(O)-spiroindene)-phenyl | 542 | 6 | 3 |
| 161 | 4-Cl-Ph | 4-(5-Me-1,3,4-oxadiazol-2-yl)-Ph | 413 | 6 | 7 |
| 162 | 4-Cl-Ph | 4-(5-(n-Bu)-1,3,4-oxadiazol-2-yl)-Ph | 455 | 6 | 8 |
| 163 | 4-Cl-Ph | trans-ethenyl-Ph | 357.0 | 3 | |
| 164 | 4-Cl-Ph | 2-(t-CHCH-Ph)-Ph | 433.0 | 3 | |
| 165 | 4-Cl-Ph | 2-(OBzl)-Ph | 437.0 | 3 | |
| 166 | 4-Cl-Ph | 2-(O-(n-hexyl))-Ph | 431.1 | 3 | |
| 167 | 4-Cl-Ph | 2-(O-(n-nonyl))-Ph | 473.1 | 3 | |
| 168 | 4-Cl-Ph | 2-(O-iPr)-Ph | 389.2 | 3 | |
| 169 | 4-Cl-Ph | 2-(O-iBu)-Ph | 403.2 | 3 | |
| 170 | 4-Cl-Ph | 2-(O-(n-butyl))-Ph | 403.2 | 3 | |
| 171 | 4-Cl-Ph | 2-(O-allyl)-Ph | 387.1 | 3 | |
| 172 | 4-Cl-Ph | 2-(OCH₂-(2,6-di-Cl-Ph))-Ph | 504.9 | 3 | |
| 173 | 4-Cl-Ph | 4-(2-pyr)-Ph | 408 | 4 | |
| 174 | 4-Cl-Ph | 4-(2-(SO₂NH-(t-Bu))-Ph)-2-F-Ph | 560 | 4 | |
| 175 | 4-Cl-Ph | 4-NO₂-Ph | 376 | 3 | |
| 176 | c-hexyl | 4-F-Ph | 321.1 | 2 | |
| 177 | N-(CBzl)-piperidin-4-yl | CO₂Et | 434.1 | 2 | |
| 178 | 4-Cl-Ph | 4-NH₂-Ph | 346 | 6 | 9 |
| 179 | 4-Cl-Ph | 4-(NHCO₂-(n-butyl))-Ph | 446 | 6 | 10 |
| 180 | 4-Cl-Ph | 4-(NHSO₂-(n-butyl))-Ph | 466 | 6 | 10 |
| 181 | 4-Cl-Ph | 4-(NHSO₂-thiophen-2-yl)-Ph | 492 | 6 | 10 |
| 182 | 4-Cl-Ph | 2-(OC(O)-propyl)-Ph | 417.1 | 3 | |
| 183 | 4-Cl-Ph | 2-(O(CH₂)₃SMe)-Ph | 447.2 | 3 | |
| 184 | 4-Cl-Ph | 4-(NHCO₂Bzl)-Ph | 481 | 6 | 10 |
| 185 | 4-Cl-Ph | 4-(NHCO₂Ph)-Ph | 466 | 6 | 10 |
| 186 | N-(COOCH₂Ph-4-Cl)-piperidin-4-yl | 4-F-Ph | 490.2 | 6 | 5 |
| 187 | N-(COOCH₂Ph-4-Br)-piperidin-4-yl | 4-F-Ph | 536.1 | 6 | 5 |
| 188 | N-(COOCH₂Ph-4-Ph)-piperidin-4-yl | 4-F-Ph | 532.3 | 6 | 5 |
| 189 | N-(COOCH₂Ph-4-NO₂)-piperidin-4-yl | 4-F-Ph | 501.2 | 6 | 5 |
| 190 | N-(COOCH₂Ph-3-Cl)-piperidin-4-yl | 4-F-Ph | 490.2 | 6 | 5 |
| 191 | N-(COOCH₂Ph-2,4,5-tri-OMe)-piperidin-4-yl | 4-F-Ph | 561.3 | 6 | 5 |
| 192 | N-(COOCH₂Ph-2-Cl)-piperidin-4-yl | 4-F-Ph | 490.2 | 6 | 5 |
| 193 | 4-NHCO₂Bzl-cyclohexyl | 4-F-Ph | 470.2 | 2 | |
| 194 | N-(COOCH₂Ph)-piperidin-3-yl | 4-F-Ph | 456.2 | 2 | |
| 195 | 4-NH₂-cyclohexyl | 4-F-Ph | 336.1 | 6 | 11 |
| 196 | piperidin-3-yl | 4-F-Ph | 322.3 | 6 | 12 |
| 197 | 4-Cl-Ph | 2-OH-Ph | 347.2 | 3 | |
| 198 | 4-Cl-Ph | 2-(4-Cl-SPh)-Ph | 473.0 | 3 | |
| 199 | 4-Cl-Ph | 2-OPh-Ph | 423.1 | 3 | |
| 200 | 4-Cl-Ph | 2-(O(CH₂)₃OMe)-Ph | 419.2 | 3 | |
| 201 | 4-Cl-Ph | 2-(OCONMe₂)-Ph | 418.2 | 3 | |
| 202 | 4-Cl-Ph | 2-(S-t-Bu)-Ph | 419.1 | 3 | |
| 203 | 4-Cl-Ph | 4-(O(n-Pr))-Ph | 389.8 | 3 | |
| 204 | 4-Cl-Ph | 2-(O(n-Pr))-4-(Br)-Ph | 469.1 | 3 | |

TABLE-continued

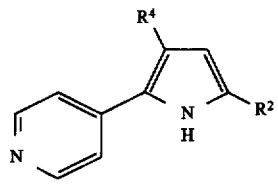

| Expl. No. | R² | R⁴ | FAB ms | Method | Ntes |
|---|---|---|---|---|---|
| 205 | 4-Cl-Ph | 4-(5-((CH₂)₄OH)-thiophen-2-yl)-Ph | 485 | 6 | 13 |
| 206 | 4-Cl-Ph | 4-(5-((CH₂)₄-azido)-thiophen-2-yl)-Ph | 510 | 6 | 14 |
| 207 | 4-Cl-Ph | 4-(3-OMe-Ph)-2-(O(n-Pr))-Ph | 495.2 | 4 | |
| 208 | 4-Cl-Ph | 3-(O(n-Pr))-Ph | 389.2 | 3 | |
| 209 | 4-Cl-Ph | 4-(3-NH₂-Ph)-2-(O(n-Pr))-Ph | 480.2 | 3 | |
| 210 | 4-Cl-Ph | benzyl | 345 | 2 | |
| 211 | 4-Cl-Ph | 2-(furan-2-yl)-Ph | 397 | 4a-1 | |
| 212 | 4-Cl-Ph | 4-(furan-2-yl)-Ph | 397 | 4a-1 | |
| 213 | 4-Cl-Ph | 4-(2-OH-5-Br-Ph)-2-(O(n-Pr))-Ph | 561.2 | 4 | |
| 214 | 4-Cl-Ph | 4-(5-((n-Bu))-thiophen-2-yl)-2-(O(n-Pr))-Ph | 527.3 | 4 | |
| 215 | 4-Cl-Ph | 4-(3-(O(n-Bu))-Ph)-Ph | 479 | 4a-2 | |
| 216 | 4-Cl-Ph | 4-(5-((CH₂)4-amino)-thiophen-2-yl)-Ph | 484 | 6-1c | 15 |
| 217 | 4-Cl-Ph | 4-((n-Bu))-thiophen-2-yl)-Ph | 469 | 4 | |
| 218 | 4-Cl-Ph | 1-naphthyl | 381.1 | 3 | |
| 219 | 4-Cl-Ph | quinolin-8-yl | 582.1 | 3 | |
| 220 | 4-Cl-Ph | 4-(2-(OMe)-5-Br-Ph)-2-(O(n-Pr))-Ph | 575.1 | 4 | |
| 221 | 4-Cl-Ph | 4-(cyclohexyl)-Ph | 413 | 3 | |
| 222 | 4-Cl-Ph | 4-(n-Bu)-Ph | 387 | 3 | |
| 223 | 4-Cl-Ph | 4-(5-(NO₂)-thiophen-2-yl)-Ph | 458 | 4a-2 | |
| 224 | 4-Cl-Ph | 4-(3-(Me)-thiophen-2-yl)-Ph | 427 | 4a-2 | |
| 225 | 4-Cl-Ph | 4-(2,5-di-OMe-Ph)-Ph | 467 | 4a-2 | |
| 226 | 4-Cl-Ph | 4-(2,4,6-tri-Me-Ph)-Ph | 449 | 4 | |
| 227 | 4-Cl-Ph | 4-(5-ethyl-thiophen-2-yl)-Ph | 441 | 4 | |
| 228 | 4-Cl-Ph | 4-(5-Me-thiophen-2-yl)-Ph | 427 | 4a-2 | |
| 229 | 4-Cl-Ph | 4-(5-(n-Pr)-thiophen-2-yl)-Ph | 455 | 4 | |
| 230 | 4-Cl-Ph | 4-(4-(n-Pr)-Ph)-Ph | 449 | 4a-2 | |
| 231 | 4-Cl-Ph | 4-I-Ph | 457 | 2 | |
| 232 | 4-Cl-Ph | 4-(5-OMe-pyridin-2-yl)-Ph | 438 | 4 | |
| 233 | 4-Cl-Ph | 4-(3-Me-Ph)-Ph | 421 | 4a-2 | |
| 234 | 4-Cl-Ph | 4-(3,4-(methylenedioxy)-Ph)-Ph | 451 | 4 | |
| 235 | 4-Cl-Ph | 4-(3-(propoxy)-Ph)-Ph | 465 | 4a-2 | |
| 236 | 4-Cl-Ph | 4-(3-acetyl-Ph)-Ph | 449 | 4a-2 | |
| 237 | 4-Cl-Ph | 4-(3-NO₂-4-Me-Ph)-Ph | 466 | 4a-2 | |
| 238 | 4-Cl-Ph | 4-(3,4-di-OMe-Ph)-Ph | 467 | 4a-2 | |
| 239 | 4-Cl-Ph | 4-(3-(OCH₂CH₂OMe)-Ph)-Ph | 481 | 4a-2 | |
| 240 | 4-Cl-Ph | 4-(4-CN-3-Me-Ph)-Ph | 446 | 4a-2 | |
| 241 | 4-Cl-Ph | 4-(5-acetyl-thiophen-2-yl)-Ph | 455 | 4a-2 | |
| 242 | 4-Cl-Ph | CH₂CH₂-Ph | 359.2 | 3 | |
| 243 | 4-Cl-Ph | CH₂CH(Me)-Ph | 373.2 | 3 | |
| 244 | 4-Cl-Ph | CH(Me)CH₂-(3,4-(methylenedioxy)-Ph) | 417.2 | 3 | |
| 245 | 4-Cl-Ph | 4-(3-(OCH₂CH₂OEt)-Ph)-Ph | 495 | 4a-2 | |
| 246 | 4-Cl-Ph | 4-(indan-1-on-5-yl)-Ph | 461 | 4a-2 | |
| 247 | 4-Cl-Ph | 4-(4-Et-Ph)-Ph | 435 | 4 | |
| 248 | 4-Cl-Ph | 4-(5-CO₂Et-furan-2-yl)-Ph | 469 | 4a-2 | |
| 249 | 4-Cl-Ph | 4-(2-ethyl-phenyl)-Ph | 435 | 4a-2 | |
| 250 | 4-Cl-Ph | 2,4-di-propoxy-Ph | 447.1 | 3 | |
| 251 | 4-Cl-Ph | 2-propoxy-5-F-Ph | 407.1 | 3 | |
| 252 | 4-Cl-Ph | 3,5-di-Br-2-propoxy-Ph | 547.0 | 3 | |
| 253 | 4-Cl-Ph | 2-propoxy-5-Cl-Ph | 423.1 | 3 | |
| 254 | 4-Cl-Ph | 2-propoxy-3-Cl-Ph | 423.0 | 3 | |
| 255 | 4-Cl-Ph | 2-propoxy-3-F-Ph | 507.1 | 3 | |
| 256 | 4-Cl-Ph | 4-(5-pyrimidinyl)-Ph | 409 | 4a-2 | |

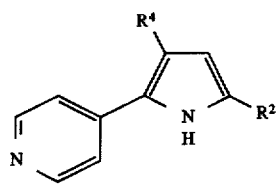

TABLE-continued

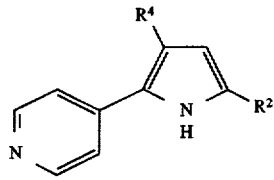

| Expl. No. | R² | R⁴ | FAB ms | Method | Ntes |
|---|---|---|---|---|---|
| 257 | 4-Cl-Ph | cyclohexyl | 357 | 3 | |
| 258 | 2-Br-Ph | 4-F-Ph | 393 | 3 | |

1. By hydrolysis of the compound of Example 32.
2. Treated the compound of Example 83 with TFA/$CH_2Cl_2$.
3. Saponification of the compound of Example 108 followed by EDC coupling with an amine.
4. EDC coupling of acetic acid with the compound of Example 148.
5. Acylation of the compound of Example 148.
6. Reduction of the compound of Example 47 with $H_2$, 10% Pd/C.
7. Example 144 refluxed with excess $NH_2NH_2$, for 1 hr, concentrated in vacuo, heated with trimethyl orthoacetate at 120° C. for 17 hrs.
8. Example 144 refluxed with excess $NH_2NH_2$, for 1 hr, concentrated in vacuo, heated with triethyl orthobutyrate at 120° C. for 17 hrs.

TABLE-continued

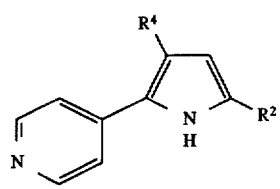

| Expl. No. | R² | R⁴ | FAB ms | Method | Ntes |
|---|---|---|---|---|---|

9. Example 175, $H_2$, 10% Pd/C.
10. Acylation or sulphonylation of the compound of Example 178.
11. Catalytic hydrogenation of Example 193.
12. Catalytic hydrogenation of Example 194.
13. Following Stille coupling of Example 37 followed by treatment with tetrabutyl ammonium fluoride in THF.
14. Treatment of Example 205 with mesyl chloride, pyridine, 0° C., followed by $NaN_3$, DMF, 25° C., 17 hrs.
15. Example 206, triphenylphosphine, $H_2O$.

a Treatment of Example 122 with $Me_3SnN_3$.

b Treatment of Example 136 with MeI and $Et_3N$.

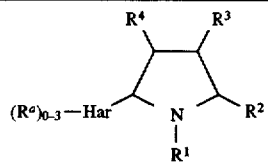

| Ex. | R¹ | (Rᵃ)₀₋₃-Har | R⁴ | R³ | R² | FAB ms | Method | Nts |
|---|---|---|---|---|---|---|---|---|
| 259 | H | 3-Pyr | 4-F—Ph | H | 4-Cl-Phenyl | 349 | 2 | |
| 260 | H | 2-furoyl | 4-Pyr | H | Phenyl | 287.2 | 3 | |
| 261 | H | 2-Pyr | 4-Pyr | H | Phenyl | 298.2 | 3 | |
| 262 | H | 3-quinolinyl | 4-Pyr | H | Phenyl | 348.0 | 3 | |
| 263 | H | 3-Pyr | 4-Pyr | H | Phenyl | 298.1 | 3 | |
| 264 | H | 4-Pyr | 4-F—Ph | Br | 4-Cl-Phenyl | 429.0 | 3 | |
| 265 | H | 4-Pyr | 4-F—Ph | Cl | 4-Cl—Ph | 383.1 | 3 | |
| 266 | H | 4-quinolinyl | 4-F—Ph | H | 4-Cl—Ph | 399 | 3 | |
| 267 | H | 4-(2-F)-pyr | 4-F—Ph | H | 4-Cl—Ph | 367 | 3 | |
| 268 | H | 3-F-4-pyr | 4-F—Ph | H | 4-Cl—Ph | 367 | 3 | |
| 269 | H | 3-(Me)-4-pyridyl | 4-F—Ph | H | 4-Cl—Ph | 363 | 3 | |
| 270 | H | 4-(2-Me)-pyridyl | 4-F—Ph | H | 4-Cl—Ph | 363 | 3 | |
| 271 | 2-OH—Ph | 4-pyr | 2-F-4-Br—Ph | H | 4-Cl—Ph | 520 | 2 | |
| 272 | H | 4-pyr | 4-F—Ph | Me | 4-Cl—Ph | 363 | 2 | |
| 273 | H | 4-Pyr | 4-F—Ph | Et | 4-Cl—Ph | 377 | 2 | |
| 274 | H | 4-Pyr | 4-F—Ph | Ph | 4-Cl—Ph | 425 | 2 | |
| 275 | H | 2-NH₂-pyridin-4-yl | 4-F—Ph | H | 4-Cl—Ph | 364.1 | 6 | a |
| 276 | H | pyrimidin-4-yl | 4-F—Ph | H | 4-Cl—Ph | 350.1 | 3 | |
| 277 | H | quinolin-6-yl | 4-F—Ph | H | 4-Cl—Ph | 399 | 3 | |
| 278 | H | 2-F-pyridin-5-yl | 4-F—Ph | H | 4-Cl—Ph | 367.1 | 3 | |
| 279 | H | 4-Pyr | 3-CF₃—Ph | Me | N-methyl- | 374 | 2 | |

-continued

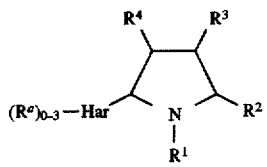

| Ex. | R¹ | (Rᵃ)₀₋₃-Har | R⁴ | R³ | R² | FAB ms | Method | Nts |
|---|---|---|---|---|---|---|---|---|
| 280 | H | 4-Pyr | 3-CF₃—Ph | Me | piperidin-4-yl piperidin-4-yl | 388 | 2 | |
| 281 | H | 2-OH-pyridin-5-yl | 4-F—Ph | H | 4-Cl-Ph | 365 | 6 | b |
| 282 | H | pyridazin-4-yl | 4-F—Ph | H | 4-Cl—Ph | 350 | 3 | |
| 283 | H | 4-Pyr | 4-F—Ph | H | 2-CN—Ph | 340 | 6 | d |
| 284 | H | 4-Pyr | 2-CN—Ph | H | 4-Cl—Ph | 356 | 6 | e |
| 285 | H | 4-Pyr | 4-F—Ph | n-Bu | 4-Cl—Ph | 405 | 2 | |
| 286 | H | 4-Pyr | 2-propoxy-4-(2-Ph ethynyl)-Ph | H | 4-Cl—Ph | 490 | 5 | c |
| 287 | H | 4-Pyr | 4-(2-propenyl)-cyclohexen-1-yl | H | 4-Cl—Ph | 375 | 3 | |
| 288 | H | 4-Pyr | N-(Cbz)-piperidin-4-yl | H | 4-Cl-Ph | 472 | 3 | |
| 289 | H | 4-Pyr | i-Propyl | H | 4-Cl—Ph | 297 | 3 | | a Part a: Example 267, MeOPhCH₂NH₂, 150° C. Part b: TFA/CH₂Cl₂
b Heating compound no. 278 in acetic acid at 100° C.
c Coupling of compound 204 with phenylacetylene.
d Coupling of compound 258 with ZnCN₂ and Pd(PPh₃)₄
e Coupling of compound 112 with ZnCN₂ and Pd(PPh3)4.

BIOLOGICAL ASSAYS

The ability of compounds of the present invention to inhibit the binding of glucagon and the synthesis or the activity of cytokines can be determined by the following in vitro assays.

$^{125}$I-Glucagon Binding Screen with CHO/hGLUR Cells

The reagents are prepared as follows:
1 M o-Phenanthroline (Aldrich #32,005-6, MW 198.23) (prepare fresh): 198.2 mg/ml ethanol
0.5 M DTT (Sigma #D-9779, MW 154.2)(prepare fresh).
Protease Inhibitor Mix(1000X): 5 mg leupeptin+10 mg benzamidine+40 mg bacitracin+5 mg soybean trypsin inhibitor per ml DMSO. Store aliquots at −20° C.
250 µM Human Glucagon (Peninsula #7165, MW 3480.62) :Solubilize 0.5 mg vial in 575 µl 0.1N acetic acid. Store in aliquots at −20° C. Thus, 1 µl yields 1 µM final concentration in assay for non-specific binding.
Assay Buffer: 20 mM Tris, pH 7.8; 1 mM DTT; 3 mM o-phenanthroline.
Assay Buffer w/ 0.1% BSA (for dilution of label only, therefore 0.01% final in assay): 10 µl 10% BSA (heat-inactivated)+990 µl assay buffer
$^{125}$I-Glucagon (NEN #NEX-207, receptor-grade, 2200Ci/mmol): Dilute to 50,000 cpm125 µl in assay buffer w/ BSA.Thus, ~50 pM final concentration in assay.

Harvesting of CHO/hGLUR Cells for Assay

1. Remove media from confluent flask then rinse once each with PBS (Ca,Mg-free) and Enzyme-free Dissociation Fluid (Specialty Media, Inc.).
2. Add 10 ml Enzyme-free Dissoc. Fluid and hold for ~4min. at 37° C.
3. Gently tap cells free, triturate, take aliquot for counting and centrifuge remainder for 5 min. at 1000 rpm.
4. Resuspend pellet in assay buffer (no BSA!) at 75000 cells per 100 µl.

Alternatively, membrane preparations from CHO/hGLUR cells can be used in place of whole cells at the same assay volume. Final protein concentration of membrane preparation is determined on a per batch basis.

The determination of inhibition of glucagon binding is carried out by measuring the reduction of I$^{125}$-glucagon binding in the presence of compounds of Formula I. The assay is carried out in a 96-well box. The following reagents are combined:

| | Assay Buffer | Compound/ Vehicle | 250 uM Glucagon | $^{125}$I-Glucagon | CHO/hGLUR Cells |
|---|---|---|---|---|---|
| Total Binding | 120 µL | —/5 µL | — | 25 µL | 100 µL |
| + compound | 120 µL | 5 µL/— | — | 25 µL | 100 µL |
| NSB | 120 µL | —/5 µL | 1 µL | 25 µL | 100 µL |

NSB: non specific binding

The box is incubated for 60 min. at 22° C. on a shaker at 275 rpm. The wells are filtered over pre-soaked (0.5% polyethylimine(PEI)) GF/C filtermat using an Innotech Harvester or Tomtec Harvester with four washes of ice-cold 20mM Tris, pH 7.8 buffer. Count filters in Gamma-scintillation counter.

Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/ mL in RPMI containing 10% fresh autologous human serum, penicillin streptomycin (10 U/mnL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours. at 37° C. in 5% $CO_2$. At the end of the culture period, cell culture supernatants are assayed for IL-1β, TNF-α, IL-6 and PGE2 production using specific ELISA.

IL-1 Mediated Cytokine Production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10 U/mL) and 0.05% DMSO. Endotoxin free recombinant human IL-1β is then added to a final concentration of 50 pMolar. An aliquot (0.1 mL) of the cells is quickly dispensed into each well of a 96 well plate containing 0.1 L of the compound at the appropriate dilution. and are incubated for 24 hours. at 37° C. in 5% $CO_2$. At the end of the culture period, cell culture supernatants are assayed for TNF-α, IL-6 and $PGE_2$ synthesis using specific ELISA.

Determination of IL-1β, TNF-α. IL-6 and Prostanoid Production from LPS or IL-1 Stimulated PBMC's

IL-1β ELISA

Human IL-1β can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg Maryland.) diluted in Dulbecco's phosphate-buffered saline (-$MgCl_2$, -$CaCl_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli.*. The highest concentration begins at 10 ng/mL followed by 11 two-fold serial dilution's. For detection of IL-1β from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-α monoclonal antibody. The secondary antibody is a 1:2500 dilution of a rabbit anti-human TNF-α polyclonal serum purchased from Genzyme. All other operations are identical to those described above for IL-1b. The standards are prepared in PBS-Tween+10% FBS or HS. Eleven 2 fold dilution's are made beginning at 20 ng/mL TNF-α.

IL-6 ELISA

Levels of secreted human IL-6 are also determined by specific trapping ELISA as described previously in Chin and Kostura, *J. Immunol.* 151, 5574–5585 (1993). (Dynatech) ELISA plates are coated with mouse anti-human IL-6 monoclonal antibody diluted to 0.5 mg/ml in PBS. The secondary antibody, a rabbit anti-human IL-6 polyclonal antiserum, is diluted 1:5000 with PBS-Tween. All other operations are identical to those described above for IL-1β. The standards are prepared in PBS-Tween+10% FBS or HS. Eleven 2 fold dilution's are made beginning at 50 ng/mL IL-6.

PGEE Production

Prostaglandin E2 is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum and 1% CS-HBGF consisting of αFGF and heparin. The cells are then diluted 20-fold before being plated (250 µl) into gelatin coated 96-well plates. Prior to use, culture medium is replaced with fresh medium (200µl). Buffer or test compound (25µl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. IC50 values where appropriate are generated by non-linear regression analysis.

The following exemplary compounds were found to inhibit cytokine production at an $IC_{50}$ of less than about 100 µM and/or inhibit the binding of glucagon to its receptor at an $IC_{50}$ of less than 2 µM.

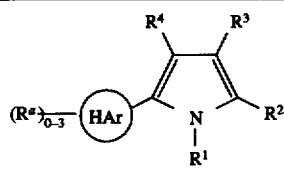

Table of Compounds of Formula I with Gluc IC50 < 2.0 uM and/or Streak IC$_{50}$ < 4 uM

| R1 | (R$_a$)$_{0-3}$-Har | R4 | R3 | R2 |
|---|---|---|---|---|
| H | 4-Pyr | 4-F—Ph | H | Ph |
| H | 4-Pyr | 4-F—Ph | H | 4-(SMe)—Ph |
| H | 4-Pyr | 4-F—Ph | H | 4-(OPh)—Ph |
| H | 4-Pyr | 4-F—Ph | H | 4-(OEt)—Ph |
| H | 4-Pyr | 4-F—Ph | H | 4-(CF3)—PH |
| H | 4-Pyr | 4-F—Ph | H | 4-Br—Ph |
| H | 4-Pyr | 4-F—Ph | H | 4-(tBu)—Ph |
| H | 4-Pyr | 4-F—Ph | H | 4-Et—Ph |
| H | 4-Pyr | 4-F—Ph | H | 4-(SPh)—Ph |
| H | 4-Pyr | 4-F—Ph | H | 2-Me—Ph |
| H | 4-Pyr | 4-F—Ph | H | 4-(OMe)—Ph |
| H | 4-Pyr | 4-F—Ph | H | 4-Me—Ph |
| H | 4-Pyr | 4-F—Ph | H | 4-Cl—Ph |
| H | 4-Pyr | 4-F—Ph | H | 4-(OBu)—Ph |
| H | 4-Pyr | 4-F—Ph | H | 4-(SOMe)—Ph |
| H | 4-Pyr | 4-F—Ph | H | 4-(OBn)—Ph |
| H | 4-Pyr | 4-F—Ph | H | 4-F—Ph |
| H | 4-Pyr | 4-F—Ph | H | 3,4-Cl—Ph |
| H | 4-Pyr | 4-F—Ph | H | 3-CF3—Ph |
| H | 4-Pyr | 4-F—Ph | H | 3,4-F—Ph |
| H | 4-Pyr | 4-F—Ph | H | 3,4-(OCH2O)—Ph |
| H | 4-Pyr | 4-F—Ph | H | 3-Cl-4-F—Ph |
| H | 4-Pyr | 4-F—Ph | H | 3-Me-4-Cl—Ph |
| H | 4-Pyr | 4-F—Ph | H | 4-OCF3—Ph |
| H | 4-Pyr | 4-Cl—Ph | H | 4-Cl—Ph |
| H | 4-Pyr | 4-CF3—Ph | H | 4-Cl—Ph |
| H | 4-Pyr | 3-Cl—Ph | H | 4-Cl—Ph |
| H | 3-Pyr | 4-F—Ph | H | 4-Cl—Ph |
| H | 4-Pyr | 4-OMe—Ph | H | 4-Cl—Ph |
| H | 4-Pyr | 4-F—Ph | H | 4-NO2—Ph |
| H | 4-Pyr | 4-F—Ph | H | 3-NO2—Ph |
| H | 4-Pyr | 4-F—Ph | H | 4-(COOEt)—Ph |
| H | 4-Pyr | 4-F—Ph | H | 4-CN—Ph |
| H | 4-Pyr | 4-F—Ph | H | 3-CN—Ph |
| H | 4-Pyr | 4-F—Ph | H | 2-NO2—Ph |
| H | 4-Pyr | 4-F—Ph | H | 4-(COOH)—Ph |
| H | 4-Pyr | 4-F—Ph | H | 4-(CH2NH2)—Ph |
| H | 4-Pyr | 4-F—Ph | H | 4-NH2—Ph |
| H | 4-Pyr | 4-F—Ph | H | 3-NH2—Ph |
| H | 4-Pyr | 4-F—Ph | H | 2-NH2—Ph |
| H | 2-Pyr | 4-F—Ph | H | 4-Cl—Ph |
| H | 4-pyr | 4-Br—Ph | H | 4-Cl—Ph |
| H | 4-Pyr | 4-Ph—Ph | H | 4-Cl—Ph |
| H | 4-Pyr | 4-(4-CF3—Ph)—Ph | H | 4-Cl—Ph |
| H | 4-Pyr | 3-Br—Ph | H | 4-Cl—Ph |
| H | 4-Pyr | 4-(4-OMe—Ph)—Ph | H | 4-Cl—Ph |
| H | 4-Pyr | 3-Ph—Ph | H | 4-Cl—Ph |
| H | 4-Pyr | 3-(4-OMe—Ph)—Ph | H | 4-Cl—Ph |
| H | 4-Pyr | 4-(1-Napthyl)-Ph | H | 4-Cl—Ph |
| H | 4-Pyr | 4-(thiophen-2-yl)-Ph | H | 4-Cl—Ph |
| H | 4-Pyr | 4-tBu—Ph | H | 4-Cl—Ph |
| H | 4-Pyr | 4-(4-Me—Ph)—Ph | H | 4-Cl—Ph |
| H | 4-Pyr | 4-(4-F—Ph)—Ph | H | 4-Cl—Ph |
| H | 4-Pyr | 4-(3-NO2—Ph)—Ph | H | 4-Cl—Ph |
| H | 4-Pyr | 3-(3-NO2—Ph)—Ph | H | 4-Cl—Ph |
| H | 4-Pyr | 4-(thiophen-3-yl)-phenyl | H | 4-Cl—Ph |
| H | 4-Pyr | 3-(thiophen-2-yl)-phenyl | H | 4-Cl—Ph |
| H | 4-Pyr | 3-(thiophen-3-yl)-phenyl | H | 4-Cl—Ph |
| H | 4-Pyr | 4-(3-(i-Bu)-6-(SO2NH2tBu)-phenyl)-phenyl | H | 4-Cl—Ph |
| H | 4-Pyr | 4-(4-(n-Bu)-phenyl)-phenyl | H | 4-Cl—Ph |
| H | 4-Pyr | 4-(3-(iBu)-6-(SO2NH2)-phenyl)-phenyl | H | 4-Cl—Ph |
| H | 4-pyr | 3-(4-(n-Bu)-phenyl)-phenyl | H | 4-Cl—Ph |
| H | 4-Pyr | 4-(5-(n-Bu)-thiophenyl)-phenyl | H | 4-Cl-phenyl |
| H | 4-Pyr | 2-F-4-Br-phenyl | H | 4-Cl—Ph |
| H | 4-Pyr | 2-(F)-4-(5-(n-Bu)-thiophen-2-yl)-phenyl | H | 4-Cl—Ph |
| H | 4-Pyr | 4-F-Phenyl | Br | 4-Cl—Ph |
| H | 4-Pyr | 4-F-phenyl | Cl | 4-Cl-phenyl |
| H | 4-pyr | 3,5-(Br)-phenyl | H | 4-Cl—Ph |
| H | 4-pyr | 3,5-(thiophen-2-yl)-phenyl | H | 4-Cl-phenyl |
| H | 4-Pyr | CO2Et | H | 4-Cl—Ph |
| H | 4-Pyr | 3,4-(4-OMe—Ph)—Ph | H | 4-Cl—Ph |
| H | 4-Pyr | 3,5-(4-Me—Ph)—Ph | H | 4-Cl—Ph |
| H | 4-Pyr | 4-(OCH2CO2Me)—Ph | H | 4-Cl—Ph |
| H | 4-Pyr | 4-(OMe)—Ph | H | 4-Cl—Ph |
| H | 4-Pyr | 4-(iPr)—Ph | H | 4-Cl—Ph |
| H | 4-Pyr | 4-(OBn)—Ph | H | 4-Cl—Ph |
| H | 4-Pyr | 5-(Ph)-thiazol-2-yl | H | 4-Cl—Ph |
| H | 4-Pyr | 4-(Br)-thiophen-2-yl | H | 4-Cl—Ph |
| H | 4-Pyr | 2-(OPr)—Ph | H | 4-Cl—Ph |
| H | 4-Pyr | 3-thiophenyl | H | 4-Cl—Ph |
| H | 4-Pyr | CO-(4-(N-phenyl)-piperizinyl) | H | 4-Cl—Ph |
| H | 4-Pyr | CONH-2-biphenyl | H | 4-Cl—Ph |
| H | 4-Pyr | 3,5-(3-nitrophenyl)-phenyl | H | 4-Cl—Ph |
| H | 4-Pyr | 4-(benzofuran-2-yl)-phenyl | H | 4-Cl—Ph |
| H | 4-Pyr | 3-Br-5-(thiophen-2-yl)-phenyl | H | 4-Cl—Ph |
| H | 4-Pyr | 4-(5-(Cl)-thiophen-2-yl)-phenyl | H | 4-Cl—Ph |
| H | 4-Pyr | 4-(3,5-(CF3)-phenyl)- | H | 4-Cl—Ph |

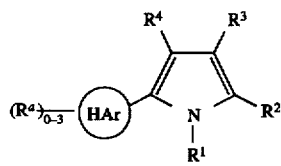
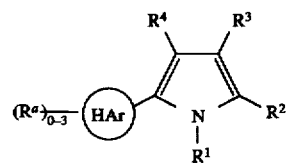

Table of Compounds of Formula I with Gluc IC50 < 2.0 uM and/or Streak IC$_{50}$ < 4 uM

| R1 | (R$_a$)$_{0-3}$-Har | R4 | R3 | R2 |
|---|---|---|---|---|
| H | 4-Pyr | 4-(2-(OMe)-phenyl)-phenyl | H | 4-Cl—Ph |
| H | 4-Pyr | 4-(4-Cl-phenyl)-phenyl | H | 4-Cl—Ph |
| H | 4-Pyr | 4-(CO2Me)-phenyl | H | 4-Cl—Ph |
| H | 4-Pyr | 2-F-4-(thiophen-2-yl)-phenyl | H | 4-Cl—Ph |
| H | 4-Pyr | 4-(3-(NH2)-phenyl)-phenyl | H | 4-Cl—Ph |
| H | 4-Pyr | 4-(3-(OMe)-phenyl)-phenyl | H | 4-Cl—Ph |
| H | 4-Pyr | 2-Br—Ph | H | 4-Cl—Ph |
| H | 4-Pyr | 2,6-F—Ph | H | 4-Cl—Ph |
| H | 4-Pyr | CONH-adamantyl | H | 4-Cl—Ph |
| H | 4-quinolinyl | 4-F—Ph | H | 4-Cl—Ph |
| H | 4-Pyr | CO2Bn | H | 4-Cl—Ph |
| H | 4-Pyr | 3-OBn—Ph | H | 4-Cl—Ph |
| H | 4-Pyr | 4-(t-CHCH—Ph)—Ph | H | 4-Cl—Ph |
| H | 4-Pyr | 9-phenanthrenyl | H | 4-Cl—Ph |
| H | 4-Pyr | 3-(OPh)—Ph | H | 4-Cl—Ph |
| H | 4-Pyr | 2-(OMe)—Ph | H | 4-Cl—Ph |
| H | 4-Pyr | 4-F—Ph | H | 2,4-Cl—Ph |
| H | 4-Pyr | 4-F—Ph | H | t-Bu |
| H | 4-Pyr | 4-F—Ph | H | Me |
| H | 4-Pyr | 4-F—Ph | H | 4-(N-CBz)-piperidinyl |
| H | 4-pyr | 4-CN-phenyl | H | 4-Cl-phenyl |
| H | 4-Pyr | 2,4-F-Phenyl | H | 4-Cl—Ph |
| H | 4-Pyr | 2,4,6-F-phenyl | H | 4-Cl-phenyl |
| H | 4-Pyr | 2-(3-OMe-phenyl)-phenyl | H | 4-Cl-phenyl |
| H | 4-Pyr | 2-(3-NO2-phenyl)-phenyl | H | 4-Cl-phenyl |
| H | 4-Pyr | 2-(thiophen-2-yl)-phenyl | H | 4-Cl-phenyl |
| H | 4-pyr | 2-indolyl | H | 4-Cl—Ph |
| H | 4-Pyr | 2-(OEt)-phenyl | H | 4-Cl-phenyl |
| H | 4-pyr | 2-(OMe)-5-(Br)-phenyl | H | 4-Cl-phenyl |
| H | 4-pyr | 5-(2-(CO2Me)-thiophen-3-yl)-furan-2-yl | H | 4-Cl-phenyl |
| H | 4-pyr | 2,5-(OMe)-phenyl | H | 4-Cl-phenyl |
| H | 4-pyr | 4-F-phenyl | H | 3-Cl-phenyl |
| H | 4-pyr | 4-F-phenyl | H | 4-F-phenyl |
| H | 4-Pyr | 4-(2-thiophenyl)-phenyl | H | 4-F—Ph |
| H | 4-Pyr | 4-F-phenyl | H | 2-F-phenyl |
| H | 4-Pyr | 2-F-4-(2-(5-Cl-thiophen-2-yl)-phenyl | H | 4-Cl-phenyl |
| H | 4-Pyr | 4-(CONHtBu)-phenyl | H | 4-Cl-phenyl |
| H | 4-pyr | 4-F-phenyl | H | 2-(OMe)-4-(Cl)-phenyl |
| H | 4-(2-F)-pyr | 4-F-phenyl | H | 4-Cl-phenyl |
| H | 4-pyr | 4-(N-methyltetrazol yl)-phenyl | H | 4-Cl-phenyl |
| H | 4-pyr | 2-(Cl)-4-(Br)-phenyl | H | 4-Cl-phenyl |
| H | 4-pyr | 4-(CO2Et)-phenyl | H | 4-Cl-phenyl |
| H | 4-Pyr | 4-F-phenyl | H | 4-N-(acetyl)-piperidinyl |
| H | 4-Pyr | 4-F-phenyl | H | 4-N-(Me)-piperidinyl |
| H | 4-pyr | 4-F-phenyl | H | 4-N-(methoxycarbonyl)-piperidinyl |
| H | 4-Pyr | 4-F-phenyl | H | 4-N-(isopropoxy-carbonyl)-piperidinyl |
| H | 4-Pyr | 4-F-phenyl | H | 4-piperidinyl |
| H | 3-F-4-pyr | 4-F-phenyl | H | 4-Cl-phenyl |
| H | 3-(Me)-4-pyridyl | 4-F-phenyl | H | 4-Cl-phenyl |
| H | 4-pyr | 2-(ethoxy)-5-(Br)-phenyl | H | 4-Cl-phenyl |
| H | 4-pyr | 2,5-(F)-phenyl | H | 4-Cl-phenyl |
| H | 4-Pyr | 2-(3-(Cl)-propoxy)-phenyl | H | 4-Cl-Phenyl |
| H | 4-Pyr | 2-(propoxy)-5-(Br)-phenyl | H | 4-Cl-phenyl |
| H | 4-Pyr | 2-(F)-5-(Br)-Phenyl | H | 4-Cl-Phenyl |
| H | 4-pyr | 4-(CONBn2)—Ph | H | 4-Cl-Phenyl |
| H | 4-Pyr | 4-(3-Pyr)-phenyl | H | 4-Cl-phenyl |
| H | 4-pyr | 4-(CO-(N-Boc-piperazin))-phenyl | H | 4-Cl-phenyl |
| H | 4-pyr | 4-(CONPn2)-phenyl | H | 4-Cl-phenyl |
| H | 4-pyr | 4-(CO-morpholinyl)-phenyl | H | 4-Cl-phenyl |
| H | 4-Pyr | 4-(CO-L-proline-OtBu)-phenyl | H | 4-Cl-phenyl |
| H | 4-Pyr | 4-(CO-spiroindene)-phenyl | H | 4-Cl-phenyl |
| H | 4-pyr | 4-(5-(Me)-1,3,4-oxadiazol-2-yl)-phenyl | H | 4-Cl-phenyl |
| H | 4-Pyr | 4-(5-(Bu)-1,3,4-oxadiazol-2-yl)-phenyl | H | 4-Cl-phenyl |

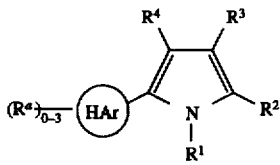
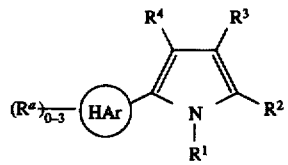

Table of Compounds of Formula I with Gluc IC50 < 2.0 uM and/or Streak IC$_{50}$ < 4 uM

| R1 | (R$_a$)$_{0-3}$-Har | R4 | R3 | R2 |
|---|---|---|---|---|
| H | 4-pyr | CO2-(2-phenyl-phenyl) | H | 4-Cl-phenyl |
| H | 4-(2-methyl)-pyridyl | 4-F-phenyl | H | 4-Cl-phenyl |
| H | 4-pyr | t-CHCHphenyl | H | 4-Cl-phenyl |
| H | 4-pyr | 2-(t-CHCH-phenyl)-phenyl | H | 4-Cl-phenyl |
| H | 4-pyr | 2-(OBn)-phenyl | H | 4-Cl-phenyl |
| H | 4-Pyr | 2-(O-hexyl)-phenyl | H | 4-Cl-phenyl |
| H | 4-pyr | 2-(O-nonyl)-phenyl | H | 4-Cl-phenyl |
| H | 4-pyr | 2-(O-iPr)-phenyl | H | 4-Cl-phenyl |
| H | 4-pyr | 2-(O-iBu)-phenyl | H | 4-Cl-phenyl |
| H | 4-pyr | 2-(O-butyl)-phenyl | H | 4-Cl-phenyl |
| H | 4-pyr | 2-(O-allyl)-phenyl | H | 4-Cl-phenyl |
| H | 4-pyr | 2-(OCH2-2,6-(Cl)-phenyl)-phenyl | H | 4-Cl-phenyl |
| H | 4-pyr | 4-(2-pyr)-phenyl | H | 4-Cl-phenyl |
| 2-OH-phenyl | 4-pyr | 2-F-4-Br-phenyl | H | 4-Cl-phenyl |
| H | 4-pyr | 4-(2-SO2NHtBu-phenyl)-2-F-phenyl | H | 4-Cl-phenyl |
| H | 4-pyr | 4-NO2-phenyl | H | 4-Cl-phenyl |
| H | 4-pyr | 4-F-phenyl | H | c-hexyl |
| H | 4-pyr | CO2Et | H | N-(CBz)-piperidin-4-yl |
| H | 4-pyr | 4-NH2-phenyl | H | 4-Cl-phenyl |
| H | 4-pyr | 4-(NHCO2-butyl)-phenyl | H | 4-Cl-phenyl |
| H | 4-pyr | 4-F-phenyl | Me | 4-Cl-phenyl |
| H | 4-Pyr | 4-F—Ph | CN | 4-Cl—Ph |
| H | 4-pyr | 4-(NHSO2-butyl)-phenyl | H | 4-Cl-phenyl |
| H | 4-pyr | 2-(OCO-propyl)-phenyl | H | 4-Cl-phenyl |
| H | 4-pyr | 2-(O-(CH2)3-SMe)-phenyl | H | 4-Cl-phenyl |
| H | 4-Pyr | 4-(NHCO2Bn)-phenyl | H | 4-Cl-phenyl |
| H | 4-pyr | 4-(NHCO2phenyl)-phenyl | H | 4-Cl-phenyl |
| H | 4-Pyr | 4-F—Ph | H | N-(COOCH2Ph-4-Cl)-piperidin-4-yl |
| H | 4-pyr | 4-F—Ph | H | N-(COOCH2Ph-4-Br)-piperidin-4-yl |
| H | 4-pyr | 4-F—Ph | H | N-(COOCH2Ph-4-Ph)-piperidin-4-yl |
| H | 4-Pyr | 4-F—Ph | H | N-(COOCH2Ph-4-NO2)-piperidin-4-yl |
| H | 4-Pyr | 4-F—Ph | H | N-(COOCH2Ph-3-Cl)-piperidin-4-yl |
| H | 4-Pyr | 4-F—Ph | H | N-(COOCH2Ph-2,4,5-OMe)-piperidin-4-yl |
| H | 4-Pyr | 4-F—Ph | H | N-(COOCH2Ph-2-Cl)-piperidin-4-yl |
| H | 4-Pyr | 4-F—Ph | H | 4-(NHCBz)-cylohexyl |
| H | 4-Pyr | 4-F—Ph | H | N-(COOCH2Ph)-piperidin-3-yl |
| H | 4-Pyr | 4-F—Ph | ethyl | 4-Cl—Ph |
| H | 4-Pyr | 4-F—Ph | Ph | 4-Cl—Ph |
| H | 4-Pyr | 4-F—Ph | H | 4-(NH2)-cyclohexyl |
| H | 4-Pyr | 4-F—Ph | H | piperidin-3-yl |
| H | 4-Pyr | 2-(hydroxy)-Ph | H | 4-Cl—Ph |
| H | 4-Pyr | 2-(4-(Cl)—SPh)—Ph | H | 4-Cl—Ph |
| H | 4-Pyr | 2-(OPh)—Ph | H | 4-Cl—Ph |
| H | 4-Pyr | 2-(O(CH2)3OMe)—Ph | H | 4-Cl—Ph |
| H | 4-Pyr | 2-(OCONMe2)—Ph | H | 4-Cl—Ph |
| H | 4-Pyr | 2-(S-tBu)—Ph | H | 4-Cl—Ph |
| H | 4-Pyr | 4-(OPr)—Ph | H | 4-Cl—Ph |
| H | 4-Pyr | 2-(F)-4-(2-pyridyl)-Ph | H | 4-Cl—Ph |
| H | 4-Pyr | 2-(OPr)-4-(Br)—Ph | H | 4-Cl—Ph |
| H | 4-Pyr | 4-(5-((CH2)4-OH)-thiophen-2-yl)-Ph | H | 4-Cl—Ph |
| H | 4-Pyr | 4-(5-((CH2)4-azido)-thiophen-2-yl)-Ph | H | 4-Cl—Ph |
| H | 4-Pyr | N-(2,6-(Me)-Ph)-piperazin-4-yl-CO— | H | 4-Cl—Ph |
| H | 4-Pyr | 4-(3-OMe—Ph)-2-(OPr)—Ph | H | 4-Cl—Ph |
| H | 4-Pyr | 3-(OPr)—Ph | H | 4-Cl—Ph |
| H | 4-Pyr | 4-(3-NH2—Ph)-2-(OPr)—Ph | H | 4-Cl—Ph |
| H | 4-Pyr | benzyl | H | 4-Cl—Ph |
| H | 4-Pyr | 2-(furan-2-yl)-Ph | H | 4-Cl—Ph |
| H | 4-Pyr | 4-(furan-2-yl)-Ph | H | 4-Cl—Ph |
| H | 4-Pyr | 4-(2-(OH)-5-((Br)—Ph))-2-(OPr)—Ph | H | 4-Cl—Ph |
| H | 4-Pyr | 4-(5-(Bu)-thiophen-2- | H | 4-Cl—Ph |

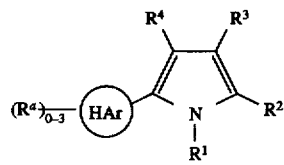

Table of Compounds of Formula I with Gluc IC50 < 2.0 uM and/or Streak IC$_{50}$ < 4 uM

| R1 | (R$_a$)$_{0-3}$-Har | R4 | R3 | R2 |
|---|---|---|---|---|
| H | 4-Pyr | 4-(3-(OBu)-Ph)-Ph | H | 4-Cl—Ph |
| H | 4-Pyr | 4-(3-(OBu)-Ph)—Ph | H | 4-Cl—Ph |
| H | 4-Pyr | 4-(5-((CH2)4-amino)-thiophen-2-yl)-Ph | H | 4-Cl—Ph |
| H | 4-Pyr | 4-(Bu)-thiophen-2-yl)-Ph | H | 4-Cl—Ph |
| H | 4-Pyr | 1-napthyl | H | 4-Cl—Ph |
| H | 4-pyr | quinolin-8-yl | H | 4-Cl—Ph |
| H | 4-Pyr | 4-(2-(OMe)-5-(Br)-Ph)-2-(OPr)—Ph | H | 4-Cl—Ph |
| H | 4-Pyr | 4-(cyclohexyl)-Ph | H | 4-Cl—Ph |
| H | 4-Pyr | 4-(Bu)—Ph | H | 4-Cl—Ph |
| H | 2-(amino)-pyridin-4-yl | 4-F—Ph | H | 4-Cl—Ph |
| H | pyrimidin-4-yl | 4-F—Ph | H | 4-Cl—Ph |
| H | 4-Pyr | 4-(5-(NO2)-thiophen-2-yl)-phenyl | H | 4-Cl—Ph |
| H | 4-Pyr | 4-(3-(Me)-thiophen-2-yl)-phenyl | H | 4-Cl—Ph |
| H | 4-Pyr | 4-(2,5-(OMe)—Ph)—Ph | H | 4-Cl—Ph |
| H | 4-Pyr | 4-(2,4,6-(Me)—Ph)—Ph | H | 4-Cl—Ph |
| H | 4-Pyr | 4-(5-(ethyl)-thiophen-2-yl)-Ph | H | 4-Cl—Ph |
| H | 4-Pyr | 4-(5-(Me)-thiophen-2-yl)-Ph | H | 4-Cl—Ph |
| H | 4-Pyr | 4-(5-(propyl)-thiophen-2-yl)-phenyl | H | 4-Cl—Ph |
| H | 4-Pyr | 4-(4-(Pr)—Ph)—Ph | H | 4-Cl—Ph |
| H | 4-Pyr | 4-I—Ph | H | 4-Cl—Ph |
| H | 4-Pyr | 4-(5-(OMe)-pyridin-2-yl)-Ph | H | 4-Cl—Ph |
| H | 4-Pyr | 4-(3-(Me)—Ph)—Ph | H | 4-Cl—Ph |
| H | 4-Pyr | 4-(3,4-(methylene-dioxy)-Ph)—Ph | H | 4-Cl—Ph |
| H | 4-Pyr | 4-(3-(propoxy)-Ph)—Ph | H | 4-Cl—Ph |
| H | 4-Pyr | 4-(3-(acetyl)-Ph)—Ph | H | 4-Cl—Ph |
| H | 4-Pyr | 4-(3-(NO2)-4-(Me)—Ph)—Ph | H | 4-Cl—Ph |
| H | 4-Pyr | 4-(3,4-(OMe)—Ph)—Ph | H | 4-Cl—Ph |
| H | 4-Pyr | 4-(3- | H | 4-Cl—Ph |

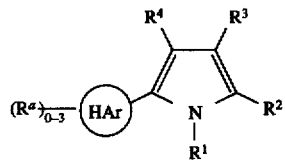

Table of Compounds of Formula I with Gluc IC50 < 2.0 uM and/or Streak IC$_{50}$ < 4 uM

| R1 | (R$_a$)$_{0-3}$-Har | R4 | R3 | R2 |
|---|---|---|---|---|
| H | 4-Pyr | (OCH2CH2OMe)—Ph)—Ph | H | 4-Cl—Ph |
| H | 4-Pyr | 4-(4-(CN)-3-(Me)—Ph)—Ph | H | 4-Cl—Ph |
| H | 4-Pyr | 4-(5-(acetyl)-thiophen-2-yl)-phenyl | H | 4-Cl—Ph |
| H | 4-Pyr | CH2CH2Ph | H | 4-Cl—Ph |
| H | 4-Pyr | CH2CH(Me)Ph | H | 4-Cl—Ph |
| H | 4-Pyr | CH(Me)CH2-(3,4-(methylene-dioxy)-Ph) | H | 4-Cl—Ph |
| H | 4-Pyr | 4-(3-(OCH2CH2OEt)—Ph)—Ph | H | 4-Cl—Ph |
| H | 4-Pyr | 4-((indane-1-one)-5-yl)-Ph | H | 4-Cl—Ph |
| H | 4-Pyr | 4-(4-(Et)—Ph)—Ph | H | 4-Cl—Ph |
| H | 4-Pyr | 4-(2-trimethylsilyl ethynyl)-Ph | H | 4-Cl—Ph |
| H | 4-Pyr | 4-(ethynyl)-Ph | H | 4-Cl—Ph |
| H | 4-Pyr | 4-(5-(CO$_2$Et)-furan-2-yl)-phenyl | H | 4-Cl—Ph |
| H | 4-pyr | 4-(2-phenylethynyl)-phenyl | H | 4-Cl—Ph |
| H | 4-Pyr | 4-(2-(ethyl)-phenyl)-Ph | H | 4-Cl—Ph |
| H | quinolin-6-yl | 4-(F)-phenyl | H | 4-Cl—Ph |
| H | 4-pyr | 4-(2-(n-butyl)-ethynyl)-phenyl | H | 4-Cl—Ph |
| H | 4-pyr | 4-(2-(4-methyl-phenyl)-ethynyl)-phenyl | H | 4-Cl—Ph |
| H | 4-Pyr | 2,4-(propoxy)-phenyl | H | 4-Cl—Ph |
| H | 4-Pyr | 2-(propoxy)-5-(F)-phenyl | H | 4-Cl—Ph |
| H | 4-pyr | 3,5-(Br)-2-(propoxy)-phenyl | H | 4-Cl—Ph |
| H | 4-Pyr | 4-(2-(4-(Cl)-phenyl)-ethynyl)-phenyl | H | 4-Cl—Ph |
| H | 4-Pyr | 4-(2-(2-pyr)-ethynyl)-phenyl | H | 4-Cl—Ph |
| H | 4-Pyr | 2-(propoxy)-5-(Cl)-phenyl | H | 4-Cl—Ph |
| H | 4-Pyr | 2-(propoxy)-3-(Cl)-phenyl | H | 4-Cl—Ph |
| H | 4-Pyr | 2-(propoxy)-3-(F)-phenyl | H | 4-Cl—Ph |
| H | 4-Pyr | 4-(5-pyrimidinyl)-phenyl | H | 4-Cl—Ph |

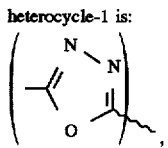

Table of Compounds of Formula I with Gluc IC50 < 2.0 uM and/or Streak IC$_{50}$ < 4 uM

| R1 | (R$_a$)$_{0-3}$-Har | R4 | R3 | R2 |
|---|---|---|---|---|
| H | 4-Pyr | 4-(2-(4-(F)-phenyl)-ethynyl)-phenyl | H | 4-Cl—Ph |
| H | 4-Pyr | 4-(2-(4-(ethyl)-phenyl)-ethynyl)-phenyl | H | 4-Cl—Ph |
| H | 4-Pyr | 4-(2-(4-(butyl)-phenyl)-ethynyl)-phenyl | H | 4-Cl—Ph |
| H | 2-(F)-pyridin-5-yl | 4-F—Ph | H | 4-Cl—Ph |
| H | 4-Pyr | cyclohexyl | H | 4-Cl—Ph |
| H | 4-Pyr | 4-F—Ph | H | 2-Br—Ph |
| H | 4-Pyr | 3-(CF3)—Ph | Me | N-methyl-piperidin-4-yl |
| H | 4-Pyr | 3-(CF3)—Ph | Me | piperidin-4-yl |
| H | 2-F-pyridin-5-yl | 4-F-Ph | H | 4-Cl—Ph |
| H | 2-OH-pyridin-5-yl | 4-F—Ph | H | 4-Cl—Ph |
| H | 4-Pyr | 2-propoxy-4-(2-Ph-ethynyl)-Ph | H | 4-Cl—Ph |
| H | 4-Pyr | 4-(2-propenyl)-cyclohexen-1-yl | H | 4-Cl—Ph |
| H | 4-Pyr | N-(Cbz)-piperidin-4-yl | H | 4-Cl—Ph |
| H | 4-Pyr | i-Propyl | H | 4-Cl—Ph |
| H | pyridazin-4-yl | 4-F—Ph | H | 4-Cl—Ph |
| H | 4-Pyr | 4-F—Ph | H | 2-CN—Ph |
| H | 4-Pyr | 2-CN—Ph | H | 4-Cl—Ph |
| H | 4-Pyr | 4-F—Ph | n-Bu | 4-Cl—Ph | wherein: CO=carbonyl, Ph=phenyl, pyr=pyridyl, Pip=piperidinyl, OMe=methoxy, iPr=isopropyl, thioPh-thiophenyl, (A)=SO$_2$NH2tBu, (B)=SO$_2$NH$_2$, (C)=SO$_2$NHCO$_2$nBu, (D)=tetrazol-5-yl, (E)=5-(n-Bu)-thiophen-2-yl, (G)=5-(Cl)-thiophen-2-yl, (J)=N-methyltetrazolyl, (M)=N-Boc-piperazin, (Q)=CO-spiroindane-1, (W)=CO-L-proline-OtBu, (X)=2-OH-Ph, (Y)=2-SO$_2$NH$_2$tBu-Ph, (Z)=piperidin-4-yl.

spiroindene-1 is:

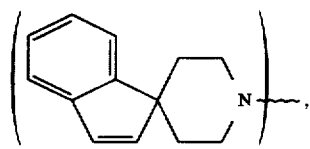

-continued heterocycle-1 is:

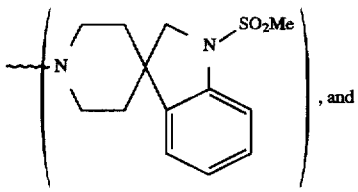

spiroindane-1 is:

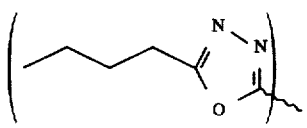
, and heterocycle-2 is:

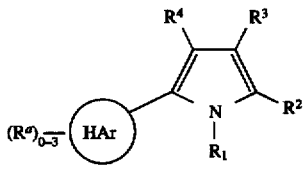

What is claimed is:
1. A compound represented by formula I:

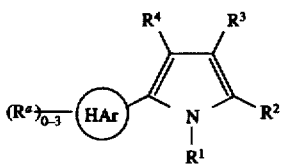

or a pharmaceutically acceptable salt, solvate, hydrate or tautomer thereof, wherein:

represents pyridyl which is unsubstituted or substituted with 1–3 R$^a$ groups;

each R$^a$ independently represents a member selected from the group consisting of: halo, aryl(R$^b$)$_{0-2}$, heteroaryl (R$^b$)$_{0-2}$, CF$_3$, OCF$_3$, CN, NO$_2$, R$^{21}$, OR$^{23}$; SR$^{23}$, S(O) R$^{23}$, SO$_2$R$^{21}$, NR$^{20}$R$^{23}$, NR$^{20}$COR$^{21}$, NR$^{20}$CO$_2$R$^{21}$, NR$^{20}$CONR$^{20}$R$^{23}$, NR$^{20}$SO$_2$R$^{21}$, NR$^{20}$C(NR$^{20}$) NHR$^{23}$, COR$^{20}$, CO$_2$R$^{23}$, CONR$^{20}$R$^{23}$, SO$_2$NR$^{20}$R$^{23}$, SO$_2$NR$^{20}$COR$^{21}$, SO$_2$NR$^{20}$CONR$^{20}$R$^{23}$, SO$_2$NR$^{20}$CO$_2$R$^{21}$OCONR$^{20}$R$^{23}$, OCONR$^{20}$SO$_2$R$^{21}$, C(NR$^{20}$)NR$^{20}$R$^{23}$, C(O)OCH$_2$OC(O)R$^{20}$, CONR$^{20}$SO$_2$R$^{21}$ and SO$_2$NR$^{20}$CO$_2$R$^2$;

when present, each R$^b$ independently represents a member selected from the group consisting of: halo, CF$_3$, OCF$_3$, CN, NO$_2$, OR$^{23}$; SR$^{23}$, S(O)R$^{23}$, SO$_2$R$^{21}$, NR$^{20}$R$^{23}$, NR$^{20}$COR$^{21}$, NR$^{20}$CO$_2$R$^{21}$, NR$^{20}$CONR$^{20}$R$^{23}$, NR$^{20}$SO$_2$R$^{21}$, NR$^{20}$C(NR$^{20}$) NHR$^{23}$, COR$^{20}$, CO$_2$R$^{23}$, CONR$^{20}$R$^{23}$, SO$_2$NR$^{20}$R$^{23}$, SO$_2$NR$^{20}$COR$^{21}$, SO$_2$NR$^{20}$CONR$^{20}$R$^{23}$, SO$_2$NR$^{20}$CO$_2$R$^{21}$, OCONR$^{20}$R$^{23}$, OCONR$^{20}$SO$_2$R$^{21}$, C(NR$^{20}$)NR$^{20}$R$^{23}$, C(O)OCH$_2$OC(O)R$^{20}$, CONR$^{20}$SO$_2$R$^{21}$, and SO$_2$NR$^{20}$CO$_2$R$^2$;

R$^1$ is selected from the group consisting of: H, aryl, C$_{1-15}$ alkyl, C$_{3-15}$ alkenyl, C$_{3-15}$ alkynyl and heterocyclyl, said alkyl, aryl, alkenyl, alkynyl and heterocyclyl being optionally substituted with from one to three members selected from the group consisting of: aryl, heteroaryl, heterocyclyl, halo, $OR^{23}$, $SR^{23}$, $N(R^{23})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $COR^{20}$, $CO_2R^{23}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$;

$R^2$ is selected from the group consisting of: aryl (with the proviso that aryl is not unsubstituted phenyl), heteroaryl (with the proviso that heteroaryl is not unsubstituted pyridyl), $C_{7-15}$ alkenyl, $C_{2-15}$ alkynyl, $CONR^{20}R^{23}$, $SO_2R^{21}$ (wherein $R^{21}$ is not alkyl or $C_{1-6}$ alkenyl), $SO_2N(R^{20})_2$, $SO_2NR^{20}COR^{21}$, $SO_2NR^{20}CON(R^{20})_2$, $COR^{20}$, $CO_2R^{20}$ (wherein $R^{20}$ is not $C_{1-6}$ alkyl or hydrogen), $CONR^{20}SO_2R^{21}$, $SO_2NR^{20}CO_2R^{21}$ and heterocyclyl, said alkenyl, alkynyl, aryl, heteroaryl and heterocyclyl being optionally substituted with from one to three members selected from the group consisting of: halo, $C_{1-15}$ alkyl, $OCF_3$, $CF_3$, $CN$, aryl, $NO_2$, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R_{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, and $OCONR^{20}R^{23}$;

$R^3$ is selected from the group consisting of: H, aryl, $C_{1-15}$ alkyl, $C_{2-15}$ alkenyl, $C_{2-15}$ alkynyl, halo, $NO_2$, CN, $CONR^{20}R^{23}$, $SO_2R^{21}$, $SO_2N(R^{20})_2$, $SO_2NR^{20}COR^{21}$, $SO_2NR^{20}CON(R^{20})_2$, $COR^{20}$, $CO_2R^{20}$, $CONR^{20}SO_2R^{21}$, $SO_2NR^{20}CO_2R^{21}$ and heterocyclyl, said alkyl, alkenyl, alkynyl, aryl, and heterocyclyl being optionally substituted with from one to three members selected from the group consisting of: halo, $C_{1-15}$ alkyl, $CF_3$, $OCF_3$, $CN$, aryl, $NO_2$, heteroaryl, $OR^{23}$, $SR^{23}$, $N(R^{23})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OR^{20}$ and $OCONR^{20}R^{23}$;

$R^4$ is selected from the group consisting of $COR^{20}$, $COOR^{20}$, $CONR^{20}R^{23}$, aryl, heterocyclyl, $C_{1-15}$ alkyl, $C_{3-15}$ alkenyl, $C_{3-15}$ alkynyl, said alkyl, alkenyl and alkynyl group optionally interrupted by 1–2 oxo or heteroatoms selected from O, S, S(O), $SO_2$ or $NR^{24}$ and said $C_{1-15}$ alkyl, aryl, heterocyclyl, $C_{3-15}$ alkenyl, $C_{3-15}$ alkynyl being optionally substituted with from 1–3 of $R^{21}$, halo, aryl$(R^a)_{0-3}$, heteroaryl$(R^a)_{0-3}$, heterocyclyl, CN, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $OR^{20}CO_2R^{23}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$,

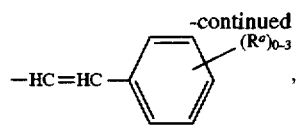

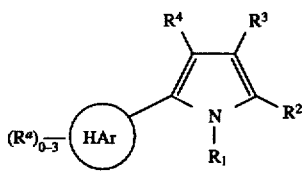

$-C{\equiv}C-$Heteroaryl$(R^a)_{0-3}$, $-HC{=}HC-$Heteroaryl$(R^a)_{0-3}$ and $C(O)OCH_2OC(O)R^{20}$;

$R^{20}$ represents a member selected from the group consisting of: H, $C_{1-15}$ alkyl, $C_{3-15}$ alkenyl, $C_{3-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{3-15}$ alkenyl, $C_{3-15}$ alkynyl, aryl, heterocyclyl and heteroaryl; said alkyl, alkenyl or alkynyl being optionally interrupted by 1–2 heteroatoms selected from O, S, S(O), $SO_2$ or $NR^{24}$ and said alkyl, alkenyl, alkynyl, aryl, heterocyclyl and heteroaryl being optionally substituted with from 1–3 of halo, heterocyclyl, heteroaryl, aryl$(R^a)_{0-2}$, heteroaryl$(R^a)_{0-2}$, CN, $OR^{20}$, $O((CH_2)_nO)_mR^{20}$, $NR^{20}((CH_2)_nO)_mR^{20}$ wherein n represents an integer of from 1 to 4, and m represents an integer of from 1 to 4; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{3-15}$ alkenyl, $C_{3-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$ and $SO_2R^{22}$; and when two $R^{20}$ groups are present, $R^{20}$ and $R^{21}$ are present, or $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

2. A compound of the formula:

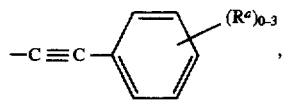

or a pharmaceutically acceptable salt thereof, wherein:

represents pyridyl which is unsubstituted or substituted with 1–3 $R^a$ groups;

each $R^a$ independently represents a member selected from the group consisting of: halo, aryl$(R^b)_{0-2}$, heteroaryl $(R^b)_{0-2}$, $CF_3$, $OCF_3$, $CN$, $NO_2$, $R^{21}$, $OR^{23}$; $SR^{23}$, $S(O)R^{23}$, $SO_2R^{21}$, $NR^{20}R^{23}$, $NR^{20}COR^{21}$, $NR^{20}CO_2R^{21}$, $NR^{20}CONR^{20}R^{23}$, $NR^{20}SO_2R^{21}$, $NR^{20}C(NR^{20})NHR^{23}$, $COR^{20}$, $CO_2R^{23}$, $CONR^{20}R^{23}$, $SO_2NR^{20}R^{23}$, $SO_2NR^{20}COR^{21}$, $SO_2NR^{20}CONR^{20}R^{23}$, $SO_2NR^{20}CO_2R^{21}$, $OCONR^{20}R^{23}$, $OCONR^{20}SO_2R^{21}$, $C(NR^{20})NR^{20}R^{23}$, $C(O)OCH_2OC(O)R^{20}$, $CONR^{20}SO_2R^{21}$, and $SO_2NR^{20}CO_2R^2$;

$R^b$ is $R^a$ minus aryl, heteroaryl and $R^{21}$;

$R^1$ is selected from the group consisting of: H, aryl, $C_{1-15}$ alkyl, $C_{3-15}$ alkenyl, $C_{3-15}$ alkynyl and heterocyclyl, said alkyl, aryl, alkenyl, alkynyl, and heterocyclyl being optionally substituted with from one to three members selected from the group consisting of: aryl, heteroaryl, heterocyclyl, halo, $OR^{23}$, $SR^{23}$, $N(R^{23})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $COR^{20}$, $CO_2R^{23}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$;

$R^2$ is selected from the group consisting of: aryl (wherein aryl is not unsubstituted phenyl), heteroaryl (wherein heteroaryl is not unsubstituted pyridyl), $C_{7-15}$ alkenyl, $C_{2-15}$ alkynyl, $CONR^{20}R^{23}$, $SO_2R^{21}$ (wherein $R^{21}$ is not alkyl or $C_{1-6}$ alkenyl), $SO_2N(R^{20})_2$, $SO_2NR^{20}COR^{21}$, $SO_2NR^{20}CON(R^{20})_2$, $COR^{20}$, $CO_2R^{20}$ (wherein $R^{20}$ is not $C_{1-6}$ alkyl or hydrogen), $CONR^{20}SO_2R^{21}$, $SO_2NR^{20}CO_2R^{21}$ and heterocyclyl, said alkyl, alkenyl, alkynyl, aryl, heteroaryl and heterocyclyl being optionally substituted with from one to three members selected from the group consisting of: halo, $C_{1-15}$ alkyl, $OCF_3$, $CF_3$, $CN$, aryl, $NO_2$, heterocyclyl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, and $OCONR^{20}R^{23}$;

$R^3$ is selected from the group consisting of: H, $C_{1-15}$ alkyl, aryl, $C_{2-15}$ alkenyl, $C_{2-15}$ alkynyl, halo, $NO_2$, $CN$, $CONR^{20}R^{23}$, $SO_2R^{21}$, $SO_2N(R^{20})_2$, $SO_2NR^{20}COR^{21}$, $SO_2NR^{20}CON(R^{20})_2$, $COR^{20}$, $CO_2R^{20}$, $CONR^{20}SO_2R^{21}$, $SO_2NR^{20}CO_2R^{21}$ and heterocyclyl, said alkyl, alkenyl, alkynyl, aryl, and heterocyclyl being optionally substituted with from one to three members selected from the group consisting of: halo, $C_{1-15}$ alkyl, $CF_3$, $OCF_3$, $CN$, aryl, $NO_2$, heteroaryl, $OR^{23}$, $SR^{23}$, $N(R^{23})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OR^{20}$ and $OCONR^{20}R^{23}$;

$R^4$ is selected from the group consisting of $COR^{20}$, $COOR^{20}$, $CONR^{20}R^{23}$, aryl, heterocyclyl, $C_{1-15}$ alkyl, $C_{3-15}$ alkenyl, $C_{3-15}$ alkynyl, said alkyl, alkenyl and alkynyl group optionally interrupted by 1-2 oxo or heteroatoms selected from O, S, S(O), $SO_2$ or $NR^{24}$ and said $C_{1-15}$ alkyl, aryl, heterocyclyl, $C_{3-15}$ alkenyl, $C_{3-15}$ alkynyl being optionally substituted with from 1-3 of $R^{21}$, halo, aryl$(R^a)_{0-3}$, heteroaryl$(R^a)_{0-3}$, heterocyclyl, $CN$, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $OR^{20}CO_2R^{23}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_2OC(O)R^{20}$;

$R^{20}$ represents a member selected from the group consisting of: H, $C_{1-15}$ alkyl, $C_{3-15}$ alkenyl, $C_{3-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{3-15}$ alkenyl, $C_{3-15}$ alkynyl, aryl, heterocyclyl and heteroaryl; said alkyl, alkenyl or alkynyl being optionally interrupted by 1–2 heteroatoms selected from O, S, S(O), $SO_2$ or $NR^{24}$ and said alkyl, alkenyl, alkynyl, aryl, heterocyclyl and heteroaryl being optionally substituted with from 1–3 of halo, heterocyclyl, heteroaryl, aryl$(R^a)_{0-2}$, heteroaryl $(R^a)_{0-2}$, $CN$, $OR^{20}$, $O((CH_2)_nO)_mR^{20}$, $NR^{20}((CH_2)_nO)_mR^{20}$ wherein n represents an integer of from 1 to 4, and m represents an integer of from 1 to 4; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$, and $OCON(R^{20})_2$;

$R^{22}$ is selected from the group consisting of: $C_{1-15}$ alkyl, $C_{3-15}$ alkenyl, $C_{3-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$ and $SO_2R^{22}$; and in any substitutent wherein two $R^{20}$ groups are present, wherein $R^{20}$ and $R^{21}$ are present, or wherein $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

3. A compound in accordance with claim 1 wherein: $R^1$ represents H, alkyl, substituted alkyl, aryl and substituted aryl, said substituted groups being substituted with from 1 to 3 groups selected from $R^a$.

4. A compound in accordance with claim 1 wherein: $R^2$ represents aryl(wherein aryl is not unsubstituted phenyl), heteroaryl (wherein heteroaryl is not unsubstituted pyridyl), $C_{7-15}$ alkenyl, $C_{2-15}$ alkynyl, and heterocyclyl, said alkenyl, alkynyl, aryl, heteroaryl and heterocyclyl groups being unsubstituted or substituted with 1 to 3 groups of $R^a$.

5. A compound in accordance with claim 1 wherein: $R^3$ represents H, $C_{1-15}$ alkyl, halo, $NO_2$, $CN$, $CONR^{20}R^{23}$, $SO_2R^{21}$ and $CO_2R^{20}$, said alkyl group being unsubstituted or substituted with 1 to 3 groups of $R^a$.

6. A compound in accordance with claim 1 wherein: $R^4$ is aryl, $C_{1-15}$ alkyl, $C_{3-15}$ alkenyl, $C_{3-15}$ alkynyl, heterocyclyl, $CO_2R^{20}$ or $CONR^{20}R^{23}$, said alkyl, alkenyl and alkynyl group optionally interrupted by 1–2 oxo or heteroatoms selected from O, S, S(O), $SO_2$ or $NR^{24}$ and said $C_{1-15}$ alkyl, aryl, heterocyclyl, $C_{3-15}$ alkenyl, $C_{3-15}$ alkynyl being optionally substituted with from 1–3 of $R^{21}$, halo, aryl$(R^a)_{0-3}$, heteroaryl($R^a$)$_{0-3}$, heterocyclyl, CN, CF$_3$, NO$_2$, OR$^{23}$, SR$^{23}$, NR$^{20}$R$^{23}$, S(O)R$^{21}$, SO$_2$R$^{21}$, SO$_2$NR$^{20}$R$^{23}$, SO$_2$NR$^{20}$COR$^{21}$, OR$^{20}$CO$_2$R$^{23}$, SO$_2$NR$^{20}$CONR$^{20}$R$^{23}$, NR$^{20}$COR$^{21}$, NR$^{20}$CO$_2$R$^{21}$, NR$^{20}$CONR$^{20}$R$^{23}$, N(R$^{20}$)C(NR$^{20}$)NHR$^{23}$, CO$_2$R$^{23}$, COR$^{20}$, CONR$^{20}$R$^{23}$, CONR$^{20}$SO$_2$R$^{21}$, NR$^{20}$SO$_2$R$^{21}$, SO$_2$NR$^{20}$CO$_2$R$^{21}$, OCONR$^{20}$R$^{23}$, OCONR$^{20}$SO$_2$R$^{21}$, OCONR$^{20}$R$^{23}$,

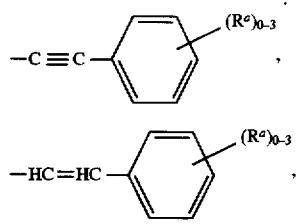

—C≡C—Heteroaryl($R^a$)$_{0-3}$, —HC=HC—Heteroaryl($R^a$)$_{0-3}$ and C(O)OCH$_2$OC(O)R$^{20}$.

7. A compound in accordance with claim 1 wherein: R$^4$ is aryl, alkyl, alkenyl, alkynyl, heterocyclyl, CO$_2$R$^{20}$ or CONR$^{20}$R$^{23}$, said aryl, alkyl, alkenyl, alkynyl, and heterocyclyl being unsubstituted or substituted with 1 to 3 groups of $R^a$.

8. A compound in accordance with claim 1 wherein Har represents 3- or 4-pyridinyl.

9. A compound in accordance with claim 1 wherein from 1–3 $R^a$ groups attached to the Har substituent, independently selected from the group consisting of: halo, aryl($R^b$)$_{0-2}$, heteroaryl($R^b$)$_{0-2}$, CF$_3$, OCF$_3$, NO$_2$, R$^{21}$, OR$^{23}$; SR$^{23}$, S(O)R$^{23}$, SO$_2$R$^{21}$, NR$^{20}$R$^{23}$, NR$^{20}$COR$^{21}$, NR$^{20}$CO$_2$R$^{21}$, NR$^{20}$CONR$^{20}$R$^{23}$, NR$^{20}$SO$_2$R$^{21}$, SO$_2$NR$^{20}$R$^{23}$, SO$_2$NR$^{20}$COR$^{21}$, SO$_2$NR$^{20}$CONR$^{20}$R$^{23}$ and SO$_2$NR$^{20}$CO$_2$R$^{21}$, and $R^b$, R$^{20}$, R$^{21}$, R$^{22}$, R$^{23}$ and R$^{24}$ are as originally defined.

10. A compound in accordance with claim 1 wherein:
R$^1$ is H, aryl, or C$_{1-15}$ alkyl;
R$^2$ is aryl, (wherein aryl is not unsubstituted phenyl), heteroaryl (wherein heteroaryl is not unsubstituted pyridyl) C$_{7-15}$ alkenyl, C$_{2-15}$ alkynyl, heterocyclyl;
R$^3$ is H, halo, NO$_2$, CO$_2$R$^{20}$, CONHiPr or CN; and
R$^4$ is aryl, C$_{1-15}$ alkyl, C$_{2-15}$ alkenyl, C$_{2-15}$ alkynyl, CO$_2$R$^{20}$, CONR$^{20}$R$^{23}$ or heterocyclyl, said aryl, alkyl and heterocyclyl being unsubstituted or substituted with 1 to 3 groups of $R^a$.

11. A compound in accordance with claim 1 wherein:
R$^1$ is H or aryl;
R$^2$ is aryl (wherein aryl is not unsubstituted phenyl), heteroaryl (wherein heteroaryl is not unsubstituted pyridyl), or heterocyclyl;
R$^3$ is H or halo;
R$^4$ is aryl, C$_1$–C$_6$ alkyl, C$_{2-15}$ alkenyl, C$_{2-15}$ alkynyl, CO$_2$R$^{20}$, heterocyclyl or CONR$^{20}$R$^{23}$, said aryl, alkyl and heterocyclyl being unsubstituted or substituted with 1 to 3 groups of $R^a$ and (HAr)

represents pyridyl.

12. A compound in accordance with claim 1 wherein ($R^a$)$_{0-3}$-HAr is selected from the group consisting of:
a) 4-pyridinyl,
b) 2-methyl-4-pyridinyl,
c) 3-methyl-4-pyridinyl,
d) 2-amino-4-pyridinyl,
e) 2-benzylamino-4-pyridinyl,
f) 2-acetylamino-4-pyridinyl,
i) 2-imidazo-(4,5-b)-pyridinyl,
j) 7-imidazo-(4,3-b)-pyridinyl,
k) 2-imidazo-(4,5-b)-pyridinyl,
l) 4-(2-F-pyridinyl),
m) 4-(3-F-pyridinyl),
q) 2-(NH$_2$-pyridinyl),
r) 2-(MeNH-pyridinyl),
s) 2-(N-benzylamino)pyridinyl,
t) 3-pyridinyl,
u) 2-pyridinyl or
v) 4-(2,6-di-Phenyl)-pyridinyl;

R$^1$ is H or 2-OH-Phenyl;

R$^2$ is
1) Cl-Ph,
2) Br-Ph,
3) F-Ph,
4) (C$_1$–C$_4$ alkyl)-Ph,
5) CF$_3$-Ph
6) (O-(C$_1$–C$_4$ alkyl))-Ph,
7) (C$_3$–C$_6$ cycloalkyl)-Ph,
8) phenyl-Ph,
9) CN-Ph,
10) COOH-Ph,
11) NO$_2$-Ph,
12) SMe-Ph,
13) (O-phenyl)-Ph,
14) (S-phenyl)-Ph,
15) (OBn)-Ph,
16) —(S(O)-phenyl)-Ph,
17) OCF$_3$-Ph,
18) CO$_2$Et-Ph,
19) —S(O)Me-Ph,
20) (CH$_2$NH$_2$)-Ph,
21) NH$_2$-Ph,
22) N-CBz-piperdin-4-yl,
23) N-Me-piperdin-4-yl,
24) t-butyl-Ph,
25) 2-thiophenyl,
26) 3,4-(OCH$_2$O)-Ph,
27) 3-(Cl)-4-(F)-Ph,
28) —S(O)Ph,
29) 2,4-(Cl)-Phenyl,
30) 3,4-(Cl)-Phenyl,
31) 2-(OMe)-4-(Cl)Ph,
32) 4-N-(acetyl)-piperidinyl,
33) 4-N-(OMe-CO)-piperidinyl,
34) 4-N-(iPr-CO)-piperidinyl,
35) 4-piperidinyl,
36) 4-pyridinyl,
37) c-hexyl,
38) 4-(OBn)-Phenyl,
39) 4-N(CO$_2$Me)-piperidinyl or
40) 3-(Me)-4-(F)-Phenyl;

R$^3$ is H, Br or Cl;

R$^4$ is
1. 4-(phenyl)-Ph,
2. 3-(phenyl)-Ph,
3. 4-(2-thiophenyl)-Ph,
4. 4-(t-butyl)-Ph,
5. 4-(toluyl)-Ph,
6. 4-(4-fluorophenyl)-Ph,
7. 4-(3-nitro-phenyl)-Ph, 8. 3-(3-nitro-phenyl)-Ph,
9. 4-(quinolinyl)-Ph,
10. Cl-Ph,
11. OMe-Ph,
12. Br-Ph,
13. $CF_3$-Ph,
14. (cyclohexyl)-Ph,
15. (i-butyl)-Ph,
16. (4-(2-tetrazol-5-yl)-phenyl)-Ph,
17. 4-(3-thiophenyl)-Ph,
18. 2-(napthyl)-Ph,
19. F-Ph,
20. hydroxy-Ph,
21. 4-$NMe_2$-Ph,
22. $CO_2Et$-Ph,
23. COOH-Ph,
24. 4(OMe)-Ph,
25. 2-(F)-4-(Br)-Ph,
26. 4-(4-$CF_3$-phenyl)-Ph,
27. 4-(4-OMe-phenyl)-Ph,
28. 3-(4-OMe-phenyl)-Ph,
29. 4-(1-naphthyl)-Ph,
30. phenyl,
31. 4-(4-Me-Ph)-Ph,
32. 3-(2-thiophenyl)-Ph,
33. 3-(3-thiophenyl)-Ph,
34. 4-(3-(iBu)-6-($SO_2NH_2$)-Ph)-Ph,
35. 4-(3-(iBu)-6-($SO_2NH_2$t-Bu)-Ph)-Ph,
36. 4-(4-(nBu)-Ph)-Ph,
37. 4-(3-(iBu)-6-($SO_2NHCO_2$nBu)-Ph)-Ph,
38. 3-(4-(n-Bu)-Ph)-Ph,
39. 4-(3-(n-Pr)-6-(tetrazol-5-yl)-Ph)-Ph,
40. 4-(5-n-Bu)-thiophenyl-Ph,
41. 2-F-4-(2-(5-n-Bu)-thiophenyl)-Ph,
42. 3,5-(2-thiophenyl)phenyl,
43. 3,4-(4-OMe-Ph)-Ph,
44. 3,5-(4-Me-Ph)-Ph,
45. 3,5-(4-SMe-Ph)-Ph,
46. 4-(NHCOMe)-Ph,
47. 4-($OCH_2CO_2Me$)-Ph,
48. 3,5-(di-Bromo)-Ph,
49. 4-(iPr)-Ph,
50. 4-(OBn)-Ph,
51. 2-(OPr)-Ph,
52. —CONHBn,
53. —CON-((4-benzyl)-piperidinyl),
54. —CONHPh,
55. —CO-(4-N-phenyl-piperizin-1-yl),
56. —CONH-((2-(2-indolyl)-phenyl),
57. —CONH-4-biphenyl,
58. —CONH-2-biphenyl,
59. 3,5-(3-nitrophenyl)-phenyl,
60. 4-(2-benzofuranyl)-phenyl,
61. 3-Br-5-(2-thiophenyl)-phenyl,
62. 4-(2-(5-Cl)-thiophenyl)-phenyl,
63. 4-(3,5-($CF_3$)-phenyl)-phenyl,
64. 4-(2-(OMe)-phenyl)-phenyl,
65. 4-(4-Cl-phenyl)-phenyl,
66. 4-($CO_2Me$)-phenyl,
67. 2-F-4-(2-thiophenyl)-phenyl,
68. 4-(3-($NH_2$)-phenyl)-phenyl,
69. 4-(3-(OMe)-phenyl)-phenyl,
70. 2,6-F-Ph,
71. —CONH-2-fluorenyl,
72. —CONH-(4-(n-octyl)-phenyl),
73. —CONH-adamantyl,
74. —CONH-c-hexyl,
75. —CONH-CH$(Bn)_2$,
76. —CONHCH$(Ph)_2$,
77. —CONH$CH_2$CH-$(Ph)_2$,
78. —CONH-2-tetrahydo-isoquinolinyl,
79. —$CO_2$Bn,
80. 3-(OBn)-Ph,
81. 4-(CHCH-Ph)-Ph,
82. 9-phenanthrenyl,
83. 3-(OPh)-Ph,
84. 2-(OMe)-Ph,
85. $CO_2$Et,
86. COOH,
87. 4-CN-Phenyl,
88. 2,4-F-Phenyl,
89. 2,4,6,-F-Phenyl,
90. 2-(3-OMe-Ph)-Ph,
91. 2-(3-$NO_2$-Ph)-Ph,
92. 2-(thiophen-2-yl)-Ph,
93. 2-(OEt)-Ph,
94. 2-(OH)-5-(Br)-Ph,
95. 2-(OMe)-5-(Br)-Ph,
96. 2,5-(OMe)-Ph,
97. 4-(tetrazol-5-yl)-Ph,
98. 2-F-(4-(Cl)-thiophen-2-yl)-Ph,
99. 4-(CONHtBu)-Ph,
100. 4-(N-methyl-tetrazol-5-yl)-Ph,
101. 2-(Cl)-4-(Br)-Ph,
102. 2-(ethoxy)-5-(Br)-Ph,
103. 2,5-F-Ph,
104. 2-(3-(Cl)-propoxy)-Ph,
105. 2-(propoxy)-5-(Br)-Ph,
106. 2-(F)-5-(Br)-Ph,
107. 4-(CON$(Bn_2)$)-Ph,
108. 4-(3-Pyr)-Ph,
109. 4-(CO-(N-Boc-piperazin)-Ph,
110. 4-(CON$Pn_2$)-Ph,
111. 4-(CO-morpholinyl)-Ph,
112. 4-(CO-L-proline-OtBu)-Ph,
113. 4-(CO-spiroindane-1)-Ph,
114. 4-(CO-spiroindene-1)-Ph,
115. 4-(CON$(Me)_2$)-Ph,
116. 4-(heterocycle-1)-Ph,
117. 4-(heterocycle-2)-Ph,
118. $CO_2$-(2-Ph-Ph),
119. CHCHPh,
120. 2-(OBn)-Ph,
121. 2-(O-hexyl)-Ph,
122. 2-(O-nonyl)-Ph,
123. 2-(O-iPr)-Ph,
124. 2-(O-iBu)-Ph,
125. 4-(2-pyr)-Ph,
126. 4-(2-$SO2NH_2$tBu-Ph)-2-F-Ph,
127. 4-$NO_2$-Ph,
128. 4-$NH_2$-Ph or
129. 4-(NH$CO_2$-butyl)-Ph wherein:

spiroindene-1 is:

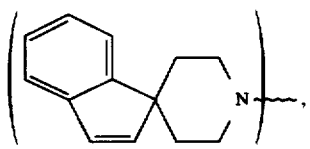

-continued heterocycle-1 is:

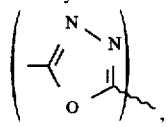

spiroindane-1 is:

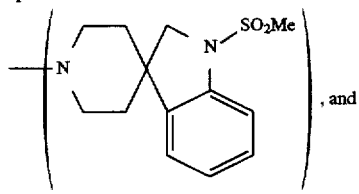, and heterocycle-2 is:

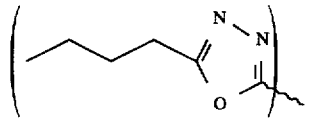

13. A compound of the formula:

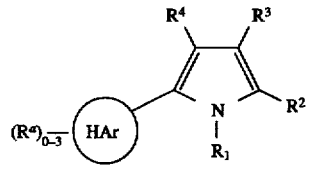

or a pharmaceutically acceptable salt thereof, wherein:

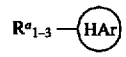

represents pyridyl substituted with 1–3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{23}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$, $C(NR^{20})NR^{20}R^{23}$; $C(O)OCH_2OC(O)R^{20}$; $CONR^{20}SO_2R^{21}$; and $SO_2NR^{20}CO_2R^{21}$, tetrazol-5-yl;

$R^1$ is selected from the group consisting of: H, aryl, $C_{1-15}$ alkyl, $C_{3-15}$ alkenyl, $C_{3-15}$ alkynyl; and heterocyclyl, said alkyl, aryl, alkenyl, alkynyl, and heterocyclyl being optionally substituted with from one to three members selected from the group consisting of: aryl, heteroaryl, heterocyclyl, halo, $OR^{20}$, $SR^{20}$, $N(R^{20})_2$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH2OC(O)R^{20}$;

$R^2$ is selected from the group consisting of: aryl, heteroaryl, heterocyclyl, $C_{2-15}$ alkenyl, $C_{2-15}$ alkynyl, said alkenyl and alkynyl group optionally interrupted by 1–2 heteroatoms selected from O, S, S(O), $SO_2$ or $NR^{24}$ and said, aryl, heteroaryl, heterocyclyl, alkyl, alkenyl, alkynyl being optionally substituted with from 1–3 of halo, aryl, heteroaryl, aryl$(R^a)_{1-2}$, $C_{1-15}$ alkyl, heteroaryl$(R^a)_{1-2}$, CN, $CF_3$, $NO_2$, heterocyclyl, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{21}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH_{20}C(O)R^{20}$;

$R^3$ is selected from the group consisting of: H, $C_{1-15}$ alkyl, aryl, $C_{2-15}$ alkenyl, $C_{2-15}$ alkynyl, halo, $NO_2$, $CO_2R^{22}$, CN, $CONR^{20}R^{23}$, $SO_2R^{21}$, $SO_2N(R^{20})_2$, $SO_2NR^{20}COR^{21}$, $SO_2NR^{20}CON(R^{20})_2$, $COR^{21}$, $CO_2R^{20}$, $CONR^{20}SO_2R^{21}$, $SO_2NR^{20}CO_2R^{21}$, and heterocyclyl, said alkyl, alkenyl, alkynyl, aryl, and heterocyclyl being optionally substituted with from one to three members selected from the group consisting of: halo, $C_{1-15}$ alkyl, $CF_3$, CN, aryl, $NO_2$, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OR^{20}$ and $OCONR^{20}R^{23}$;

$R^4$ is selected from the group consisting of $COR^{21}$, $CONR^{20}R^{23}$, aryl, heteroaryl, heterocyclyl, $C_{1-15}$ alkyl, $C_{3-15}$ alkenyl, $C_{3-15}$ alkynyl, said alkyl, alkenyl and alkynyl group optionally interrupted by 1–2 heteroatoms selected from O, S, S(O), $SO_2$ or $NR^{24}$ and said aryl, heteroaryl, heterocyclyl, $C_{3-15}$ alkenyl, $C_{3-15}$ alkynyl being optionally substituted with from 1–3 of $R^{21}$, halo, CN, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{21}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH2OC(O)R^{20}$; said alkyl being optionally substituted with aryl, heteroaryl, heterocyclyl, being optionally substituted with from 1–3 of $R^{21}$, halo, CN, $CF_3$, $NO_2$, $OR^{23}$, $SR^{23}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $CO_2R^{23}$, $COR^{21}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, $OCONR^{20}R^{23}$ and $C(O)OCH2OC(O)R^{20}$;

$R^{20}$ represents a member selected from the group consisting of: H, $C_{1-15}$ alkyl, $C_{3-15}$ alkenyl, $C_{3-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{3-15}$ alkenyl, $C_{3-15}$ alkynyl, aryl, heterocyclyl and heteroaryl; said alkyl, alkenyl or alkynyl being optionally interrupted by 1–2 heteroatoms selected from O, S, S(O), $SO_2$ or $NR^{24}$ and said alkyl, alkenyl, alkynyl, aryl, heterocyclyl and heteroaryl being optionally substituted with from 1–3 of halo, heterocyclyl, aryl, heteroaryl, aryl$(R^a)_{1-2}$, heteroaryl$(R^a)_{1-2}$, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{3-15}$ alkenyl, $C_{3-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$ and $SO_2R^{22}$;

n is 1–4;

m is 1–4;

and in a functional group substitutent wherein two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

14. A compound in accordance with claim 13 wherein:

$R^1$ is H, aryl, or $C_{1-15}$ alkyl, wherein H, aryl and $C_{1-15}$ alkyl are defined above;

R2 is aryl, heteroaryl, or heterocyclyl, wherein aryl, heteroaryl, or heterocyclyl are defined above;

$R^3$ is H, halo, $NO_2$, or CN; and $R^4$ is aryl, $C_{1-15}$ alkyl, heteroaryl, $COR^{21}$, $CONR^{20}R^{23}$ or heterocyclyl, wherein aryl, $C_{1-15}$ alkyl, heteroaryl, $COR^{21}$, $CONR^{20}R^{23}$ or heterocyclyl are defined above.

15. A compound in accordance with claim 13 wherein:

$R^1$ is H, or substituted alkyl;

$R^2$ is aryl, heteroaryl, or heterocyclyl; wherein aryl, heteroaryl, and heterocyclyl are defined above;

$R^4$ is aryl, $C_1$–$C_6$ alkyl, heteroaryl, heterocyclyl, or $CONR^{20}R^{23}$; wherein aryl, $C_1$–$C_6$ alkyl, heteroaryl, $R^{20}$ and $R^{23}$ and heterocyclyl are defined above;

R3 is H or halo; and

Har is pyridyl.

16. A compound in accordance with claim 13 wherein HAr is a) 4-pyridyl-,
b) (2-methyl-4-pyridyl)-,
c) (3-methyl-4-pyridyl)-,
d) (2-amino-4-pyridyl)-,
e) (2-benzylamino-4-pyridyl)-,
f) (2-acetylamino-4-pyridyl)-,
h) (4-(2-methoxy)-pyridyl)-, $R^1$ is H;

$R^2$ is phenyl substituted with:
a) Cl,
b) Br,
c) F,
d) $C_1$–$C_4$ alkyl,
e) $CF_3$,
f) O-($C_1$–$C_4$ alkyl),
g) $C_3$–$C_6$ cycloalkyl,
h) phenyl,
i) CN,
j) COOH,
k) $NO_2$,
l) alkyl-N(alkyl)$^2$,
m) NHCO-alkyl or
n) CONHalkyl;

$R^3$ is H $R^4$ is a) phenyl optionally substituted with:
1. 4-phenyl,
2. 3-phenyl,
3. 4-(2-thiophenyl),
4. 4-t-butyl,
5. 4-toluyl,
6. 4-(4-fluorophenyl)-,
7. 4-(3-nitro-phenyl)-,
8. 3-(3-nitro-phenyl)-,
9. 4-quinolinyl,
10. Cl,
11. OMe,
12. Br,
13. CF3,
14. cyclohexyl,
15. butyl,
16. (4-(2-tetrazol-5-yl)-phenyl)-,
17. 4-(3-thiophenyl)- or
18. 2-napthyl-;

b) 1. CONH-phenyl,
2. CONH-4-biphenyl,
3. $CH_2$-phenyl,
4. $CH_2$-4-(biphenyl), or
5. $CH_2$-4-(2'-carboxy-biphenyl).

17. A compound in accordance with claim 13 as set forth in the following table:

| $R^1$ | $R^2$ |
|---|---|
| H | 4-(SMe)—Ph |
| H | 4-(OPh)—Ph |
| H | 4-(OEt)—Ph |
| H | 4-(c-hex)-Ph |
| H | 4-($CF_3$)—Ph |
| H | 4-Br—Ph |
| H | 4-(tBu)—Ph |
| H | 4-Et—Ph |
| H | 4-(SPh)—Ph |
| H | 2-Me—Ph |
| H | 4-(OMe)—Ph |
| H | 4-Me—Ph |
| H | 4-Cl—Ph |
| H | 4-(OBu)—Ph |
| H | 4-(OBn)—Ph |
| H | 4-F—Ph |
| H | 3,4-Cl—Ph |
| H | 3-$CF_3$—Ph |
| H | 3,4-F—Ph |
| H | 3,4-($OCH_2O$)—Ph |
| H | 3-Cl-4-F—Ph |
| H | 3-Me-4-Cl—Ph |
| H | 4-$OCF_3$—Ph |

18. A compound according to claim 13, as set forth in the following table:

| | R⁴ | |
|---|---|---|
| HAr | | R² |
| | N | |
| | H | |

| HAr | R⁴ | R² |
|---|---|---|
| 4-Pyr | 4-CF₃—Ph | 4-Cl—Ph |
| 4-Pyr | 3-Cl—Ph | 4-Cl—Ph |
| 3-Pyr | 4-F—Ph | 4-Cl—Ph |
| 4-Pyr | 4-OMe—Ph | 4-Cl—Ph |
| 4-Pyr | 4-F—Ph | 4-NO₂—Ph |
| 4-Pyr | 4-F—Ph | 3-NO₂—Ph |
| 4-Pyr | 4-F—Ph | 2-NO₂—Ph |
| 4-Pyr | 4-F—Ph | 4-(COOEt)—Ph |
| 4-Pyr | 4-F—Ph | 4-CN—Ph |
| 4-Pyr. | 3-Br—Ph | 4-Cl—Ph |
| 4-Pyr | 4-(1-Napthyl)-Ph | 4-Cl—Ph |
| 4-Pyr | 4-F—Ph | 3-CN—Ph |
| 4-Pyr | 4-Br—Ph | 4-Cl—Ph |
| 4-Pyr | 3-Br—Ph | 4-Cl—Ph |
| 4-Pyr | 4-t-Bu—Ph | 4-Cl—Ph |

19. A compound according to claim 13, as set forth in the following table:
wherein

[Structure: pyrrole with 3-pyridyl at one position, R⁴ substituent, and 4-Cl-phenyl at the other, NH]

| R⁴ |
|---|
| 3-Ph—Ph— |
| 4-(4-MeO—Ph)—Ph— |
| 3-(4-MeO—Ph)—Ph— |
| 4-(4-CF₃—Ph)—Ph— |
| 4-(1-naphthyl)—Ph— |
| 4-(4-F—Ph)—Ph— |
| 4-(4-NO₂—Ph)—Ph— |
| 3-(3-NO₂—Ph)—Ph— |
| 4-(4-Me—Ph)—Ph— |
| 4-(2-thiophenyl)-Ph— |
| 4-(3-thiophenyl)-Ph— |
| 3-(2-thiophenyl)-Ph— |
| 3-(3-thiophenyl)-Ph— |

20. A compound according to claim 13 as set forth in the following table:

[Structure I: (Rᵃ)₀₋₃—HAr—pyrrole (N-R¹) with R³, R⁴, R²]

| R¹ | R² | R³ | R⁴ | HAR-(Rᵃ)₀₋₃ |
|---|---|---|---|---|
| H | 4-(COOH)—Ph | H | 4-F—Ph | 4-Pyr |
| H | 4-Cl—Ph | H | 4-tBu—Ph | 4-Pyr |
| H | 4-Cl—Ph | H | 4-(3(i-Bu)-6-(A)Ph)Ph | 4-Pyr |
| H | 4-Cl—Ph | H | 4-(4-(n-Bu)—Ph)—Ph | 4-Pyr |
| H | 4-Cl—Ph | H | 4-(3-(iBu)-6-(B)—Ph)Ph | 4-Pyr |
| H | 4-Cl—Ph | H | 4-(3-(iBu)-6-(C)Ph)Ph | 4-Pyr |
| H | 4-Cl—Ph | H | 3-(4-(n-Bu)—Ph)—Ph | 4-pyr |
| H | 4-Cl—Ph | H | 4-(3-(n-Pr)-6-(D)Ph)Ph | 4-pyr |
| H | 4-Cl—Ph | H | 4-(5-(n-Bu)-thioPh)—Ph | 4-Pyr |
| H | 4-Cl—Ph | H | 2-F-4-Br-phenyl | 4-Pyr |
| H | 4-Cl—Ph | H | 2-(F)-4-(E)—Ph | 4-Pyr |
| H | 4-Cl—Ph | Br | 4-F-Phenyl | 4-Pyr |
| H | 4-Cl—Ph | Cl | 4-F-phenyl | 4-Pyr |
| H | 4-Cl—Ph | H | 3,5-(Br)-phenyl | 4-pyr |
| H | 4-Cl—Ph | H | 3,5-(2-thiophenyl)-Ph | 4-pyr |
| H | 4-Cl—Ph | H | CO₂Et | 4-Pyr |
| H | 4-Cl—Ph | H | COOH | 4-Pyr |
| H | 4-Cl—Ph | H | 3,4-(4-OMe—Ph)—Ph | 4-Pyr |
| H | 4-Cl—Ph | H | 3,5-(4-Me—Ph)—Ph | 4-Pyr |
| H | 4-Cl—Ph | H | 3,5-(4-SMe—Ph)—Ph | 4-Pyr |
| H | 4-Cl—Ph | H | 4-(NHCOMe)—Ph | 4-Pyr |
| H | 4-Cl—Ph | H | 4-(OCH2CO₂Me)—Ph | 4-Pyr |
| H | 4-Cl—Ph | H | 4-(OMe)—Ph | 4-Pyr |
| H | 4-Cl—Ph | H | 4-(iPr)—Ph | 4-Pyr |
| H | 4-Cl—Ph | H | 4-(OBn)—Ph | 4-Pyr |
| H | 4-Cl—Ph | H | 2-(OPr)—Ph | 4-Pyr |
| H | 4-Cl—Ph | H | CO-(4-(N—Ph)—Z) | 4-Pyr |
| H | 4-Cl—Ph | H | CONH-2-biphenyl | 4-Pyr |
| H | 4-Cl—Ph | H | 3,5,-(3-nitro-phenyl)-Ph | 4-Pyr |
| H | 4-Cl—Ph | H | 4-(2-benzo-furanyl)-Ph | 4-Pyr |
| H | 4-Cl—Ph | H | 3-Br-5-(24hioPh)—Ph | 4-Pyr |
| H | 4-Cl—Ph | H | 4-(G)—Ph | 4-Pyr |
| H | 4-Cl—Ph | H | 4-(3,5-(CF3)—Ph)—Ph | 4-Pyr |
| H | 4-Cl—Ph | H | 4-(2-(OMe)—Ph)—Ph | 4-Pyr |
| H | 4-Cl—Ph | H | 4-(4-Cl-phenyl)-phenyl | 4-Pyr |
| H | 4-Cl—Ph | H | 4-(CO₂Me)-phenyl | 4-Pyr |
| H | 4-Cl—Ph | H | 2-F-4-(2-thioPh)—Ph | 4-Pyr |
| H | 4-Cl—Ph | H | 4-(3-(NH2)—Ph)—Ph | 4-Pyr |
| H | 4-Cl—Ph | H | 4-(3-(OMe)—Ph)—Ph | 4-Pyr |
| H | 4-Cl—Ph | H | 2-Br—Ph | 4-Pyr |
| H | 4-Cl—Ph | H | 2,6-F—Ph | 4-Pyr |
| H | 4-Cl—Ph | H | CONH-adamantyl | 4-Pyr |
| H | 4-Cl—Ph | H | CONHCH₂CH(Ph)₂ | 4-Pyr |
| [H | 4-Cl—Ph | H | 4-F—Ph | 4-quinolinyl] |
| H | 4-Cl—Ph | H | CO₂Bn | 4-Pyr |
| H | 4-Cl—Ph | H | 3-OBn—Ph | 4-Pyr |
| H | 4-Cl—Ph | H | 4-(CHCH—Ph)—Ph | 4-Pyr |
| H | 4-Cl—Ph | H | 9-phenanthrenyl | 4-Pyr |
| H | 4-Cl—Ph | H | 3-(OPh)—Ph | 4-Pyr |
| H | 4-Cl—Ph | H | 2-(OMe)—Ph | 4-Pyr |
| H | 2,4-Cl—Ph | H | 4-F—Ph | 4-Pyr |
| H | 4-(N-CBz)—Z | H | 4-F—Ph | 4-Pyr |
| H | 4-Ph—Ph | H | 4-F—Ph | 4-Pyr |
| H | 4-Cl-phenyl | H | 4-CN-phenyl | 4-pyr |
| H | 4-Cl—Ph | H | 2,4-F-Phenyl | 4-Pyr |
| H | 4-Cl-phenyl | H | 2,4,6-F-phenyl | 4-Pyr |
| H | 4-Cl-phenyl | H | 2-(3-OMe—Ph)—Ph | 4-Pyr |
| H | 4-Cl-phenyl | H | 2-(3-NO₂—Ph)—Ph | 4-Pyr |
| H | 4-Cl-phenyl | H | 2-(thiophen-2-yl)-Ph | 4-Pyr |
| H | 4-Cl-phenyl | H | 2-(OEt)—Ph | 4-Pyr |
| H | 4-Cl-phenyl | H | 2-(OH)-5-(Br)—Ph | 4-pyr |
| H | 4-Cl-phenyl | H | 2-(OMe)-5-(Br)—Ph | 4-pyr |
| H | 4-Cl-phenyl | H | 2,5-(OMe)—Ph | 4-pyr |
| H | 3-Cl-phenyl | H | 4-F—Ph | 4-Pyr |
| H | 4-F-phenyl | H | 4-F—Ph | 4-pyr |
| H | 4-Cl-phenyl | H | 4-(tetrazol-5-yl)-Ph | 4-Pyr |
| H | 4-F—Ph | H | 4-(2-thiophenyl)-Ph | 4-Pyr |
| H | 2-F-phenyl | H | 4-F-phenyl | 4-Pyr |

-continued

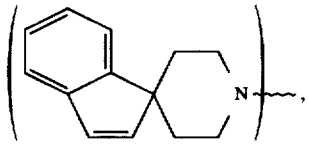

| R¹ | R² | R³ | R⁴ | HAR-(Rᵃ)₀₋₃ |
|---|---|---|---|---|
| H | 4-Cl-phenyl | H | 2-F-4-(G)—Ph | 4-Pyr |
| H | 4-Cl-phenyl | H | 4-(CONHtBu)—Ph | 4-Pyr |
| H | 2-(OMe)-4-(Cl)Ph | H | 4-F—Ph | 4-pyr |
| H | 4-Cl-phenyl | H | 4-F—Ph | 4-(2,6-phenyl)-pyr |
| H | 4-Cl-phenyl | H | 4-F—Ph | 4-(2-F)-pyr |
| H | 4-Cl-phenyl | H | 4-(J)Ph | 4-pyr |
| H | 4-Cl-phenyl | H | 2-(Cl)-4-(Br)—Ph | 4-pyr |
| H | 4-Cl-phenyl | H | 4-(CO₂Et)—Ph | 4-pyr |
| H | 4-N-(acetyl)-Z | H | 4-F—Ph | 4-Pyr |
| H | 4-N-(Me)—Z | H | 4-F—Ph | 4-Pyr |
| H | 4-N(OMe—CO)Z | H | 4-F—Ph | 4-Pyr |
| H | 4-N-(iPr—CO)Z | H | 4-F—Ph | 4-Pyr |
| H | 4-piperidinyl | H | 4-F—Ph | 4-Pyr |
| H | 4-Cl-phenyl | H | 4-F—Ph | 3-F-4-pyr |
| H | 4-Cl-phenyl | H | 4-F—Ph | 3-(Me)-4-pyridyl |
| H | 4-Cl-phenyl | H | 2-(ethoxy)-5-(Br)—Ph | 4-pyr |
| H | 4-Cl-phenyl | H | 2,5-(F)—Ph | 4-pyr |
| H | 4-Cl-Phenyl | H | 2-(3-(Cl)-propoxy)—Ph | 4-Pyr |
| H | 4-Cl-phenyl | H | 2-(propoxy)-5-(Br)—Ph | 4-Pyr |
| H | 4-Cl-Phenyl | H | 2-(F)-5-(Br)—Ph | 4-Pyr |
| H | 4-Cl-Phenyl | H | 4-(CON(Bn₂))—Ph | 4-Pyr |
| H | 4-Cl-phenyl | H | 4-(3-Pyr)-Ph | 4-Pyr |
| H | 4-Cl-phenyl | H | 4-(CO—(M))Ph | 4-pyr |
| H | 4-Cl-phenyl | H | 4-(CONPn₂)—Ph | 4-pyr |
| H | 4-Cl-phenyl | H | 4-(CO-morpholinyl)-Ph | 4-pyr |
| H | 4-Cl-phenyl | H | 4-(W)Ph | 4-Pyr |
| H | 4-Cl-phenyl | H | 4-(Q)Ph | 4-pyr |
| H | 4-Cl-phenyl | H | 4-(CO-spiroindene-1)-Ph | 4-Pyr |
| H | 4-Cl-phenyl | H | 4-(CONMe₂)—Ph | 4-pyr |
| H | 4-Cl-phenyL | H | 4-(heterocycle-1)-Ph | 4-pyr |
| H | 4-Cl-phenyl | H | 4-(heterocycle-2)-Ph | 4-Pyr |
| H | 4-Cl-phenyl | H | CO₂-(2-Ph—Ph) | 4-pyr |
| H | 4-Cl-phenyl | H | 4-F—Ph | 4-(2-methyl)pyridyl |
| H | 4-Cl-phenyl | H | CHCHPh | 4-pyr |
| H | 4-Cl-phenyl | H | 2-(CHCH—Ph)—Ph | 4-pyr |
| H | 4-Cl-phenyl | H | 2-(OBn)—Ph | 4-pyr |
| H | 4-Cl-phenyl | H | 2-(G-hexyl)-Ph | 4-Pyr |
| H | 4-Cl-phenyl | H | 2-(O-nonyl)-Ph | 4-pyr |
| H | 4-Cl-phenyl | H | 2-(O-iPr)—Ph | 4-pyr |
| H | 4-Cl-phenyl | H | 2-(O-iBu)—Ph | 4-pyr |
| H | 4-Cl-phenyl | H | 4-(2-pyr)-Ph | 4-pyr |
| (X) | 4-Cl-phenyl | H | 2-F-4-Br-phenyl | 4-pyr |
| H | 4-Cl-phenyl | H | 4-(Y)-2-F—Ph | 4-pyr |
| H | 4-Cl-phenyl | H | 4-NO₂—Ph | 4-pyr |
| H | c-hexyl | H | 4-F-phenyl | 4-pyr |
| H | N-(CBz)(Z) | H | CO₂Et | 4-pyr |
| H | 4-Cl-phenyl | H | 4-NH₂—Ph | 4-pyr |
| H | 4-Cl-phenyl | H | 4-(NHCO₂-butyl)-Ph | 4-pyr | wherein: CO=carbonyl, Ph=phenyl, pyr=pyridyl, Pip=piperidinyl, OMe=methoxy, iPr=isopropyl, thioPh-thiophenyl, (A)=SO₂NH₂tBu, (B)=SO₂NH₂, (C)=SO₂NHCO₂nBu, (D)=tetrazol-5-yl, (E)=5-(n-Bu)-thiophen-2-yl, (G)=5-(Cl)-thiophen-2-yl, (J)=N-methyltetrazolyl, (M)=N-Boc-piperazin, (Q)=CO-spiroindane-1, (W)=CO-L-proline-OtBu, (X)=2-OH-Ph, (Y)=2-SO₂NH₂tBu-Ph, (Z)=piperidin-4-yl, spiroindene-1 is:

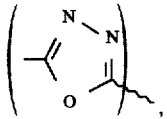

heterocycle-1 is:

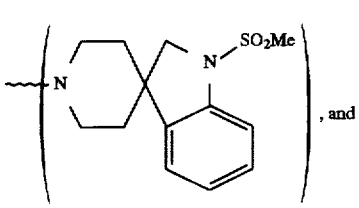

spiroindane-1 is:

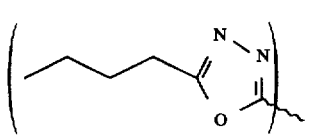

, and heterocycle-2 is:

21. A compound according to claim 1 which is:

3-(4-chlorophenyl)-5-(4-chlorophenyl)-2-(4-pyridyl)-pyrrole;

5-(4-chlorophenyl)-3-(4-fluorophenyl)-2-(2-pyridyl)-pyrrole;

5-(4-methylsulfinylphenyl)-3-(4-fluorophenyl)-2-(4-pyridyl)-pyrrole;

5-(4-methylaminophenyl)-3-(4-fluorophenyl)-2-(4-pyridyl)-pyrrole;

5-(4-aminophenyl)-3-(4-fluorophenyl)-2-(4-pyridyl)-pyrrole;

5-(3-aminophenyl)-3-(4-fluorophenyl)-2-(4-pyridyl)-pyrrole;

5-(2-aminophenyl)-3-(4-fluorophenyl)-2-(4-pyridyl)-pyrrole 5-(N-methyl-piperidin-4-yl)-3-(4-fluorophenyl)-2-(4-pyridyl)-pyrrole;

5-(4-chlorophenyl)-3-(biphenyl)-2-(4-pyridyl)-pyrrole;

3-(4-fluorophenyl)-5-(4-phenylsulfinylphenyl)-2-(4-pyridyl)pyrrole or 5-(N-methyl-piperidin-4-yl)-3-(4-fluorophenyl)-2-(4-pyridyl)pyrrole.

22. A compound in accordance with one of the following tables:

101

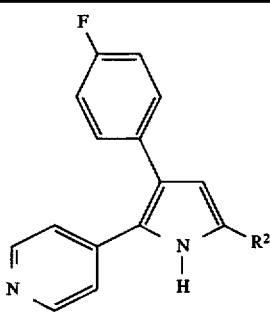

| Compound # | R² |
|---|---|
| 1 | 4-(MeS)—Ph |
| 2 | 4-(PhO)—Ph |
| 3 | 4-(EtO)—Ph |
| 4 | 4-(c-hex)-Ph |
| 5 | 4-(CF₃)—Ph |
| 6 | 4-Br—Ph |
| 7 | 4-(t-Bu)—Ph |
| 8 | 4-Et—Ph |
| 9 | 4-(PhS)—Ph |
| 10 | 2-Me—Ph |
| 11 | 4-(MeO)—Ph |
| 12 | 4-Me—Ph |
| 13 | 4-Cl—Ph |
| 14 | 4-(n-BuO)—Ph |
| 15 | 4-(BzlO)—Ph |
| 16 | 4-F—Ph |
| 17 | 3,4-di-Cl—Ph |
| 18 | 3-CF₃—Ph |
| 19 | 3,4-di-F—Ph |
| 20 | 3,4-(OCH₂O)—Ph |
| 21 | 3-Cl-4-F—Ph |

102

-continued

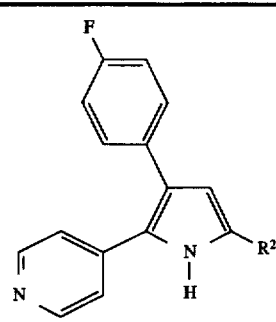

| Compound # | R² |
|---|---|
| 22 | 3-Me-4-Cl—Ph |
| 23 | 4-CF₃O—Ph |

Me=methyl c-hex=cyclohexyl t-Bu=t-butyl Ph=phenyl Et=ethyl Bzl=benzyl Cbz=carboxybenzyl 3,4-(OCH₂O)-Ph represents

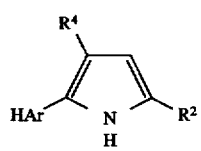

TABLE

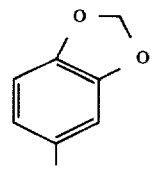

| Cp. # | R² | R⁴ | HAr |
|---|---|---|---|
| 25 | 4-Cl-Ph | 4-CF₃-Ph | 4-Pyr |
| 26 | 4-Cl-Ph | 3-Cl-Ph | 4-Pyr |
| 27 | 4-Cl-Ph | 4-F-Ph | 3-Pyr |
| 28 | 4-Cl-Ph | 4-MeO-Ph | 4-Pyr |
| 29 | 4-NO₂-Ph | 4-F-Ph | 4-Pyr |
| 30 | 3-NO₂-Ph | 4-F-Ph | 4-Pyr |
| 31 | 2-NO₂-Ph | 4-F-Ph | 4-Pyr |
| 32 | 4-(CO₂Et)-Ph | 4-F-Ph | 4-Pyr |
| 33 | 4-CN-Ph | 4-F-Ph | 4-Pyr |
| 34 | 4-Cl-Ph | 3-Br-Ph | 4-Pyr |
| 35 | 4-Cl-Ph | 4-(1-naphthyl)-Ph | 4-Pyr |
| 36 | 3-CN-Ph | 4-F-Ph | 4-Pyr |
| 37 | 4-Cl-Ph | 4-Br-Ph | 4-Pyr |
| 38 | 4-Cl-Ph | 4-t-Bu-Ph | 4-Pyr |
| 39 | 4-Cl-Ph | 2-F-4-Br-Ph | 4-Pyr |

TABLE-continued
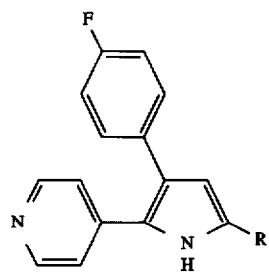
| Compound # | R |
|---|---|
| 44 | 4-NH$_2$-Ph |
| 45 | 3-NH$_2$-Ph |
| 46 | 2-NH$_2$-Ph |
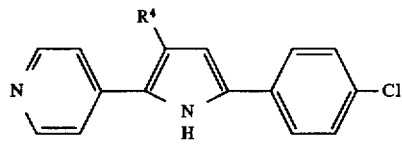
| Compound # | R$^4$ |
|---|---|
| 50 | 3-Ph-Ph- |
| 51 | 4-(4-MeO-Ph)-Ph- |
| 52 | 3-(4-MeO-Ph)-Ph- |
| 53 | 4-(4-CF$_3$-Ph)-Ph- |
| 54 | 4-(4-F-Ph)-Ph- |
| 55 | 4-(3-NO$_2$-Ph)-Ph- |
| 56 | 3-(3-NO$_2$-Ph)-Ph- |
| 57 | 4-(4-Me-Ph)-Ph- |
| 58 | 4-(2-thiophenyl)-Ph- |
| 59 | 4-(3-thiophenyl)-Ph- |
| 60 | 3-(2-thiophenyl)-Ph- |
| 61 | 3-(3-thiophenyl)-Ph- |
65 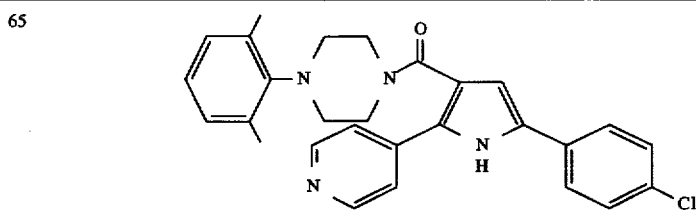
66 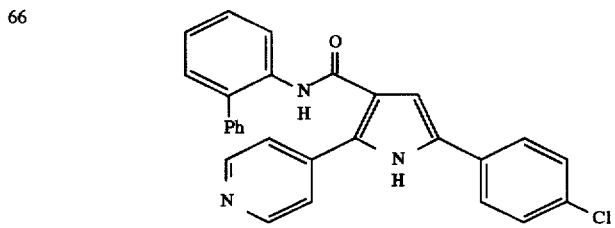
67 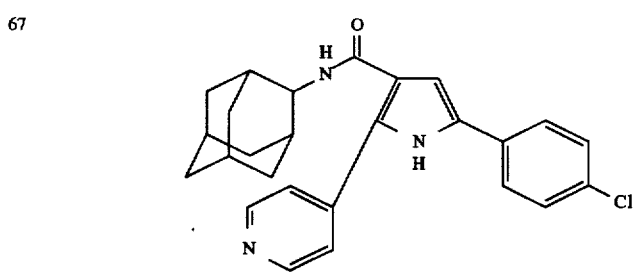

TABLE-continued

68

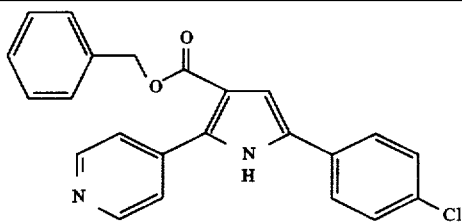

69

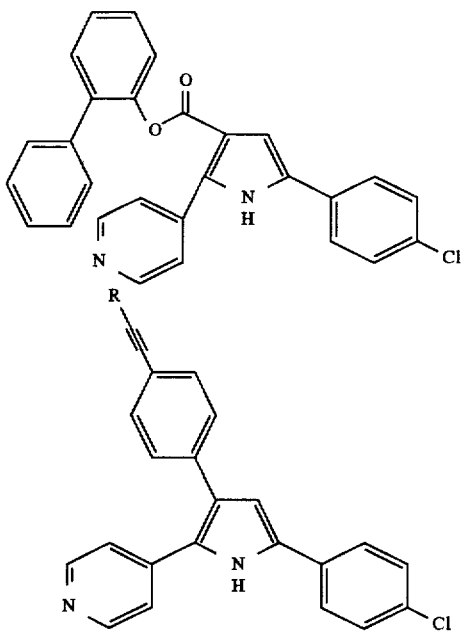

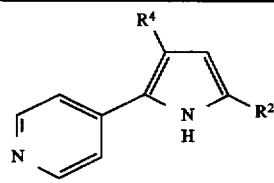

| Expl. No. | R |
|---|---|
| 73 | H |
| 74 | phenyl |
| 75 | n-butyl |
| 76 | 4-methyl-phenyl |
| 77 | 4-Cl-phenyl |
| 78 | 2-pyridyl |
| 79 | 4-F-phenyl |
| 80 | 4-ethylphenyl |
| 81 | 4-butylphenyl |

| Cp. No. | $R^2$ | $R^4$ |
|---|---|---|
| 82 | 4-(COOH)-Ph | 4-F-Ph |
| 83 | 4-Cl-Ph | 4-(3-(i-Bu)-6-($SO_2$NH-t-Bu)-phenyl)-Ph |
| 84 | 4-Cl-Ph | 4-(4-(n-Bu)-phenyl)-Ph |
| 85 | 4-Cl-Ph | 4-(3-(iBu)-6-($SO_2NH_2$)-phenyl)-Ph |
| 86 | 4-Cl-Ph | 3-(4-(n-Bu)-phenyl)-Ph |
| 87 | 4-Cl-Ph | 4-(5-(n-Bu)-thiophenyl)-Ph |
| 88 | 4-Cl-Ph | 2-(F)-4-(5-(n-Bu)-thiophen-2-yl)-Ph |
| 89 | 4-Cl-Ph | 3,5-di-Br-Ph |
| 90 | 4-Cl-Ph | 3,5-(thiophen-2-yl)-Ph |
| 91 | 4-Cl-Ph | 3,4-di-(4-OMe-Ph)-Ph |
| 92 | 4-Cl-Ph | 3,5-di-(4-Me-Ph)-Ph |
| 93 | 4-Cl-Ph | 4-($OCH_2CO_2$Me)-Ph |
| 94 | 4-Cl-Ph | 4-OMe-Ph |
| 95 | 4-Cl-Ph | 4-i-Pr-Ph |

TABLE-continued

| | | |
|---|---|---|
| 96 | 4-Cl-Ph | 4-OBzl-Ph |
| 97 | 4-Cl-Ph | 5-Ph-thiazol-2-yl |
| 98 | 4-Cl-Ph | 4-Br-thiophen-2-yl |
| 99 | 4-Cl-Ph | 2-OPr-Ph |
| 100 | 4-Cl-Ph | 3-thiophenyl |
| 101 | 4-Cl-Ph | 3,5-di-(3-nitrophenyl)-Ph |
| 102 | 4-Cl-Ph | 4-(benzofuran-2-yl)-phenyl |
| 103 | 4-Cl-Ph | 3-Br-5-(thiophen-2-yl)-Ph |
| 104 | 4-Cl-Ph | 4-(5-Cl-thiophen-2-yl)-Ph |
| 105 | 4-Cl-Ph | 4-(3,5-di-CF$_3$-Ph)-Ph |
| 106 | 4-Cl-Ph | 4-(2-OMe-Ph)-Ph |
| 107 | 4-Cl-Ph | 4-(4-Cl-Ph)-Ph |
| 108 | 4-Cl-Ph | 4-(CO$_2$Me)-Ph |
| 109 | 4-Cl-Ph | 2-F-4-(thiophen-2-yl)-Ph |
| 110 | 4-Cl-Ph | 4-(3-(NH$_2$)-Ph)-Ph |
| 111 | 4-Cl-Ph | 4-(3-(OMe)-Ph)-Ph |
| 112 | 4-Cl-Ph | 2-Br-Ph |
| 113 | 4-Cl-Ph | 2,6-di-F-Ph |
| 114 | 4-Cl-Ph | 3-OBnzl-Ph |
| 115 | 4-Cl-Ph | 4-(trans-ethenyl-Ph)-Ph |
| 116 | 4-Cl-Ph | 9-phenanthrenyl |
| 117 | 4-Cl-Ph | 3-(OPh)-Ph |
| 118 | 4-Cl-Ph | 2-(OMe)-Ph |
| 119 | 2,4-di-Cl-Ph | 4-F-Ph |
| 120 | t-Bu | 4-F-Ph |
| 121 | Me | 4-F-Ph |
| 122 | 4-Cl-Ph | 4-CN-Ph |
| 123 | 4-Cl-Ph | 2,4-di-F-Ph |
| 124 | 4-Cl-Ph | 2,4,6-tri-F-Ph |
| 125 | 4-Cl-Ph | 2-(3-OMe-Ph)-Ph |
| 126 | 4-Cl-Ph | 2-(3-NO$_2$-Ph)-Ph |
| 127 | 4-Cl-Ph | 2-thiophen-2-yl-Ph |
| 128 | 4-Cl-Ph | 2-indolyl |
| 129 | 4-Cl-Ph | 2-OEt-Ph |
| 130 | 4-Cl-Ph | 2-OH-5-Br-Ph |
| 131 | 4-Cl-Ph | 2-OMe-5-Br-Ph |
| 132 | 4-Cl-Ph | 5-(2-(CO$_2$Me)-thiophen-3-yl)-furan-2-yl |
| 133 | 4-Cl-Ph | 2,5-di-OMe-Ph |
| 134 | 3-Cl-Ph | 4-F-Ph |
| 135 | 4-F-Ph | 4-F-Ph |
| 136 | 4-Cl-Ph | 4-(tetrazol-5-yl)-Ph |
| 137 | 4-F-Ph | 4-(2-thiophenyl)-Ph |
| 138 | 2-F-Ph | 4-F-Ph |
| 139 | 4-Cl-Ph | 2-F-4-(2-(5-Cl-thiophen-2-yl)-Ph |
| 140 | 4-Cl-Ph | 4-(CONH-t-Bu)-Ph |
| 141 | 2-OMe-4-Cl-Ph | 4-F-Ph |
| 142 | 4-Cl-Ph | 4-(N-methyltetrazolyl)-Ph |
| 143 | 4-Cl-Ph | 2-Cl-4-Br-Ph |
| 144 | 4-Cl-Ph | 4-(CO$_2$Et)-Ph |
| 145 | 4-N-acetyl-piperidinyl | 4-F-Ph |
| 146 | 4-N-(methoxycarbonyl)-piperidinyl | 4-F-Ph |
| 147 | 4-N-(isopropoxycarbonyl)-piperidinyl | 4-F-Ph |
| 148 | 4-piperidinyl | 4-F-Ph |
| 149 | 4-Cl-Ph | 2-ethoxy-5-Br-Ph |
| 150 | 4-Cl-Ph | 2,5-di-F-Ph |
| 151 | 4-Cl-Ph | 2-(3-Cl-propoxy)-Ph |
| 152 | 4-Cl-Ph | 2-propoxy-5-Br-Ph |
| 153 | 4-Cl-Ph | 2-F-5-Br-Ph |
| 154 | 4-Cl-Ph | 4-C(O)N(Bzl)$_2$-Ph |
| 155 | 4-Cl-Ph | 4-(3-Pyr)-Ph |
| 156 | 4-Cl-Ph | 4-C(O)-(N-Boc-piperazinyl))-Ph |
| 157 | 4-Cl-Ph | 4-(C(O)NPh$_2$)-Ph |
| 158 | 4-Cl-Ph | 4-C(O)-morpholinyl)-Ph |
| 159 | 4-Cl-Ph | 4-(C(O)-L-proline-O-(t-Bu))-Ph |
| 160 | 4-Cl-Ph | 4-C(O)-spiroindene)-phenyl |
| 161 | 4-Cl-Ph | 4-(5-Me-1,3,4-oxadiazol-2-yl)-Ph |
| 162 | 4-Cl-Ph | 4-(5-(n-Bu)-1,3,4-oxadiazol-2-yl)-Ph |
| 163 | 4-Cl-Ph | trans-ethenyl-Ph |
| 164 | 4-Cl-Ph | 2-(t-CHCH-Ph)-Ph |
| 165 | 4-Cl-Ph | 2-(OBzl)-Ph |
| 166 | 4-Cl-Ph | 2-(O-(n-hexyl))-Ph |
| 167 | 4-Cl-Ph | 2-(O-(n-nonyl))-Ph |
| 168 | 4-Cl-Ph | 2-(O-iPr)-Ph |
| 169 | 4-Cl-Ph | 2-(O-iBu)-Ph |
| 170 | 4-Cl-Ph | 2-(O-(n-butyl))-Ph |
| 171 | 4-Cl-Ph | 2-(O-allyl)-Ph |
| 172 | 4-Cl-Ph | 2-(OCH$_2$-(2,6-di-Cl-Ph))-Ph |
| 173 | 4-Cl-Ph | 4-(2-pyr)-Ph |
| 174 | 4-Cl-Ph | 4-(2-(SO$_2$NH-(t-Bu))-Ph)-2-F-Ph |

TABLE-continued

| | | |
|---|---|---|
| 175 | 4-Cl-Ph | 4-NO$_2$-Ph |
| 176 | c-hexyl | 4-F-Ph |
| 177 | N-(CBzl)-piperidin-4-yl | CO$_2$Et |
| 178 | 4-Cl-Ph | 4-NH$_2$-Ph |
| 179 | 4-Cl-Ph | 4-(NHCO$_2$-(n-butyl))-Ph |
| 180 | 4-Cl-Ph | 4-(NHSO$_2$-(n-butyl))-Ph |
| 181 | 4-Cl-Ph | 4-(NHSO$_2$-thiophen-2-yl)-Ph |
| 182 | 4-Cl-Ph | 2-(OC(O)-propyl)-Ph |
| 183 | 4-Cl-Ph | 2-(O(CH$_2$)$_3$SMe)-Ph |
| 184 | 4-Cl-Ph | 4-(NHCO$_2$Bzl)-Ph |
| 185 | 4-Cl-Ph | 4-(NHCO$_2$Ph)-Ph |
| 186 | N-(COOCH$_2$Ph-4-Cl)-piperidin-4-yl | 4-F-Ph |
| 187 | N-(COOCH$_2$Ph-4-Br)-piperidin-4-yl | 4-F-Ph |
| 188 | N-(COOCH$_2$Ph-4-Ph)-piperidin-4-yl | 4-F-Ph |
| 189 | N-(COOCH$_2$Ph-4-NO$_2$)-piperidin-4-yl | 4-F-Ph |
| 190 | N-(COOCH$_2$Ph-3-Cl)-piperidin-4-yl | 4-F-Ph |
| 191 | N-(COOCH$_2$Ph-2,4,5-tri-OMe)-piperidin-4-yl | 4-F-Ph |
| 192 | N-(COOCH$_2$Ph-2-Cl)-piperidin-4-yl | 4-F-Ph |
| 193 | 4-NHCO$_2$Bzl-cyclohexyl | 4-F-Ph |
| 194 | N-(COOCH$_2$Ph)-piperidin-3-yl | 4-F-Ph |
| 195 | 4-NH$_2$-cyclohexyl | 4-F-Ph |
| 196 | piperidin-3-yl | 4-F-Ph |
| 197 | 4-Cl-Ph | 2-OH-Ph |
| 198 | 4-Cl-Ph | 2-(4-Cl-SPh)-Ph |
| 199 | 4-Cl-Ph | 2-OPh-Ph |
| 200 | 4-Cl-Ph | 2-(O(CH$_2$)$_3$OMe)-Ph |
| 201 | 4-Cl-Ph | 2-(OCONMe$_2$)-Ph |
| 202 | 4-Cl-Ph | 2-(S-t-Bu)-Ph |
| 203 | 4-Cl-Ph | 4-(O(n-Pr))-Ph |
| 204 | 4-Cl-Ph | 2-(O(n-Pr))-4-(Br)-Ph |
| 205 | 4-Cl-Ph | 4-(5-((CH$_2$)$_4$OH)-thiophen-2-yl)-Ph |
| 206 | 4-Cl-Ph | 4-(5-((CH$_2$)$_4$-azido)-thiophen-2-yl)-Ph |
| 207 | 4-Cl-Ph | 4-(3-OMe-Ph)-2-(O(n-Pr))-Ph |
| 208 | 4-Cl-Ph | 3-(O(n-Pr))-Ph |
| 209 | 4-Cl-Ph | 4-(3-NH$_2$-Ph)-2-(O(n-Pr))-Ph |
| 210 | 4-Cl-Ph | benzyl |
| 211 | 4-Cl-Ph | 2-(furan-2-yl)-Ph |
| 212 | 4-Cl-Ph | 4-(furan-2-yl)-Ph |
| 213 | 4-Cl-Ph | 4-(2-OH-5-Br-Ph)-2-(O(n-Pr))-Ph |
| 214 | 4-Cl-Ph | 4-(5-((n-Bu))-thiophen-2-yl)-2-(O(n-Pr))-Ph |
| 215 | 4-Cl-Ph | 4-(3-(O(n-Bu))-Ph)-Ph |
| 216 | 4-Cl-Ph | 4-(5-((CH$_2$)$_4$-amino)-thiophen-2-yl)-Ph |
| 217 | 4-Cl-Ph | 4-((n-Bu))-thiophen-2-yl)-Ph |
| 218 | 4-Cl-Ph | 1-naphthyl |
| 219 | 4-Cl-Ph | quinolin-8-yl |
| 220 | 4-Cl-Ph | 4-(2-(OMe)-5-Br-Ph)-2-(O(n-Pr))-Ph |
| 221 | 4-Cl-Ph | 4-(cyclohexyl)-Ph |
| 222 | 4-Cl-Ph | 4-(n-Bu)-Ph |
| 223 | 4-Cl-Ph | 4-(5-(NO$_2$)-thiophen-2-yl)-Ph |
| 224 | 4-Cl-Ph | 4-(3-(Me)-thiophen-2-yl)-Ph |
| 225 | 4-Cl-Ph | 4-(2,5-di-OMe-Ph)-Ph |
| 226 | 4-Cl-Ph | 4-(2,4,6-tri-Me-Ph)-Ph |
| 227 | 4-Cl-Ph | 4-(5-ethyl-thiophen-2-yl)-Ph |
| 228 | 4-Cl-Ph | 4-(5-Me-thiophen-2-yl)-Ph |
| 229 | 4-Cl-Ph | 4-(5-(n-Pr)-thiophen-2-yl)-Ph |
| 230 | 4-Cl-Ph | 4-(4-(n-Pr)-Ph)-Ph |
| 231 | 4-Cl-Ph | 4-I-Ph |
| 232 | 4-Cl-Ph | 4-(5-OMe-pyridin-2-yl)-Ph |
| 233 | 4-Cl-Ph | 4-(3-Me-Ph)-Ph |
| 234 | 4-Cl-Ph | 4-(3,4-methylenedioxy)-Ph)-Ph |
| 235 | 4-Cl-Ph | 4-(3-(propoxy)-Ph)-Ph |
| 236 | 4-Cl-Ph | 4-(3-acetyl-Ph)-Ph |
| 237 | 4-Cl-Ph | 4-(3-NO$_2$-4-Me-Ph)-Ph |
| 238 | 4-Cl-Ph | 4-(3,4-di-OMe-Ph)-Ph |
| 239 | 4-Cl-Ph | 4-(3-(OCH$_2$CH$_2$OMe)-Ph)-Ph |
| 240 | 4-Cl-Ph | 4-(4-CN-3-Me-Ph)-Ph |
| 241 | 4-Cl-Ph | 4-(5-acetyl-thiophen-2-yl)-Ph |
| 242 | 4-Cl-Ph | CH$_2$CH$_2$-Ph |
| 243 | 4-Cl-Ph | CH$_2$CH(Me)-Ph |
| 244 | 4-Cl-Ph | CH(Me)CH$_2$-(3,4-(methylenedioxy)-Ph) |
| 245 | 4-Cl-Ph | 4-(3-(OCH$_2$CH$_2$OEt)-Ph)-Ph |
| 246 | 4-Cl-Ph | 4-(indan-1-on-5-yl)-Ph |
| 247 | 4-Cl-Ph | 4-(4-Et-Ph)-Ph |
| 248 | 4-Cl-Ph | 4-(5-CO$_2$Et-furan-2-yl)-Ph |
| 249 | 4-Cl-Ph | 4-(2-ethyl-phenyl)-Ph |
| 250 | 4-Cl-Ph | 2,4-di-propoxy-Ph |
| 251 | 4-Cl-Ph | 2-propoxy-5-F-Ph |
| 252 | 4-Cl-Ph | 3,5-di-Br-2-propoxy-Ph |
| 253 | 4-Cl-Ph | 2-propoxy-5-Cl-Ph |

TABLE-continued

|   | | | |
|---|---|---|---|
| 254 | 4-Cl-Ph | | 2-propoxy-3-Cl-Ph |
| 255 | 4-Cl-Ph | | 2-propoxy-3-F-Ph |
| 256 | 4-Cl-Ph | | 4-(5-pyrimidinyl)-Ph |
| 257 | 4-Cl-Ph | | cyclohexyl |
| 258 | 2-Br-Ph | | 4-F-Ph |

| Cp. | R¹ | (Rᵃ)₀₋₃-Har | R⁴ | R³ | R² |
|---|---|---|---|---|---|
| 259 | H | 3-Pyr | 4-F-Ph | H | 4-Cl-Phenyl |
| 260 | H | 4-Pyr | 4-F-Ph | Br | 4-Cl-Phenyl |
| 261 | H | 4-Pyr | 4-F-Ph | Cl | 4-Cl-Ph |
| [262 | H | 4-quinolinyl | 4-F-Ph | H | 4-Cl-Ph] |
| 263 | H | 4-(2-F)-pyr | 4-F-Ph | H | 4-Cl-Ph |
| 264 | H | 3-F-4-pyr | 4-F-Ph | H | 4-Cl-Ph |
| 265 | H | 3-(Me)-4-pyridyl | 4-F-Ph | H | 4-Cl-Ph |
| 266 | H | 4-(2-Me)-pyridyl | 4-F-Ph | H | 4-Cl-Ph |
| 267 | 2-OH-Ph | 4-pyr | 2-F-4-Br-Ph | H | 4-Cl-Ph |
| 268 | H | 4-pyr | 4-F-Ph | Me | 4-Cl-Ph |
| 269 | H | 4-Pyr | 4-F-Ph | Et | 4-Cl-Ph |
| 270 | H | 4-Pyr | 4-F-Ph | Ph | 4-Cl-Ph |
| 271 | H | 2-NH₂-pyridin-4-yl | 4-F-Ph | H | 4-Cl-Ph |
| [272 | H | pyrimidin-4-yl | 4-F-Ph | H | 4-Cl-Ph] |
| [273 | H | quinolin-6-yl | 4-F-Ph | H | 4-Cl-Ph] |
| 274 | H | 2-F-pyridin-5-yl | 4-F-Ph | H | 4-Cl-Ph |
| 275 | H | 4-Pyr | 3-CF₃-Ph | Me | N-methyl-piperidin-4-yl |
| 276 | H | 4-Pyr | 3-CF₃-Ph | Me | piperidin-4-yl |
| 277 | H | 2-OH-pyridin-5-yl | 4-F-Ph | H | 4-Cl-Ph |
| [278 | H | pyridazin-4-yl | 4-F-Ph | H | 4-Cl-Ph] |
| 279 | H | 4-Pyr | 4-F-Ph | H | 2-CN-Ph |
| 280 | H | 4-Pyr | 2-CN-Ph | H | 4-Cl-Ph |
| 281 | H | 4-Pyr | 4-F-Ph | n-Bu | 4-Cl-Ph |
| 282 | H | 4-Pyr | 2-propoxy-4-(2-Ph-ethynyl)-Ph | H | 4-Cl-Ph |
| 283 | H | 4-Pyr | 4-(2-propenyl)-cyclohexen-1-yl | H | 4-Cl-Ph |
| 284 | H | 4-Pyr | N-(Cbz)-piperidin-4-yl | H | 4-Cl-Ph |
| 285 | H | 4-Pyr | i-Propyl | H | 4-Cl-Ph |

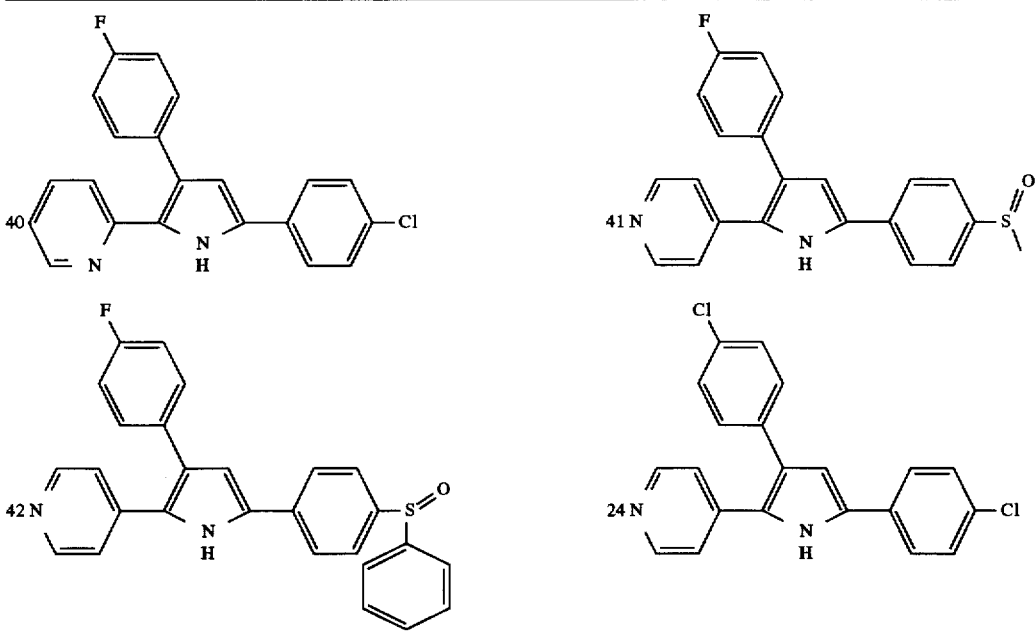

TABLE-continued
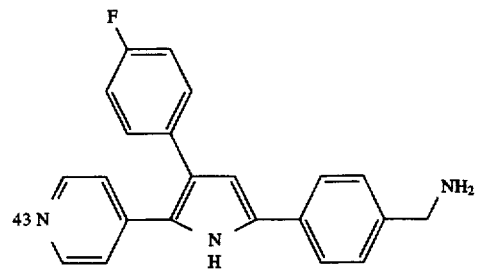
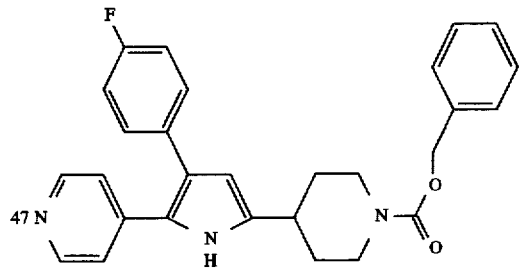
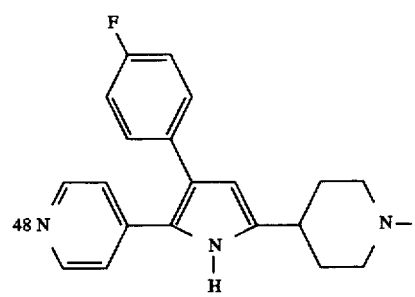
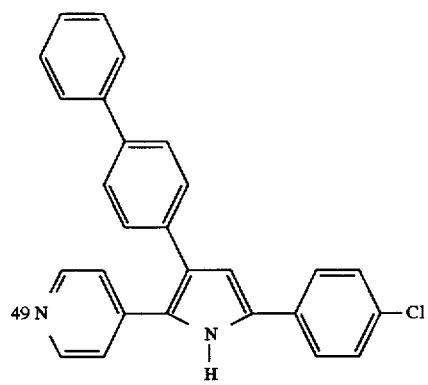
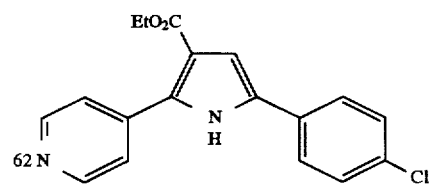
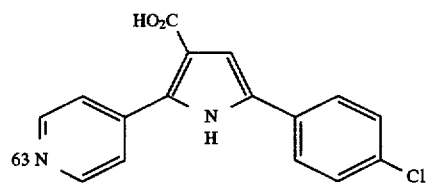
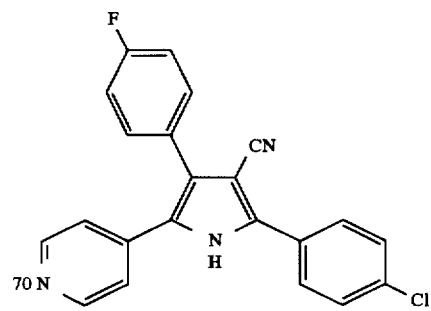
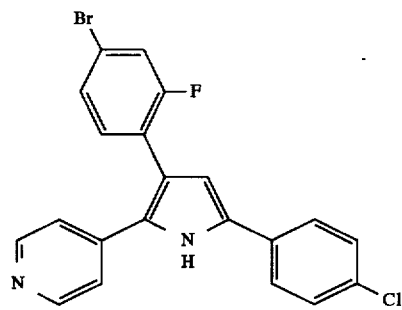
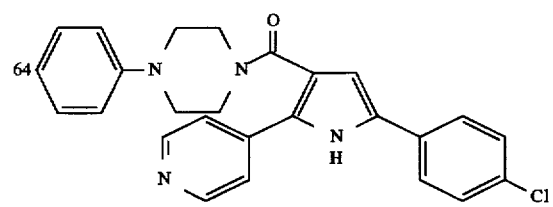
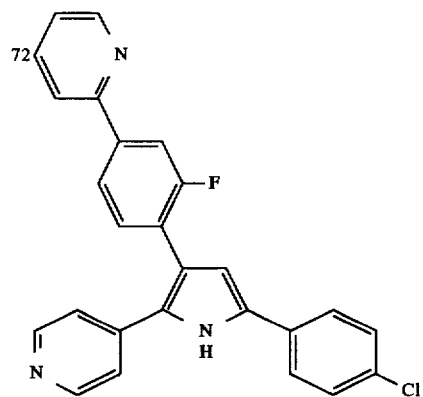

| TABLE-continued |
|---|
| 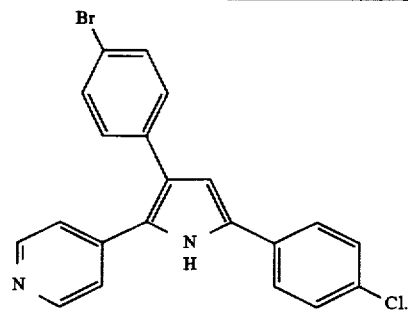 |

23. A method of treating diabetes disease in a mammal in need of such treatment, which comprises administering to said mammal an effective amount of a glucagon antagonist.

24. A method of treating diabetes disease in a mammal in need of such treatment, which comprises administering to said mammal an effective amount of a glucagon antagonist of claim 1.

25. A method of treating a cytokine mediated disease in a mammal in need of such treatment, which comprises administering to said mammal a compound of claim 1 an amount effective for treating said cytokine mediated disease.

26. The method according to claim 25 wherein the cytokine inhibited is IL-1.

27. The method according to claim 25 wherein the cytokine inhibited is TNF.

28. The method according to claim 25 wherein the cytokine inhibited is IL-8.

29. The method according to claim 25 wherein the cytokine mediated disease is septic shock, endotoxic shock, gram negative sepsis or toxic shock syndrome.

30. The method according to claim 25 wherein the cytokine mediated disease is bone resorption disease, graft versus host reaction, atherosclerosis, arthritis, osteoarthritis, rheumatoid arthritis, gout, psoriasis, or a topical inflammatory disease.

31. The method according to claim 25 wherein the cytokine mediated disease is adult respiratory distress syndrome, asthma, or chronic pulmonary inflammatory disease.

32. The method according to claim 25 wherein the cytokine mediated disease is cardiac and renal reperfusion injury, thrombosis or glomerulonephritis.

33. The method according to claim 25 wherein the cytokine mediated disease is Crohn's disease, ulcerative colitis or inflammatory bowel disease.

34. The method according to claim 25 wherein the cytokine mediated disease is cachexia.

35. The method according to claim 25 wherein the cytokine mediated disease is a viral infection.

36. A method of treating inflammation mediated by excess production of prostaglandin's in a human in need of such treatment, which comprises administering to said human an effective cytokine interfering amount of a compound of claim 1.

37. The method of claim 36 wherein the prostaglandin is $PGE_2$.

38. A pharmaceutical composition comprising a compound according to claim 1 and a pharmaceutically acceptable carrier.

39. A compound having the structure:

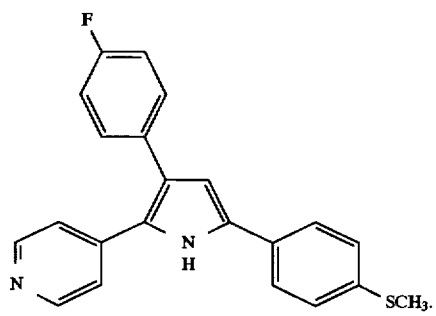

* * * * *